(12) United States Patent
Bairstow et al.

(10) Patent No.: US 8,841,248 B2
(45) Date of Patent: *Sep. 23, 2014

(54) MANUFACTURE OF INTER-ALPHA-INHIBITOR (IAIP) FROM PLASMA

(75) Inventors: Shawn F. Bairstow, Gurnee, IL (US); Jennifer Hutsell, Hainesville, IL (US); Sindhu Ramachandran, Lake Zurich, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 327 days.

This patent is subject to a terminal disclaimer.

(21) Appl. No.: 13/189,390

(22) Filed: Jul. 22, 2011

(65) Prior Publication Data
US 2012/0053113 A1 Mar. 1, 2012

Related U.S. Application Data

(60) Provisional application No. 61/367,331, filed on Jul. 23, 2010.

(51) Int. Cl.
*A61K 38/00* (2006.01)
*A61K 35/14* (2006.01)
*C07K 1/30* (2006.01)
*C07K 14/81* (2006.01)

(52) U.S. Cl.
CPC .................................. *C07K 14/811* (2013.01)
USPC ............. 514/1.4; 530/360; 530/418; 530/424

(58) Field of Classification Search
None
See application file for complete search history.

(56) References Cited

U.S. PATENT DOCUMENTS

| | | | | |
|---|---|---|---|---|
| 5,055,447 A | * | 10/1991 | Palladino et al. | .......... 424/164.1 |
| 7,932,365 B2 | | 4/2011 | Lim et al. | |
| 8,304,524 B2 | * | 11/2012 | Bairstow et al. | .............. 530/424 |
| 2003/0190732 A1 | | 10/2003 | Josic | |

FOREIGN PATENT DOCUMENTS

| | | |
|---|---|---|
| WO | WO 95/11260 A1 | 4/1995 |
| WO | WO 2005/046587 A2 | 5/2005 |
| WO | WO 2008/113589 A1 | 9/2008 |
| WO | WO 2009/154695 | * 12/2009 |
| WO | WO 2009/154695 A1 | 12/2009 |
| WO | WO 2011/011753 A1 | 1/2011 |

OTHER PUBLICATIONS

International Search Report mailed on Dec. 22, 2011, for International Patent Application No. PCT/US2011/045099 filed Jul. 22, 2011, 6 pages.
Jourdain. M. et al., "Effects of Inter-α-inhibitor in Experimental Endotoxic Shock and Disseminated Intravascular Coagulation," *Am J Respir Crit Care Med*, 1997, vol. 156, pp. 1825-1833.
Lim, Y-P. et al., "Correlation between Mortality and the Levels of Inter-Alpha Inhibitors in the Plasma of Patients with Severe Sepsis," *The Journal of Infectious Diseases*, Sep. 15, 2003, vol. 188, pp. 919-926.
Lim, Y-P. et al., "Affinity purification and enzymatic cleavage of inter-alpha inhibitor proteins using antibody and elastase immobilized on CIM monolithic disks," *Journal of Chromatography A*, 2005, vol. 1065, pp. 39-43.
McCann, K.B. "Evaluation of expanded bed adsorption chromatography for extraction of prothrombin complex from Cohn Supernatant I," *Biologicals*, 2008, vol. 36, pp. 227-223.
Michalski, C. et al., "Preparation and Properties of a Therapeutic Inter-Alpha-Trypsin Inhibitor Concentrate from Human Plasma," *Vox Sang*, 1994, vol. 67, pp. 329-336.
Mizon, C. et al., "Human pre-α-inhibitor; isolation from a by-product of industrial scale plasma fractionation and structural analysis of its H3 heavy chain," *Journal of Chromatography B*, 1997, vol. 692, pp. 281-291.
Opal, S.M. et al., "Longitudinal studies of inter-alpha inhibitor proteins in severely septic patients: A potential clinical marker and mediator of severe sepsis," *Crit Care Med*, 2007, vol. 35, No. 2, pp. 387-392.
Salier, J-P. et al., "The inter-α-inhibitor family: from structure to regulation," *Biochem J.*, 1996, vol. 315, pp. 1-9.
Wu, R. et al., "Delayed administration of human inter-βinhibitor proteins reduces mortality in sepsis," *Crit Care Med*, 2004, vol. 32, No. 8, pp. 1747-1752.
Yang, S. et al., "Administration of human inter-α-inhibitors maintains hemodynamic stability and improves survival during sepsis," *Crit Care Med*, 2002, vol. 30, No. 3, pp. 617-622.
Zhuo, L. et al., "Inter-α-trypsin Inhibitor, a Covalent Protein-Glycosaminoglycan-Protein Complex," *The Journal of Biological Chemistry*, Sep. 10, 2004, vol. 279, No. 37, pp. 38079-38082.

* cited by examiner

*Primary Examiner* — Suzanne M Noakes
(74) *Attorney, Agent, or Firm* — Morgan, Lewis & Bockius LLP

(57) ABSTRACT

The present invention provides compositions and pharmaceutical formulations of IaIp derived from plasma. Also provided are methods for the manufacture of the IaIp compositions and formulations, as well as method for the treatment of diseases associated with IaIp dysfunction.

50 Claims, 8 Drawing Sheets

Gel 1: IVIG Pathway

1) MW
2) Cohn Pool
3) Fraction I Sup
4) Fraction I Pre
5) Fraction II + III Sup
6) Fraction II + III Pre
7) Aerosil Filtercake
8) Aerosil Filtrate
9) Precipitate G Sup
10) Precipitate G NOTE: upper band = Ial; lower band = Pal Gel 2: Albumin Pathway 1) -
2) MW
3) Aerosil Filtercake
4) Fraction IV-1 Sup
5) Fraction IV-1 Pre
6) Fraction IV-4 Sup
7) Fraction IV-4 Pre
8) Fraction V

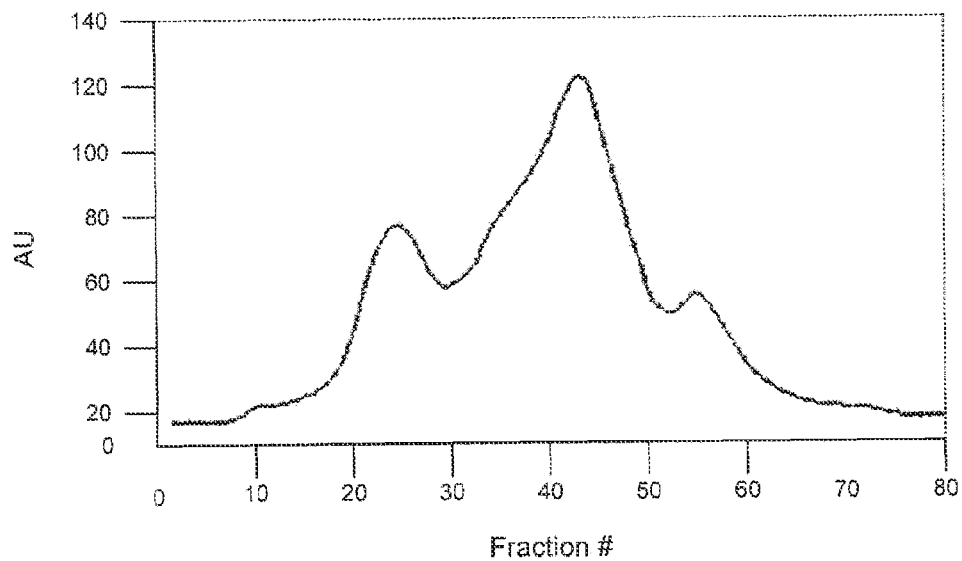
*FIG. 4A*
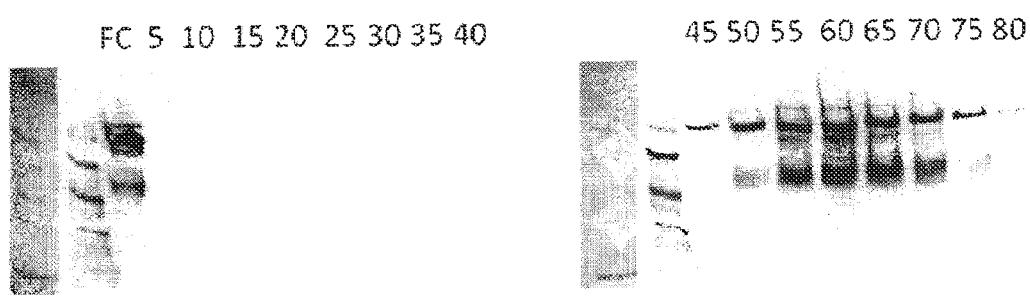
*FIG. 4B*  *FIG. 4C*

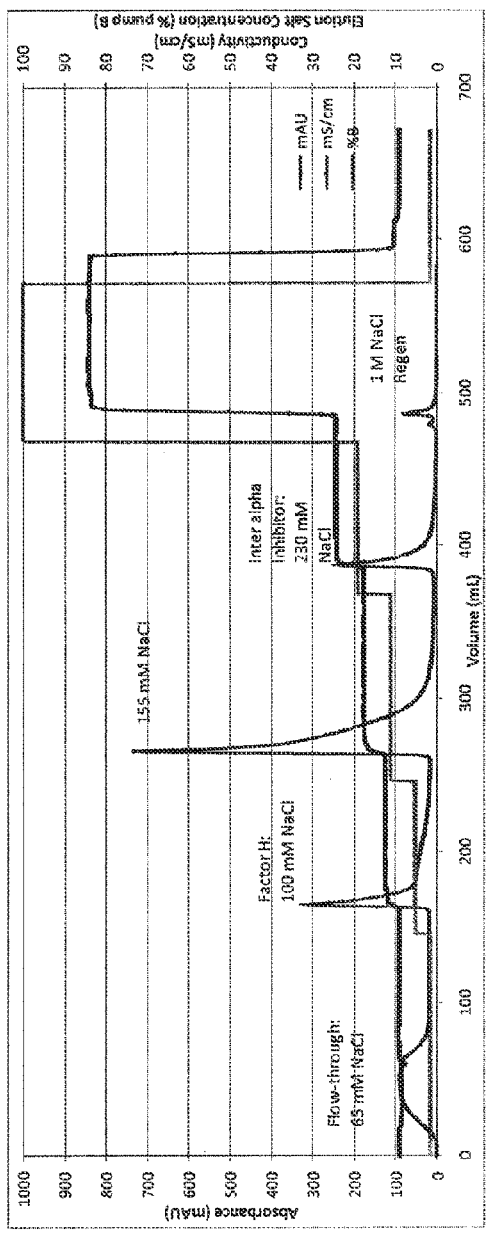
*FIG. 7A*
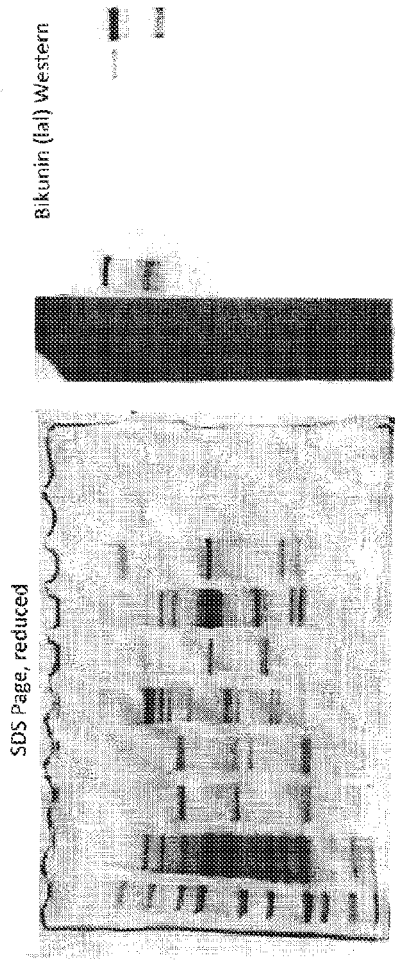
*FIG. 7B*
*FIG. 7C*

MANUFACTURE OF INTER-ALPHA-INHIBITOR (IAIP) FROM PLASMA

CROSS REFERENCES TO APPLICATIONS

This application claims priority to U.S. Provisional Patent Application Ser. No. 61/367,331, filed Jul. 23, 2010, the disclosure of which is hereby incorporated herein by reference in its entirety for all purposes.

BACKGROUND OF THE INVENTION

Unlike other biologics that are produced via recombinant expression of DNA vectors in host cell lines, plasma-derived proteins are fractionated from human blood and plasma donations. Thus, the supply of these products cannot be increased by simply increasing the volume of production. Rather the level of commercially available blood products is limited by the available supply of blood and plasma donations. This dynamic results in a shortage in the availability of raw human plasma for the manufacture of new plasma-derived blood factors that have lesser established commercial markets, including Inter-alpha-Inhibitor proteins (IaIp), such as Inter-alpha Trypsin Inhibitor (IaI) and Pre-alpha-Inhibitor (PaI), and Factor H.

Inter-alpha Trypsin Inhibitor (IaI) is a plasma protein that belongs to a family of protease inhibitors (Inter-alpha-Inhibitor proteins; IaIp) with roles in sepsis, cancer metastasis and inflammation (for review, see, Salier, J, et al., *Biochem J* 315: 1-9 (1996)). IaI has an approximate molecular weight of 225 kDa and is composed of two heavy chains (H1 and H2) and a single light chain (bikunin) polypeptide covalently linked liked by chondroitin sulfate (FIG. 1). Pre-alpha-Inhibitor (PaI) is a related Inter-alpha-Inhibitor composed of one heavy chain (H3) and one small chain (bikunin) polypeptide, again covalently linked liked by chondroitin sulfate (FIG. 1). Inter-alpha-Inhibitor proteins (IaIp) are present at levels between about 600-1200 mg/L in adult plasma (Lim et al., *J Chromatogr A*. (2005) February 11; 1065(1):39-43).

Sepsis is a medical condition characterized by whole-body inflammatory, known as systemic inflammatory response syndrome (SIRS) and the presence of a known or suspected infection. Whole-body inflammation occurring in sepsis is commonly caused by the immune system's response to a bacterial, viral, or fungal infection that has spread throughout the organism via the blood stream. These infections commonly begin in the lungs (pneumonia), bladder and kidneys (urinary tract infections), skin (cellulitis), abdomen (such as appendicitis), and other areas (such as meningitis).

A marked increase in the number of cases of sepsis has occurred over the past 20 years. This increase is due in part to the increased reliance on treatments for cancer and organ-transplant patients with medications that weaken the immune system. Increased average lifespan and an aging world population have also contributed to the increased incidence of sepsis. Furthermore, the development of antibiotic-resistant bacteria has contributed to the number of cases of sepsis.

Studies have shown correlations between decreased plasma levels of IaIp and mortality in patients with severe sepsis (Lim et al., *J Infect Dis*. (2003) September 15; 188(6): 919-26 and Opal et al., *Crit. Care Med*. (2007) February; 35(2):387-92). Furthermore, several studies have shown that the administration of IaIp reduces mortality associated with sepsis and septic shock (Jourdain et al., *Am J Respir Crit. Care Med*. (1997) December; 156(6):1825-33; Yang et al., *Crit. Care Med*. (2002) March; 30(3):617-22; Lim et al., *J Infect Dis*. (2003) September 15; 188(6):919-26; and Wu et al., *Crit. Care Med*. (2004) August; 32(8):1747-52; the disclosures of which are incorporated by reference herein in their entireties for all purposes). While the relationship between IaIp and sepsis has been characterized, medicaments based on this relationship have thus far not been identified.

Due in part to the increasing global demand and fluctuations in the available supply of plasma-derived blood products, such as immunoglobulin products, several countries, including Australia and England, have implemented demand management programs to protect supplies of these products for the highest demand patients during times of product shortages.

For example, it has been reported that in 2007, 26.5 million liters of plasma were fractionated, generating 75.2 metric tons of IVIG, with an average production yield of 2.8 grams per liter (Robert P., supra). This same report estimated that global IVIG yields are expected to increase to about 3.43 grams per liter by 2012. However, due to the continued growth in global demand for IVIG, projected at between about 7% and 13% annually between now and 2015, more raw plasma will need to be dedicated to immunoglobulin purification to meet the demand in spite of the expected improvement of the overall IVIG yield. This requirement will limit the availability of plasma for the manufacture of new plasma-derived blood products.

Due to the lack of plasma available for the manufacture of new plasma-derived products, their manufacture must be integrated into the existing framework of the established manufacturing processes for plasma-derived products such as immunoglobulins and albumin. Inter-alpha-Inhibitors, implicated as a potential therapeutic for sepsis, among other conditions, is one such plasma-derived blood product that is gaining the attention of physicians. However, due to the resources devoted to, for example, IgG gamma globulin manufacture, methods are needed for the manufacture of IaIp that can be introduced into the existing manufacturing schemes. Several methods have been suggested to achieve just this, however, these methods rely on adsorption of IaIp from source material that is in high demand for the purification of essential products such as IVIG. For example, Michalski et al. (Vox Sang. 1994; 67(4):329-36) and Mizon et al. (J Chromatogr B Biomed Sci Appl., 1997 May 9; 692(2):281-91) describe methods wherein IaIp is adsorbed from cryo-poor plasma by successive anion exchange enrichment steps, followed by heparin affinity chromatography. Josic (U.S. Patent Application Publication No. 2003/0190732) describes a method wherein IaIp is isolated from raw plasma, a cryo-precipitate plasma fraction, or a cryo-poor plasma by size exclusion chromatography and optionally an adsorption step. Finally, Lim et al. (365; U.S. Pat. No. 7,932,365) and Lim et al. (695; WO 2009/154695) describe methods wherein IaIp is adsorbed via solid phase extraction from a cryo-supernatant or a cryo-poor-plasma (see, FIG. 8 and FIG. 1 of Lim et al. '365 and '695, respectively). Accordingly, the purification schemes provided by Michalski et al., Mizon et al., Josic, and Lim et al. (the disclosures of which are hereby incorporated by reference in their entireties for all purposes) consume valuable starting material, will require new regulatory approvals for the established products, and/or may even result in alterations of the characteristics of the established products.

As such, a need remains in the art for methods of manufacturing IaIp compositions that do not require the use of additional input plasma or the redesign and regulatory re-approval of existing manufacturing processes for commercially important plasma derived blood products, such as albumin and IgG gamma globulins for intravenous (IVIG) or subcutaneous administration. Advantageously, the present invention fulfills these and other needs by providing methods of manufacturing Inter-alpha-Inhibitor proteins (IaIp) that rely entirely on previously unused manufacturing fractions. Among other aspects, the present invention also provides novel IaIp compositions and methods for treating diseases and disorders associated with IaIp dysfunction or dysregulation. Finally, the present invention provides methods for the co-manufacture of IaIp and Factor H from plasma fractionations otherwise discarded during the manufacture of other blood factor compositions.

BRIEF SUMMARY OF INVENTION

Among other aspects, the present invention provides methods for preparing enriched compositions of plasma-derived IaIp. Advantageously, the methods provided herein allow for the industrial-scale preparation of IaIp compositions from materials otherwise discarded during the preparation of other commercially important blood products by plasma fractionation. In certain embodiments, the IaIp compositions provided herein will consist of a single IaIp polypeptide, for example, IaI or PaI. In other embodiments, the IaIp compositions provided herein will comprise a mixture of two or more Inter-alpha-Inhibitor proteins, for example IaI and PaI. As used herein, IaIp will refer to compositions of both single Inter-alpha-Inhibitor proteins and mixtures of two or more Inter-alpha-Inhibitor proteins.

In one aspect, the present invention provides a method for preparing an enriched IaIp composition from plasma, the method comprising the steps of: (a) providing a cryo-poor plasma fraction; (b) precipitating IaIp from the cryo-poor plasma fraction in at least a first ethanol precipitation reaction to form an IaIp-containing precipitate; and (c) extracting IaIp from the IaIp-containing precipitate, thereby forming an enriched IaIp composition; wherein the IaIp-precipitate is a selected from the group consisting of a Fraction II+III filter cake, a Fraction I precipitate, a Fraction I+II+III precipitate, a Fraction II+III precipitate, Fraction IV-1, a Kistler-Nitschmann Precipitate A, and a Kistler-Nitschmann Precipitate B In one aspect, the present invention provides a method for preparing an enriched IaIp composition from plasma by extracting IaIp from a suspended Fraction II+III filter cake. In one embodiment, the method involves the adsorption of IaIp from a suspended Fraction II+III precipitate and separation from the resulting supernatant.

In a second aspect, the present invention provides a method for preparing an enriched IaIp composition from plasma by precipitating IaIp from a plasma sample to obtain a precipitate and extracting the IaIp from the precipitate. In certain embodiments, the precipitate is a Fraction I, Fraction II+III, Fraction IV-1, Precipitate A, or Precipitate B precipitate. In yet other embodiments, methods are provided for preparing an enriched IaIp composition from plasma by extracting IaIp from more than one precipitate formed during fractionation of the plasma.

In a third aspect, the present invention provides aqueous compositions of plasma-derived IaIp prepared from materials otherwise discarded during the manufacture of other commercially important blood products by plasma fractionation.

In a fourth aspect, the present invention provides pharmaceutical compositions of plasma-derived IaIp prepared from materials otherwise discarded during the manufacture of other commercially important blood products by plasma fractionation.

In a fifth aspect, the present invention provides methods for treating a disease, disorder, or condition associated with IaIp dysfunction or dysregulation, in a subject in need thereof by administering a therapeutically effective dose of an IaIp composition prepared from materials otherwise discarded during the preparation of other commercially important blood products by plasma fractionation. Diseases and disorders associated with IaIp dysfunction include, but are not limited to, sepsis, septic shock, endotoxic shock, disseminated intravascular coagulation, and fibroproliferation.

In a sixth aspect, the present invention provides methods of promoting epithelial repair in a subject in need thereof by administering a therapeutically effective dose of an IaIp composition prepared from materials otherwise discarded during the preparation of other commercially important blood products by plasma fractionation.

In a seventh embodiment, the present invention provides a method for the co-manufacture of IaIp and Factor H compositions by extracting both factors from one or more fractions otherwise discarded during the manufacture of other commercially important blood products by plasma fractionation. In certain embodiments, IaIp and Factor H are recovered from a Fraction I precipitate, a Fraction II+III precipitate, a Fraction II+III filter cake, a Precipitate A precipitate, or a precipitate B precipitate.

BRIEF DESCRIPTION OF DRAWINGS

FIG. 4. (A) Chromatograph of a DEAE-Sepharose enrichment step of an IaIp purification process utilizing a modified Fraction II+III filter cake as the starting material. (B) Western blot analysis of the DEAE-Sepharose chromatography using an anti-Bikunin antibody.

FIG. 7. (A) Chromatograph, (B) SDS-Page Analysis, and (C) Western blot analysis of DEAE chromatography performed with step-wise elution of an IaIp solution extracted from a modified Fraction II+III filter cake. Lane 1 contains standard protein molecular weight markers; lane 2 contains a sample of the IaIp solution loaded onto the DEAE resin; lanes 3 and 4 contain samples of the flow through from the DEAE load; lane 5 contains a sample of the 100 mM elution peak; lane 6 contains a sample of the 100 mM elution shoulder; lane 7 contains a sample of the 155 mM elution peak; lane 8 contains a sample of the 230 mM elution peak; and lane 9 contains a commercial Factor H standard.

DETAILED DESCRIPTION OF INVENTION

I. Introduction

Figure 1:
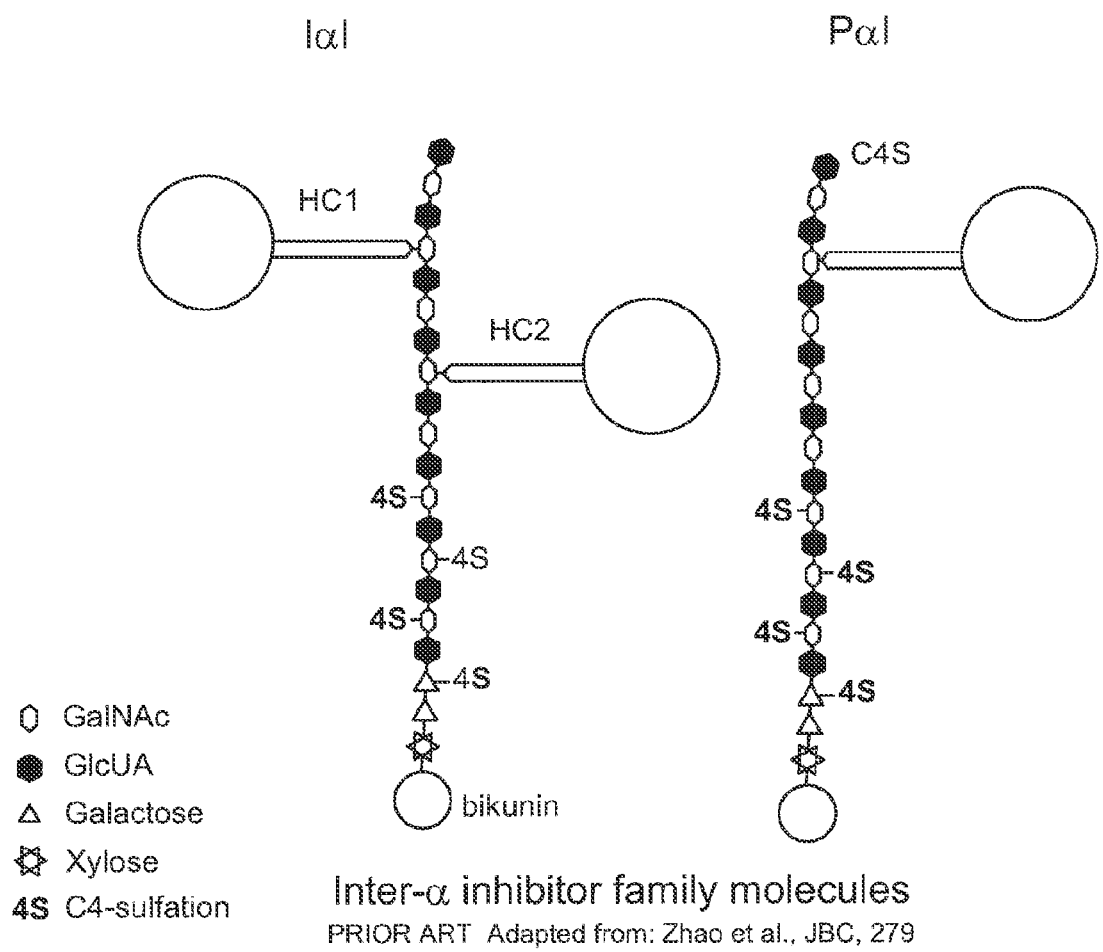
FIG. 1. Representation of the subunit composition and architecture of the Inter-alpha Trypsin Inhibitor (IaI) and Pre-alpha-Inhibitor (PaI) proteins.

IaIp has been implicated as a potential therapeutic for several human conditions and disease states, including sepsis, septic shock, endotoxic shock, disseminated intravascular coagulation, and fibroproliferation. The bikunin subunit of IaI and PaI is a serine protease that inhibits many serine proteases found in the blood, including, trypsin, thrombin, chymotrypsin, kallikrein, plasmin, elastase, cathepsin, Factors IXa, Xa, XIa, and XIIa. Accordingly, the bikunin subunit of many IaIp proteins functions to regulate the activity of these serine proteases during the promotion of inflammatory cascades, such as is found during infection (especially during sepsis), anthrax intoxication, cancer metastasis, tissue injury during surgery, kidney disease, vascular disease, coagulation, diabetes, and systemic inflammation (Pugia et al., *Adv Clin Chem.* 2007; 44:223-45). Notably, IaIp family members containing both a heavy chain and a bikunin subunit have longer vascular half-lives than does the bikunin subunit alone.

IaIp are relatively abundant plasma proteins (0.6 to 1.2 mg/mL plasma), however, these protein are currently discarded from the operations of various manufactures that specialize in the fractionation of human plasma. Among other aspects, the present invention provides methods for the isolation of IaIp from discard fractions of various fractionation processes, for example, Cohn, Oncley, Cohn-Oncley, Deutsch, Nitschmann, Kistler, and similar fractionation processes, without affecting, disrupting, or altering the normal or established processing of the plasma used for the manufacture of other plasma derived products. Thus, in one aspect, the invention makes use of discarded plasma fractions for the production of a useful medicament for the treatment of sepsis and other disorders.

Accordingly, in certain aspects, it is an object of the invention to provide methods of manufacturing aqueous, lyophilized, and pharmaceutical compositions of IaIp from a plasma source, for example pooled plasma. Advantageously, methods are provided herein for the preparation of IaIp compositions from unused plasma fractions created during the manufacture of other blood products, such as IgG gamma globulins and albumin.

In one embodiment, a method is provided for preparing an enriched Inter-alpha-Inhibitor (IaIp) composition from plasma, the method comprising the steps of: (i) forming a Fraction II+III precipitate from a plasma sample; (ii) re-suspending the Fraction II+III precipitate to form a Fraction II+III suspension; (iii) contacting the Fraction II+III suspension with a solid phase to remove the IaIp from the Fraction II+III suspension; and (iv) extracting the IaIp from the solid phase, thereby preparing an enriched IaIp composition. In a specific embodiment, the solid phase comprises finely divided silicon dioxide ($SiO_2$). In another specific embodiment, the solid phase comprises filter aid.

In one embodiment, a method is provided for preparing an enriched Inter-alpha-Inhibitor (IaIp) composition from plasma, the method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating IaIp from the first supernatant, in a second precipitation step, with between about 20% and about 25% alcohol at a pH of between about 6.7 and about 7.3 to form a second precipitate; (c) re-suspending the second precipitate to form a suspension; (d) mixing finely divided silicon dioxide ($SiO_2$) with the suspension from step (c); (e) filtering the suspension with a filter press, thereby forming a filter cake and a supernatant; and (f) extracting IaIp from the filter cake with an IaIp extraction buffer, thereby preparing an enriched IaIp composition.

In another embodiment, a method is provided for preparing an enriched Inter-alpha-Inhibitor (IaIp) composition from plasma, the method comprising the steps of: (a) precipitating IaIp from a plasma sample to obtain a precipitate, (b) extracting IaIp from the precipitate with an IaIp extraction buffer, thereby preparing an enriched IaIp composition, wherein the precipitate is a Fraction I, Fraction I+II+III, Fraction II+III, Fraction IV-1, Precipitate A, or Precipitate B precipitate.

In a specific embodiment of a method for preparing an enriched Inter-alpha-Inhibitor (IaIp) composition, the step of forming a Fraction I precipitate comprises precipitating IaIp from a cryo-poor plasma fraction, in a first precipitation step, with between about 6% and about 10% alcohol at a pH of between about 7.0 and about 7.5 to obtain a Fraction I precipitate.

In one specific embodiment of a method for preparing an enriched Inter-alpha-Inhibitor (IaIp) composition, wherein IaIp is extracted from a Fraction IV-1 precipitate, the method comprises the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating proteins from the first supernatant, in a second precipitation step, with between about 20% and about 25% alcohol at a pH of between about 6.7 and about 7.3 to form a second precipitate and a second supernatant; (c) precipitating IaIp from the second supernatant, in a third precipitation step, with between about 18% and about 23% alcohol at a pH of between about 5.0 to about 5.5 to form a third precipitate and a third supernatant; and (d) extracting IaIp from the third precipitate with an IaIp extraction buffer, thereby preparing an enriched IaIp composition.

In another specific embodiment of a method for preparing an enriched Inter-alpha-Inhibitor (IaIp) composition, wherein IaIp is extracted from a Fraction IV-1 precipitate, the method comprises the steps of: (a) precipitating proteins from a cryo-poor plasma fraction, in a first precipitation step, with between about 18% and about 23% alcohol at a pH of between about 6.7 and about 7.2 to obtain a first precipitate and a first supernatant; (b) precipitating IaIp from the first supernatant, in a second precipitation step, with between about 18% and about 25% alcohol at a pH of between about 5.0 to about 5.5 to form a second precipitate and a second supernatant; and (c) extracting IaIp from the second precipitate with an IaIp extraction buffer, thereby preparing an enriched IaIp composition.

In one embodiment of a method for preparing an enriched Inter-alpha-Inhibitor (IaIp) composition, IaIp is extracted from more than one plasma fraction. In certain embodiments, the plasma fractions are selected from a Fraction II+III filter cake, a Fraction I, Fraction I+II+III, Fraction II+III, Fraction IV-1, Precipitate A, or Precipitate B precipitate. In one embodiment, the method comprises the steps of: (a) fractionating a single aliquot of plasma to obtain enriched compositions of at least two blood products other than IaIp; (b) extracting IaIp from at least two different discard fractions created during the plasma fractionation with one or more extraction buffers; and (c) pooling the extracted IaIp fractions, thereby preparing an enriched IaIp composition. In one embodiment, the two other blood products are IgG gamma globulins (e.g., IVIG) and albumin. In yet other embodiments, the plasma is fractionated to obtain at least three blood products other than IaIp. Non-limiting examples of blood products that may be obtained in this method include, without limitation, IgG gamma globulins (e.g., IVIG), albumin, factor eight inhibitor bypass activity (FEIBA), Factor IX-complex, Factor VII-concentrate, Antithrombin III-complex, Factor VIII, prothrombin (Factor II), a prothrombin complex (with or without Factor VII), von Willebrand Factor (vWF), Complement Factor H(CFH), and the like.

In some embodiments of a method for the preparation of an enriched Inter-alpha-Inhibitor (IaIp) composition, IaIp is further enriched by precipitating impurities out of the extracted IaIp composition. In one embodiment, impurities are precipitated with between about 10% and about 19% alcohol (e.g., ethanol) at a pH of between about 6.0 and about 8.0. In other embodiments, IaIp is further enriched by precipitating IaIp from the extracted IaIp composition. In one embodiment, IaIp is precipitated from the extract with between about 20% and about 25% alcohol at a pH of between about 6.0 and about 8.0.

In certain embodiments of a method for the preparation of an enriched Inter-alpha-Inhibitor (IaIp) composition, IaIp recovered from a plasma fraction may be further purified by binding IaIp from the enriched IaIp composition to an anion exchange resin; and eluting the IaIp from the anion exchange resin with an elution buffer, thereby forming a first eluate containing IaIp. In other embodiments, IaIp recovered from a plasma fraction may be further purified by binding IaIp to a heparin affinity resin; and eluting the IaIp from the heparin affinity resin with an elution buffer. In yet other embodiments, IaIp may be further enriched by both anion exchange and heparin affinity chromatography. In one embodiment, IaIp is first bound to an anion exchange resin and then bound to a heparin affinity resin. In other embodiments, IaIp is first bound to a heparin affinity resin and then bound to an anion exchange resin.

In yet another embodiment, the present invention provides a method for preparing an enriched Inter-alpha-Inhibitor (IaIp) composition from plasma, the method comprising the steps of: (a) extracting IaIp from a precipitate formed during the fractionation of cryo-poor plasma, wherein the extract contains IaIp and Factor H; (b) binding the IaIp and Factor H to an anion exchange resin; (c) eluting the Factor H from the resin with a first elution buffer; and (d) eluting the IaIp from the resin with a second elution buffer, thereby preparing an enriched IaIp composition. In a related embodiment, the present invention provides a method for preparing an enriched Inter-alpha-Inhibitor (IaIp) composition from plasma, the method comprising the steps of: (a) extracting IaIp from a precipitate formed during the fractionation of cryo-poor plasma, wherein the extract contains IaIp and Factor H; (b) binding the IaIp to an anion exchange resin under conditions where Factor H does not bind to the anion exchange resin; and (c) eluting the IaIp from the resin with an elution buffer, thereby preparing an enriched IaIp composition. In certain embodiments, the IaIp composition is further enriched by heparin affinity chromatography.

In certain embodiments, the methods for producing an IaIp composition comprise the isolation of a single Inter-alpha-Inhibitor protein (IaIp) species. In one embodiment, the IaIp species is Inter-alpha-Trypsin Inhibitor (IaI). In another embodiment, the IaIp species is Pre-alpha-Inhibitor (PaI). In certain embodiments, the single IaIp species is isolated by an affinity step, for example, an antibody or aptamer affinity method.

In other aspects, it is an object of the invention to provide aqueous, lyophilized, and pharmaceutical compositions of IaIp from a plasma source, for example pooled plasma, which is prepared according to a method provided herein.

In yet other aspects, it is an object of the invention to provide methods of treating disorders and diseases associated with reduced IaIp function or IaIp dysfunction by administering a therapeutically effective amount of an IaIp composition provided herein. In one embodiment, the disease or disorder associated with reduced IaIp function or IaIp dysfunction is sepsis.

In another aspect, it is an object of the invention to provide methods of treating diseases and disorders associated with increased plasma serine protease activity by administering a therapeutically effective amount of an IaIp composition provided herein. In one embodiment, the disease or disorder associated increased plasma serine protease activity is selected from sepsis, septic shock, endotoxic shock, disseminated intravascular coagulation, fibroproliferation, anthrax intoxication, cancer metastasis, tissue injury during surgery, kidney disease, vascular disease, coagulation, diabetes, and systemic inflammation.

II. Definitions

As used herein, "Inter-alpha-Inhibitor proteins" or "IaIp" refers to a family of plasma protease inhibitors comprised of polypeptides encoded by one or more of the Alpha-1-microglobulin/bikunin precursor gene (AMBP; UniGene ID:231948, bikunin polypeptide), Inter-alpha (globulin) inhibitor H1 gene (ITIH1; UniGene ID:224173, H1 polypeptide), Inter-alpha (globulin) inhibitor H2 gene (ITIH2; UniGene ID:139782, H2 polypeptide), Inter-alpha (globulin) inhibitor H3 gene (ITIH3; UniGene ID:140017, H3 polypeptide), or Inter-alpha (globulin) inhibitor H4 (plasma Kallikrein-sensitive glycoprotein, H4 polypeptide) gene (ITIH4; UniGene ID:3321613). Exemplary IaIp protease inhibitors include, without limitation, IaI (bikunin, H1, and H2 polypeptides); PaI (bikunin and H3 polypeptides), IaLI (bikunin and H2 polypeptides), IaIH4P (H4 polypeptide), and bikunin (Salier, J, et al., supra).

As used herein, "cryo-poor plasma" refers to the supernatant formed after the cold precipitation (cryo-precipitation) of plasma or pooled plasma at temperatures nearing freezing, e.g., at temperatures below about 10° C. In the context of the present invention, plasma may refer interchangeably to recovered plasma (i.e., plasma that has been separated from whole blood ex vivo) or source plasma (i.e., plasma collected via plasmapheresis). Cryo-precipitation is commonly performed, for example, by thawing previously frozen pooled plasma, which has already been assayed for safety and quality considerations, although fresh plasma may also be used. In certain embodiments Thawing is typically carried out at a temperature no higher than 6° C. After complete thawing of the frozen plasma at low temperature, centrifugation is performed in the cold (e.g., ≤6° C.) to separate solid cryo-precipitates from the liquid supernatant. Alternatively, the separation step can be performed by filtration rather than centrifugation.

As used herein, a "Cohn pool" refers to the starting material used for the fractionation of a plasma sample or pool of plasma samples. Cohn pools include whole plasma, cryo-poor plasma samples, and pools of cryo-poor plasma samples that may or may not have been subjected to a pre-processing step. In certain embodiments, a Cohn pool is a cryo-poor plasma sample from which one or more blood factor have been removed in a pre-processing step, for example, adsorption onto a solid phase (e.g., aluminum hydroxide, finely divided silicon dioxide, etc.), or chromatographic step (e.g., ion exchange or heparin affinity chromatography). Various blood factors, including but not limited to Factor Eight Inhibitor Bypass Activity (FEIBA), Factor IX-complex, Factor VII-concentrate, or Antithrombin III-complex, may be isolated from the cryo-poor plasma sample to form a Cohn pool.

As used herein, a "Fraction II+III filter cake" refers to a solid phase recovered after treatment of a Cohn-Oncley or equivalent Fraction II+III suspension with an adsorptive material. Generally, a Fraction II+III suspension will be treated with an adsorptive material, for example, finely divided silicon dioxide, to remove impurities such as lipids, fibrinogen, amidolytic activity, prekallikren activity, and lipoproteins. Upon separation of the clarified Fraction II+III suspension supernatant, the recovered solid phase material is referred to as the Fraction II+III filter cake.

As used herein, "finely divided silicon dioxide" or "finely divided silica" refers to an oxide of silicon having the formula $SiO_2$, manufactured in a fashion that allows for the adsorption of IaIp onto its surface. Exemplary forms of finely divided silicon dioxide suitable for use in the methods of the present invention include, without limitation, fumed silica, pyrogenic silica, Aerosil®, Cab-O—Sil™, colloidal silica, diatomaceous earth, and the like. In a preferred embodiment, a commercial hydrophilic fumed silica product is used for the adsorption of IaIp from a plasma fraction. Non-limiting examples of these products include those marketed by Evonik Industries under the trade name Aerosil® (e.g., Aerosil 90, Aerosil 130, Aerosil 150, Aerosil 200, Aerosil 300, Aerosil 380, Aerosil OX 50, Aerosil EG 50, Aerosil TT 600, Aerosil 200 SP, Aerosil 300 SP, and Aerosil 300/30).

As used herein, a "disease or disorder associated with IaIp dysfunction or dysregulation" refers to any disease, disorder, or condition in a subject that is caused by, intensified by, characterized by, or results in a reduced level of IaIp activity in the subject. In some instances, diseases or disorders associated with IaIp dysfunction or dysregulation include conditions that are caused by or linked to mutations and polymorphism in any of the genes encoding an IaIp subunit. Similarly, a "disease or disorder associated with reduced IaIp function" refers to any disease, disorder, or conditions in a subject that is caused by, intensified by, characterized by, or results in a reduced level of IaIp activity in the subject. Diseases and disorders associated with IaIp dysfunction or reduced IaIp function include, but are not limited to, sepsis, septic shock, endotoxic shock, disseminated intravascular coagulation, and fibroproliferation.

As used herein, a "disease or disorder associated with increased plasma serine protease activity" refers to any disease, disorder, or condition in a subject that is caused by, intensified by, characterized by, or results in an increase in the serine protease activity found in the blood, and for which the administration of bikunin or a bikunin-containing protein (i.e., an IaIp protein) results in a reduction of the plasma serine protease activity. Various serine proteases may contribute to the increased plasma serine protease activity, including without limitation, trypsin, thrombin, chymotrypsin, kallikrein, plasmin, elastase, cathepsin, Factors IXa, Xa, XIa, and XIIa. Diseases and disorders associated with increased plasma serine protease activity include, but are not limited to, sepsis, septic shock, endotoxic shock, disseminated intravascular coagulation, fibroproliferation, anthrax intoxication, cancer metastasis, tissue injury during surgery, kidney disease, vascular disease, coagulation, diabetes, and systemic inflammation.

As used herein, the term "ultrafiltration (UF)" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular ($10^3$-$10^6$ Da) solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar, and is particularly useful for separating colloids like proteins from small molecules like sugars and salts.

As used herein, the term "diafiltration" is performed with the same membranes as ultrafiltration and is a tangential flow filtration. During diafiltration, buffer is introduced into the recycle tank while filtrate is removed from the unit operation. In processes where the product is in the retentate (for example Factor H), diafiltration washes components out of the product pool into the filtrate, thereby exchanging buffers and reducing the concentration of undesirable species.

As used herein, the term "about" denotes an approximate range of plus or minus 10% from a specified value. For instance, the language "about 20%" encompasses a range of 18-22%.

As used herein, the term "mixing" describes an act of causing equal distribution of two or more distinct compounds or substances in a solution or suspension by any form of agitation. Complete equal distribution of all ingredients in a solution or suspension is not required as a result of "mixing" as the term is used in this application.

As used herein, the term "solvent" encompasses any liquid substance capable of dissolving or dispersing one or more other substances. A solvent may be inorganic in nature, such as water, or it may be an organic liquid, such as ethanol, acetone, methyl acetate, ethyl acetate, hexane, petrol ether, etc. As used in the term "solvent detergent treatment," solvent denotes an organic solvent (e.g., tri-N-butyl phosphate), which is part of the solvent detergent mixture used to inactivate lipid-enveloped viruses in solution.

As used herein, the term "detergent" is used in this application interchangeably with the term "surfactant" or "surface acting agent." Surfactants are typically organic compounds that are amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Long chain fatty acids and their salts:

including caprylate, caprylic acid, heptanoat, hexanoic acid, heptanoic acid, nanoic acid, decanoic acid, and the like; Zwitterionic (amphoteric): dodecyl betaine; cocamidopropyl betaine; coco ampho glycinate; nonionic: alkyl poly(ethylene oxide), alkylphenol poly(ethylene oxide), copolymers of poly (ethylene oxide) and poly(propylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

As used herein, the term "therapeutically effective amount or dose" or "sufficient/effective amount or dose," refers to a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used in this application, the term "spraying" refers to a means of delivering a liquid substance into a system, e.g., during an alcohol precipitation step, such as a modified Cohn fractionation I or II+III precipitation step, in the form of fine droplets or mist of the liquid substance. Spraying may be achieved by any pressurized device, such as a container (e.g., a spray bottle), that has a spray head or a nozzle and is operated manually or automatically to generate a fine mist from a liquid. Typically, spraying is performed while the system receiving the liquid substance is continuously stirred or otherwise mixed to ensure rapid and equal distribution of the liquid within the system.

III. Methods for the Manufacture of Inter-Alpha-Inhibitor (IaIp)

Generally, IaIp preparations according to the present invention can be prepared from any suitable starting materials, for example, recovered plasma or source plasma. In a typical example, blood or plasma is collected from healthy donors. Usually, the blood is collected from the same species of animal as the subject to which the IaIp preparation will be administered (typically referred to as "homologous" IaIp). The IaIp is isolated from the blood or plasma by suitable procedures, such as, for example, precipitation (alcohol fractionation or polyethylene glycol fractionation), chromatographic methods (ion exchange chromatography, affinity chromatography, immunoaffinity chromatography, etc.) ultracentrifugation, and electrophoretic preparation, and the like. (See, e.g., Cohn et al., *J. Am. Chem. Soc.* 68:459-75 (1946); Deutsch et al., *J. Biol. Chem.* 164:109-118; Oncley et al., *J. Am. Chem. Soc.* 71:541-50 (1949); Cohn et al., *J. Am. Chem. Soc.* 72:465-474 (1950); Cohn et al., *Blood Cells and Plasma Proteins: Their State in Nature* (J. L. Tullis, ed), pp. 1-58, Academic Press, New York and London (1953); Nischmann et al., *Helv. Chim. Acta* 37:866-873; Kistler and Nischmann, *Vox Sang.* 7:414-424 (1962); Barundern et al., *Vox Sang.* 7:157-74 (1962); Koblet et al., *Vox Sang.* 13:93-102 (1967); U.S. Pat. Nos. 5,122,373 and 5,177,194; the disclosures of which are hereby incorporated by reference in their entireties for all purposes.

In certain embodiments, IaIp is recovered from material otherwise discarded during the manufacture of other commercially important blood products by plasma fractionation. For example, in exemplary embodiments, IaIp is extracted from a Cohn Fraction I or Fraction IV-1 precipitate (Cohn et al. (1946) supra), a Cohn-Oncley Fraction II+III precipitate (Oncley et al. supra), a Kistler and Nischmann Precipitate A or Precipitate B precipitate (Kistler and Nischmann supra), or adsorbed from a Cohn-Oncley Fraction II+III suspension (Oncley et al. supra) formed during the industrial manufacture of IgG gamma globulins. Advantageously, according to the methods provided herein, industrial-scale preparation of IaIp can be achieved without the need for additional input plasma or the redesign and regulatory re-approval of existing manufacturing processes for other commercially important plasma derived blood products, such as IgG gamma globulins for intravenous (IVIG) or subcutaneous administration or albumin.

In one aspect, the present invention provides a method for preparing an enriched IaIp composition by precipitating IaIp from cryo-poor plasma, or a fraction derived therefrom, in at least a first ethanol precipitation reaction to form an IaIp-containing precipitate; and (c) extracting IaIp from the IaIp-containing precipitate, thereby forming an enriched IaIp composition. In preferred embodiments, the IaIp-containing precipitate is selected from the group consisting of a Fraction II+III filter cake, a Fraction I precipitate, a Fraction I+II+III precipitate, a Fraction II+III precipitate, Fraction IV-1, a Kistler-Nitschmann Precipitate A, and a Kistler-Nitschmann Precipitate B.

In a specific embodiment, the method comprises precipitating IaIp from cryo-poor plasma, or a fraction derived therefrom, in at least a first ethanol precipitation reaction to form a Fraction II+III precipitate and extracting IaIp from the Fraction II+III precipitate. In one embodiment, the method further comprises enriching the IaIp composition by precipitating at least one impurity from the composition (i.e., in an "IaIp Precipitate 4" step) and separating the precipitated impurity from the IaIp-containing supernatant. In another embodiment, the method further comprises enriching the IaIp composition by precipitating IaIp from the composition (i.e., in an "IaIp Precipitate 5" step). In a specific embodiment, the method further comprises enriching the IaIp composition by anion exchange chromatography. In another specific embodiment, the method further comprises enriching the IaIp composition by heparin affinity chromatography. In one embodiment, the method further comprises enriching the IaIp composition by anion exchange chromatography and heparin affinity chromatography.

In one embodiment, the method comprises extracting IaIp from a Fraction II+III precipitate, precipitating at least one impurity from the composition, and precipitating IaIp from the resulting supernatant.

In another embodiment, the method comprises extracting IaIp from a Fraction II+III precipitate, precipitating at least one impurity from the composition, and enriching IaIp from the resulting supernatant by anion exchange chromatography.

In another embodiment, the method comprises extracting IaIp from a Fraction II+III precipitate, precipitating at least one impurity from the composition, and enriching IaIp from the resulting supernatant by heparin affinity chromatography.

In another embodiment, the method comprises extracting IaIp from a Fraction II+III precipitate, precipitating at least one impurity from the composition, and enriching IaIp from the resulting supernatant by anion exchange and heparin affinity chromatography.

In another embodiment, the method comprises extracting IaIp from a Fraction II+III precipitate, precipitating IaIp from the composition, and enriching IaIp from the resulting precipitate by anion exchange chromatography.

In another embodiment, the method comprises extracting IaIp from a Fraction II+III precipitate, precipitating IaIp from the composition, and enriching IaIp from the resulting precipitate by heparin affinity chromatography.

In another embodiment, the method comprises extracting IaIp from a Fraction II+III precipitate, precipitating IaIp from the composition, and enriching IaIp from the resulting precipitate by anion exchange and heparin affinity chromatography.

In one embodiment, the method comprises extracting IaIp from a Fraction II+III precipitate, precipitating at least one impurity from the composition, precipitating IaIp from the resulting supernatant, and enriching IaIp from the resulting precipitate by anion exchange chromatography.

In one embodiment, the method comprises extracting IaIp from a Fraction II+III precipitate, precipitating at least one impurity from the composition, precipitating IaIp from the resulting supernatant, and enriching IaIp from the resulting precipitate by heparin affinity chromatography.

In one embodiment, the method comprises extracting IaIp from a Fraction II+III precipitate, precipitating at least one impurity from the composition, precipitating IaIp from the resulting supernatant, and enriching IaIp from the resulting precipitate by anion exchange and heparin affinity chromatography.

In a specific embodiment, the method comprises precipitating IaIp from cryo-poor plasma, or a fraction derived therefrom, in at least a first ethanol precipitation reaction to form a Fraction II+III filter cake and extracting IaIp from the Fraction II+III filter cake. In one embodiment, the method further comprises enriching the IaIp composition by precipitating at least one impurity from the composition (i.e., in an "IaIp Precipitate 4" step) and separating the precipitated impurity from the IaIp-containing supernatant. In another embodiment, the method further comprises enriching the IaIp composition by precipitating IaIp from the composition (i.e., in an "IaIp Precipitate 5" step). In a specific embodiment, the method further comprises enriching the IaIp composition by anion exchange chromatography. In another specific embodiment, the method further comprises enriching the IaIp composition by heparin affinity chromatography. In one embodiment, the method further comprises enriching the IaIp composition by anion exchange chromatography and heparin affinity chromatography.

In one embodiment, the method comprises extracting IaIp from a Fraction II+III filter cake, precipitating at least one impurity from the composition, and precipitating IaIp from the resulting supernatant.

In another embodiment, the method comprises extracting IaIp from a Fraction II+III filter cake, precipitating at least one impurity from the composition, and enriching IaIp from the resulting supernatant by anion exchange chromatography.

In another embodiment, the method comprises extracting IaIp from a Fraction II+III filter cake, precipitating at least one impurity from the composition, and enriching IaIp from the resulting supernatant by heparin affinity chromatography.

In another embodiment, the method comprises extracting IaIp from a Fraction II+III filter cake, precipitating at least one impurity from the composition, and enriching IaIp from the resulting supernatant by anion exchange and heparin affinity chromatography.

In another embodiment, the method comprises extracting IaIp from a Fraction II+III filter cake, precipitating IaIp from the composition, and enriching IaIp from the resulting precipitate by anion exchange chromatography.

In another embodiment, the method comprises extracting IaIp from a Fraction II+III filter cake, precipitating IaIp from the composition, and enriching IaIp from the resulting precipitate by heparin affinity chromatography.

In another embodiment, the method comprises extracting IaIp from a Fraction II+III filter cake, precipitating IaIp from the composition, and enriching IaIp from the resulting precipitate by anion exchange and heparin affinity chromatography.

In one embodiment, the method comprises extracting IaIp from a Fraction II+III filter cake, precipitating at least one impurity from the composition, precipitating IaIp from the resulting supernatant, and enriching IaIp from the resulting precipitate by anion exchange chromatography.

In one embodiment, the method comprises extracting IaIp from a Fraction II+III filter cake, precipitating at least one impurity from the composition, precipitating IaIp from the resulting supernatant, and enriching IaIp from the resulting precipitate by heparin affinity chromatography.

In one embodiment, the method comprises extracting IaIp from a Fraction II+III filter cake, precipitating at least one impurity from the composition, precipitating IaIp from the resulting supernatant, and enriching IaIp from the resulting precipitate by anion exchange and heparin affinity chromatography.

In a specific embodiment, the method comprises precipitating IaIp from cryo-poor plasma, or a fraction derived therefrom, in at least a first ethanol precipitation reaction to form a Fraction II+III filter cake and extracting IaIp from the Fraction II+III filter cake. In one embodiment, the method further comprises enriching the IaIp composition by precipitating at least one impurity from the composition (i.e., in an "IaIp Precipitate 4" step) and separating the precipitated impurity from the IaIp-containing supernatant. In another embodiment, the method further comprises enriching the IaIp composition by precipitating IaIp from the composition (i.e., in an "IaIp Precipitate 5" step). In a specific embodiment, the method further comprises enriching the IaIp composition by anion exchange chromatography. In another specific embodiment, the method further comprises enriching the IaIp composition by heparin affinity chromatography. In one embodiment, the method further comprises enriching the IaIp composition by anion exchange chromatography and heparin affinity chromatography.

In one embodiment, the method comprises extracting IaIp from a Fraction II+III filter cake, precipitating at least one impurity from the composition, and precipitating IaIp from the resulting supernatant.

In another embodiment, the method comprises extracting IaIp from a Fraction II+III filter cake, precipitating at least one impurity from the composition, and enriching IaIp from the resulting supernatant by anion exchange chromatography.

In another embodiment, the method comprises extracting IaIp from a Fraction II+III filter cake, precipitating at least one impurity from the composition, and enriching IaIp from the resulting supernatant by heparin affinity chromatography.

In another embodiment, the method comprises extracting IaIp from a Fraction II+III filter cake, precipitating at least one impurity from the composition, and enriching IaIp from the resulting supernatant by anion exchange and heparin affinity chromatography.

In another embodiment, the method comprises extracting IaIp from a Fraction II+III filter cake, precipitating IaIp from the composition, and enriching IaIp from the resulting precipitate by anion exchange chromatography.

In another embodiment, the method comprises extracting IaIp from a Fraction II+III filter cake, precipitating IaIp from the composition, and enriching IaIp from the resulting precipitate by heparin affinity chromatography.

In another embodiment, the method comprises extracting IaIp from a Fraction II+III filter cake, precipitating IaIp from the composition, and enriching IaIp from the resulting precipitate by anion exchange and heparin affinity chromatography.

In one embodiment, the method comprises extracting IaIp from a Fraction II+III filter cake, precipitating at least one impurity from the composition, precipitating IaIp from the resulting supernatant, and enriching IaIp from the resulting precipitate by anion exchange chromatography.

In one embodiment, the method comprises extracting IaIp from a Fraction II+III filter cake, precipitating at least one impurity from the composition, precipitating IaIp from the resulting supernatant, and enriching IaIp from the resulting precipitate by heparin affinity chromatography.

In one embodiment, the method comprises extracting IaIp from a Fraction II+III filter cake, precipitating at least one impurity from the composition, precipitating IaIp from the resulting supernatant, and enriching IaIp from the resulting precipitate by anion exchange and heparin affinity chromatography.

In a specific embodiment, the method comprises precipitating IaIp from cryo-poor plasma, or a fraction derived therefrom, in at least a first ethanol precipitation reaction to form a Fraction I+II+II precipitate and extracting IaIp from the Fraction I+II+II precipitate. In one embodiment, the method further comprises enriching the IaIp composition by precipitating at least one impurity from the composition (i.e., in an "IaIp Precipitate 4" step) and separating the precipitated impurity from the IaIp-containing supernatant. In another embodiment, the method further comprises enriching the IaIp composition by precipitating IaIp from the composition (i.e., in an "IaIp Precipitate 5" step). In a specific embodiment, the method further comprises enriching the IaIp composition by anion exchange chromatography. In another specific embodiment, the method further comprises enriching the IaIp composition by heparin affinity chromatography. In one embodiment, the method further comprises enriching the IaIp composition by anion exchange chromatography and heparin affinity chromatography.

In one embodiment, the method comprises extracting IaIp from a Fraction I+II+II precipitate, precipitating at least one impurity from the composition, and precipitating IaIp from the resulting supernatant.

In another embodiment, the method comprises extracting IaIp from a Fraction I+II+II precipitate, precipitating at least one impurity from the composition, and enriching IaIp from the resulting supernatant by anion exchange chromatography.

In another embodiment, the method comprises extracting IaIp from a Fraction I+II+II precipitate, precipitating at least one impurity from the composition, and enriching IaIp from the resulting supernatant by heparin affinity chromatography.

In another embodiment, the method comprises extracting IaIp from a Fraction I+II+II precipitate, precipitating at least one impurity from the composition, and enriching IaIp from the resulting supernatant by anion exchange and heparin affinity chromatography.

In another embodiment, the method comprises extracting IaIp from a Fraction I+II+II precipitate, precipitating IaIp from the composition, and enriching IaIp from the resulting precipitate by anion exchange chromatography.

In another embodiment, the method comprises extracting IaIp from a Fraction I+II+II precipitate, precipitating IaIp from the composition, and enriching IaIp from the resulting precipitate by heparin affinity chromatography.

In another embodiment, the method comprises extracting IaIp from a Fraction I+II+II precipitate, precipitating IaIp from the composition, and enriching IaIp from the resulting precipitate by anion exchange and heparin affinity chromatography.

In one embodiment, the method comprises extracting IaIp from a Fraction I+II+II precipitate, precipitating at least one impurity from the composition, precipitating IaIp from the resulting supernatant, and enriching IaIp from the resulting precipitate by anion exchange chromatography.

In one embodiment, the method comprises extracting IaIp from a Fraction I+II+II precipitate, precipitating at least one impurity from the composition, precipitating IaIp from the resulting supernatant, and enriching IaIp from the resulting precipitate by heparin affinity chromatography.

In one embodiment, the method comprises extracting IaIp from a Fraction I+II+II precipitate, precipitating at least one impurity from the composition, precipitating IaIp from the resulting supernatant, and enriching IaIp from the resulting precipitate by anion exchange and heparin affinity chromatography.

In a specific embodiment, the method comprises precipitating IaIp from cryo-poor plasma, or a fraction derived therefrom, in at least a first ethanol precipitation reaction to form a Fraction IV-1 precipitate and extracting IaIp from the Fraction IV-1 precipitate. In one embodiment, the method further comprises enriching the IaIp composition by precipitating at least one impurity from the composition (i.e., in an "IaIp Precipitate 4" step) and separating the precipitated impurity from the IaIp-containing supernatant. In another embodiment, the method further comprises enriching the IaIp composition by precipitating IaIp from the composition (i.e., in an "IaIp Precipitate 5" step). In a specific embodiment, the method further comprises enriching the IaIp composition by anion exchange chromatography. In another specific embodiment, the method further comprises enriching the IaIp composition by heparin affinity chromatography. In one embodiment, the method further comprises enriching the IaIp composition by anion exchange chromatography and heparin affinity chromatography.

In one embodiment, the method comprises extracting IaIp from a Fraction IV-1 precipitate, precipitating at least one impurity from the composition, and precipitating IaIp from the resulting supernatant.

In another embodiment, the method comprises extracting IaIp from a Fraction IV-1 precipitate, precipitating at least one impurity from the composition, and enriching IaIp from the resulting supernatant by anion exchange chromatography.

In another embodiment, the method comprises extracting IaIp from a Fraction IV-1 precipitate, precipitating at least one impurity from the composition, and enriching IaIp from the resulting supernatant by heparin affinity chromatography.

In another embodiment, the method comprises extracting IaIp from a Fraction IV-1 precipitate, precipitating at least one impurity from the composition, and enriching IaIp from the resulting supernatant by anion exchange and heparin affinity chromatography.

In another embodiment, the method comprises extracting IaIp from a Fraction IV-1 precipitate, precipitating IaIp from the composition, and enriching IaIp from the resulting precipitate by anion exchange chromatography.

In another embodiment, the method comprises extracting IaIp from a Fraction IV-1 precipitate, precipitating IaIp from the composition, and enriching IaIp from the resulting precipitate by heparin affinity chromatography.

In another embodiment, the method comprises extracting IaIp from a Fraction IV-1 precipitate, precipitating IaIp from the composition, and enriching IaIp from the resulting precipitate by anion exchange and heparin affinity chromatography.

In one embodiment, the method comprises extracting IaIp from a Fraction IV-1 precipitate, precipitating at least one impurity from the composition, precipitating IaIp from the resulting supernatant, and enriching IaIp from the resulting precipitate by anion exchange chromatography.

In one embodiment, the method comprises extracting IaIp from a Fraction IV-1 precipitate, precipitating at least one impurity from the composition, precipitating IaIp from the resulting supernatant, and enriching IaIp from the resulting precipitate by heparin affinity chromatography.

In one embodiment, the method comprises extracting IaIp from a Fraction IV-1 precipitate, precipitating at least one impurity from the composition, precipitating IaIp from the resulting supernatant, and enriching IaIp from the resulting precipitate by anion exchange and heparin affinity chromatography.

In a specific embodiment, the method comprises precipitating IaIp from cryo-poor plasma, or a fraction derived therefrom, in at least a first ethanol precipitation reaction to form a Kistler-Nitschmann Precipitate A and extracting IaIp from the Kistler-Nitschmann Precipitate A.

In one embodiment, the method further comprises enriching the IaIp composition by precipitating at least one impurity from the composition (i.e., in an "IaIp Precipitate 4" step) and separating the precipitated impurity from the IaIp-containing supernatant. In another embodiment, the method further comprises enriching the IaIp composition by precipitating IaIp from the composition (i.e., in an "IaIp Precipitate 5" step). In a specific embodiment, the method further comprises enriching the IaIp composition by anion exchange chromatography. In another specific embodiment, the method further comprises enriching the IaIp composition by heparin affinity chromatography. In one embodiment, the method further comprises enriching the IaIp composition by anion exchange chromatography and heparin affinity chromatography.

In one embodiment, the method comprises extracting IaIp from a Kistler-Nitschmann Precipitate A, precipitating at least one impurity from the composition, and precipitating IaIp from the resulting supernatant.

In another embodiment, the method comprises extracting IaIp from a Kistler-Nitschmann Precipitate A, precipitating at least one impurity from the composition, and enriching IaIp from the resulting supernatant by anion exchange chromatography.

In another embodiment, the method comprises extracting IaIp from a Kistler-Nitschmann Precipitate A, precipitating at least one impurity from the composition, and enriching IaIp from the resulting supernatant by heparin affinity chromatography.

In another embodiment, the method comprises extracting IaIp from a Kistler-Nitschmann Precipitate A, precipitating at least one impurity from the composition, and enriching IaIp from the resulting supernatant by anion exchange and heparin affinity chromatography.

In another embodiment, the method comprises extracting IaIp from a Kistler-Nitschmann Precipitate A, precipitating IaIp from the composition, and enriching IaIp from the resulting precipitate by anion exchange chromatography.

In another embodiment, the method comprises extracting IaIp from a Kistler-Nitschmann Precipitate A, precipitating IaIp from the composition, and enriching IaIp from the resulting precipitate by heparin affinity chromatography.

In another embodiment, the method comprises extracting IaIp from a Kistler-Nitschmann Precipitate A, precipitating IaIp from the composition, and enriching IaIp from the resulting precipitate by anion exchange and heparin affinity chromatography.

In one embodiment, the method comprises extracting IaIp from a Kistler-Nitschmann Precipitate A, precipitating at least one impurity from the composition, precipitating IaIp from the resulting supernatant, and enriching IaIp from the resulting precipitate by anion exchange chromatography.

In one embodiment, the method comprises extracting IaIp from a Kistler-Nitschmann Precipitate A, precipitating at least one impurity from the composition, precipitating IaIp from the resulting supernatant, and enriching IaIp from the resulting precipitate by heparin affinity chromatography.

In one embodiment, the method comprises extracting IaIp from a Kistler-Nitschmann Precipitate A, precipitating at least one impurity from the composition, precipitating IaIp from the resulting supernatant, and enriching IaIp from the resulting precipitate by anion exchange and heparin affinity chromatography.

In a specific embodiment, the method comprises precipitating IaIp from cryo-poor plasma, or a fraction derived therefrom, in at least a first ethanol precipitation reaction to form a Kistler-Nitschmann Precipitate B and extracting IaIp from the Kistler-Nitschmann Precipitate B. In one embodiment, the method further comprises enriching the IaIp composition by precipitating at least one impurity from the composition (i.e., in an "IaIp Precipitate 4" step) and separating the precipitated impurity from the IaIp-containing supernatant. In another embodiment, the method further comprises enriching the IaIp composition by precipitating IaIp from the composition (i.e., in an "IaIp Precipitate 5" step). In a specific embodiment, the method further comprises enriching the IaIp composition by anion exchange chromatography. In another specific embodiment, the method further comprises enriching the IaIp composition by heparin affinity chromatography. In one embodiment, the method further comprises enriching the IaIp composition by anion exchange chromatography and heparin affinity chromatography.

In one embodiment, the method comprises extracting IaIp from a Kistler-Nitschmann Precipitate B, precipitating at least one impurity from the composition, and precipitating IaIp from the resulting supernatant.

In another embodiment, the method comprises extracting IaIp from a Kistler-Nitschmann Precipitate B, precipitating at least one impurity from the composition, and enriching IaIp from the resulting supernatant by anion exchange chromatography.

In another embodiment, the method comprises extracting IaIp from a Kistler-Nitschmann Precipitate B, precipitating at least one impurity from the composition, and enriching IaIp from the resulting supernatant by heparin affinity chromatography.

In another embodiment, the method comprises extracting IaIp from a Kistler-Nitschmann Precipitate B, precipitating at least one impurity from the composition, and enriching IaIp from the resulting supernatant by anion exchange and heparin affinity chromatography.

In another embodiment, the method comprises extracting IaIp from a Kistler-Nitschmann Precipitate B, precipitating IaIp from the composition, and enriching IaIp from the resulting precipitate by anion exchange chromatography.

In another embodiment, the method comprises extracting IaIp from a Kistler-Nitschmann Precipitate B, precipitating IaIp from the composition, and enriching IaIp from the resulting precipitate by heparin affinity chromatography.

In another embodiment, the method comprises extracting IaIp from a Kistler-Nitschmann Precipitate B, precipitating IaIp from the composition, and enriching IaIp from the resulting precipitate by anion exchange and heparin affinity chromatography.

In one embodiment, the method comprises extracting IaIp from a Kistler-Nitschmann Precipitate B, precipitating at least one impurity from the composition, precipitating IaIp from the resulting supernatant, and enriching IaIp from the resulting precipitate by anion exchange chromatography.

In one embodiment, the method comprises extracting IaIp from a Kistler-Nitschmann Precipitate B, precipitating at least one impurity from the composition, precipitating IaIp from the resulting supernatant, and enriching IaIp from the resulting precipitate by heparin affinity chromatography.

In one embodiment, the method comprises extracting IaIp from a Kistler-Nitschmann Precipitate B, precipitating at least one impurity from the composition, precipitating IaIp from the resulting supernatant, and enriching IaIp from the resulting precipitate by anion exchange and heparin affinity chromatography.

In one aspect, the present invention provides a method for preparing an enriched IaIp composition from plasma by extracting IaIp from a Fraction I, Fraction IV-1, Fraction II+III or Fraction I+II+III precipitate, a Kistler and Nitschmann Precipitate A or Precipitate B precipitate, or a Fraction II+III filter cake.

In certain embodiments, the enriched IaIp composition may be further purified subsequent to extraction from a Fraction I, Fraction IV-1, Fraction II+III or Fraction I+II+III precipitate, a Kistler and Nitschmann Precipitate A or Precipitate B precipitate, or a Fraction II+III filter cake. Various methods are available for further purifying IaIp, including without limitation, additional precipitation steps or fractionations, affinity chromatography, ion exchange chromatography, hydrophobic interaction chromatography, size exclusion chromatography, solvent/detergent (S/D) treatment, nanofiltration, ultrafiltration, diafiltration, and the like.

In one embodiment, the method further comprises precipitating impurities from an enriched IaIp composition. In certain embodiments, this step comprises precipitating at least one impurity, for example a lipid or protein, from the composition and then separating the precipitate from the supernatant containing IaIp. Optionally, IaIp can then be precipitated from the supernatant in a separate precipitation.

Advantageously, precipitation and subsequent re-suspension of IaIp from an enriched composition allows for the reduction of volume prior to additional purification steps, such as chromatography or nanofiltration. In one embodiment, the enriched IaIp composition may be further purified subsequent to extraction from a Fraction I, Fraction IV-1, Fraction II+III, or Fraction I+II+III precipitate, a Kistler and Nitschmann Precipitate A or Precipitate B precipitate, or a Fraction II+III filter cake by precipitating IaIp out of the enriched composition. In certain embodiments, an enriched IaIp composition may be subjected to a first precipitation step to remove at least one impurity from the composition, as described above, and then to a second precipitation step to precipitate and recover IaIp.

In certain embodiments, the method for preparing an enriched IaIp composition further comprises at least one, preferably two, chromatographic steps to further enrich the purity of the composition. Generally, any suitable chromatographic method may be employed to further enrich the IaIp composition extracted from a Fraction I, Fraction IV-1, Fraction II+III, or Fraction I+II+III precipitate, a Kistler and Nitschmann Precipitate A or Precipitate B precipitate, or a Fraction II+III filter cake. In certain embodiments, prior to chromatographic enrichment, the extracted IaIp composition will be subjected one or more additional precipitation steps, as described above, to reduce the impurities present in the composition, reduce the load volume for the chromatographic step, and/or exchange the buffer of the composition.

In certain embodiments, the chromatographic step may comprise anion exchange chromatography (AEC), cation exchange chromatography (CEC), heparin affinity chromatography, hydrophobic exchange chromatography (HIC), hydroxyapatite chromatography (HAP), immunoaffinity chromatography, size exclusion chromatography (i.e., gel filtration), or other suitable chromatographic step. Chromatographic steps may be performed in either batch or column mode.

In a preferred embodiment, the method comprises the use of anion exchange chromatography and heparin affinity chromatography.

In certain embodiments, the methods provided herein for the preparation of an enriched IaIp composition will further include at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43):1023-1028, both of which are herein expressly incorporated by reference in their entirety for all purposes), nanofiltration (Hamamoto et al., *Vox Sang* 1989 (56)230-236 and Yuasa et al., *J Gen Virol.* 1991 (72 (pt 8)):2021-2024, both of which are herein expressly incorporated by reference in their entirety for all purposes), low pH incubation at high temperatures (Kempf et al., *Transfusion* 1991 (31)423-427 and Louie et al., *Biologicals* 1994 (22):13-19), and heat treatment of lyophilized Factor H compositions (Piszkiewicz et al., *Thromb Res.* 1987 Jul. 15; 47(2):235-41; Piszkiewicz et al., *Curr Stud Hematol Blood Transfus.* 1989; (56):44-54; Epstein and Fricke, *Arch Pathol Lab Med.* 1990 March; 114 (3):335-40)

In one embodiment, the present invention provides a method of preparing a virally safe enriched IaIp composition comprising (i) extracting IaIp from a Fraction II+III filter cake, (ii) performing a first precipitation step to precipitate at least one impurity from the IaIp composition, (iii) performing a second precipitation step to precipitate IaIp from the composition, and (iv) performing at least one viral inactivation or removal step, thereby preparing a virally safe enriched IaIp composition.

In another embodiment, the invention provides a method of preparing a virally safe enriched IaIp composition comprising (i) extracting IaIp from a Fraction I precipitate, (ii) performing a first precipitation step to precipitate at least one impurity from the IaIp composition, (iii) performing a second precipitation step to precipitate IaIp from the composition, and (iv) performing at least one viral inactivation or removal step, thereby preparing a virally safe enriched IaIp composition.

In another embodiment, the invention provides a method of preparing a virally safe enriched IaIp composition comprising (i) extracting IaIp from a Fraction II+III precipitate, (ii) performing a first precipitation step to precipitate at least one impurity from the IaIp composition, (iii) performing a second precipitation step to precipitate IaIp from the composition, and (iv) performing at least one viral inactivation or removal step, thereby preparing a virally safe enriched IaIp composition.

In another embodiment, the invention provides a method of preparing a virally safe enriched IaIp composition comprising (i) extracting IaIp from a Fraction IV-1 precipitate, (ii)

performing a first precipitation step to precipitate at least one impurity from the IaIp composition, (iii) performing a second precipitation step to precipitate IaIp from the composition, and (iv) performing at least one viral inactivation or removal step, thereby preparing a virally safe enriched IaIp composition.

In another embodiment, the invention provides a method of preparing a virally safe enriched IaIp composition comprising (i) extracting IaIp from a Precipitate A precipitate, (ii) performing a first precipitation step to precipitate at least one impurity from the IaIp composition, (iii) performing a second precipitation step to precipitate IaIp from the composition, and (iv) performing at least one viral inactivation or removal step, thereby preparing a virally safe enriched IaIp composition.

In another embodiment, the invention provides a method of preparing a virally safe enriched IaIp composition comprising (i) extracting IaIp from a Precipitate B precipitate, (ii) performing a first precipitation step to precipitate at least one impurity from the IaIp composition, (iii) performing a second precipitation step to precipitate IaIp from the composition, and (iv) performing at least one viral inactivation or removal step, thereby preparing a virally safe enriched IaIp composition.

In one aspect, IaIp isolated from material otherwise discarded during the manufacture of other commercially important blood products by plasma fractionation, e.g., a Fraction I, Fraction IV-1, or Precipitate B precipitate or Fraction II+III filter cake, may be further enriched by chromatography with a series of step elutions that are amenable to a large scale manufacturing process. In one embodiment, DEAE-sepharose and Heparin-sepharose chromatography resins are used with a suitable buffer system, for example, one containing 25 mM Tris and 5 mM EDTA (pH 8).

The chromatographic enrichment of an IaIp composition can be modified to use buffer systems other than Tris/EDTA at pH 8.0. These processes can be adapted for buffers and solutions commonly used in manufacturing of biopharmaceuticals. An example is a purification scheme using phosphate buffer at pH 7.0. The key parameter to successful purification is manipulation of conductivity or ionic strength to achieve separation of the desired compound. If pH of the buffer system is maintained at pH 8.0, the conductivity of the elution buffers must be matched to the purification process described here. If the pH of the buffer system is changed, some adjustment of the ionic strength will be needed which can be done with standard techniques used in optimization of chromatographic processes.

A. Alcohol Precipitation and Chromatographic Fractionation Methods

In one aspect, the present invention provides methods for the preparation of enriched compositions of IaIp from material otherwise discarded during the manufacturing process of a second blood factor. In an exemplary embodiment, IaIp can be recovered from fractions generated by the manufacturing process for plasma-derived IgG compositions, such as IgG compositions formulated for intravenous (i.e., IVIG), subcutaneous, and/or intramuscular administration. In a second exemplary embodiment, IaIp can be recovered from fractions generated by the manufacturing process for plasma-derived albumin.

In a preferred embodiment, a method for the preparation of an enriched composition of Factor H is provided, the method comprising (i) extracting Factor H from a Fraction I precipitate, Fraction II+III precipitate, Fraction IV-1 precipitate, Precipitate A precipitate, Precipitate B precipitate, Fraction II+III suspension, and/or Fraction II+III filter cake, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step; and (vi) performing at least one viral inactivation or removal step.

In one embodiment, a method for the preparation of an enriched composition of IaIp from material otherwise discarded during an IgG or albumin manufacturing process comprises one or more of the following steps.

1. Preparation of Cryo-Poor Plasma

In certain embodiments, the starting material used for the preparation of IaIp, Factor H and IgG compositions generally consists of either recovered plasma (i.e., plasma that has been separated from whole blood ex vivo) or source plasma (i.e., plasma collected via plasmapheresis). The purification process typically starts with thawing previously frozen pooled plasma, which has already been assayed for safety and quality considerations, although fresh plasma may also be used. In certain embodiments thawing is typically carried out at a temperature not higher than at or about 6° C. After complete thawing of the frozen plasma at low temperature, centrifugation is performed in the cold (e.g., ≤6° C.) to separate solid cryo-precipitates from the liquid supernatant. Alternatively, the separation step can be performed by filtration rather than centrifugation. The liquid supernatant (also referred to as "cryo-poor plasma," after cold-insoluble proteins removed by centrifugation from fresh thawed plasma) is then processed in the next step. Various additional steps can be taken at this juncture for the isolation of other blood coagulation factors and inhibitors, e.g., Factor Eight Inhibitor Bypass Activity (FEIBA), Factor IX-complex, Factor VII, or Antithrombin III-complex.

2. First Precipitation Step—Fraction I Precipitation

After preparation of the cryo-poor plasma, the solution is typically cooled to at or about 0±1° C. and the pH is adjusted to at or about between 7.0 and 7.5, preferably at or about between 7.1 and 7.3, most preferably about 7.2. In one embodiment, the pH of the cryo-poor plasma is adjusted to a pH of at or about 7.2. Pre-cooled ethanol is then added, while the plasma is stirred, to a target concentration of at or about between 6% and 10%. In a preferred embodiment, ethanol is added to a target concentration of at or about between 7% and 9%. In a more preferred embodiment, ethanol is added to a target concentration of at or about 8% (v/v). At the same time the temperature is further lowered to at or about between −4° C. and 0° C. In a preferred embodiment, the temperature is lowered to at or about −2° C., to precipitate components such as fibrinogen. Typically, the precipitation event will include a hold time of at least at or about 1 hour, although shorter or longer hold times may also be employed. Subsequently, the supernatant (Supernatant I), ideally containing the entirety of the IgG content present in the cryo-poor plasma, is then separated from the precipitate (Fraction I precipitate) by centrifugation, filtration, or another suitable method.

Typically, the Fraction I precipitation step is performed to remove impurities in the manufacturing process of plasma-derived blood factors such as IgG and albumin. Advantageously, it was found that a significant fraction of IaIp is present in this precipitate, which is normally discarded during the manufacturing process. Accordingly, in one embodiment, IaIp is extracted from the Fraction I precipitate. Suitable buffers and methods for the extraction of IaIp from the Fraction I precipitate are provided herein.

As compared to conventional methods employed as a first fractionation step for cryo-poor plasma (Cohn et al., supra;

Oncley et al., supra), the present invention provides, in several embodiments, methods that result in improved yields of plasma factors, (e.g., IaIp, Factor H, IgG, albumin, etc.). In one embodiment, the precipitating alcohol is added in a fashion that finely disperses or that rapidly disperses the alcohol at the point of addition. In one embodiment, the alcohol is added by spraying. In a second embodiment, the alcohol is added from below or directly adjacent to a stirring apparatus, for example, a propeller. Addition of alcohol by any of these mechanisms avoids local over-concentration of alcohol which occurs, for example, at the point of fluent addition and results in the irreversible denaturation of proteins and/or precipitation of proteins that would otherwise be recovered in the supernatant.

In another embodiment, one or more pH modifying agent is added in a fashion that finely disperses or that rapidly disperses the pH modifying agent at the point of addition. In a one embodiment, the pH modifying agent is added by spraying. In a second embodiment, the pH modifying agent is added from below or directly adjacent to a stirring apparatus, for example, a propeller. In a third embodiment, the pH modifying agent is added by sprinkling a solid pH modifying agent over a delocalized area.

In yet another embodiment, the pH of the solution is adjusted after addition of the alcohol. In a related embodiment, the pH of the solution is adjusted during the addition of the alcohol. In one embodiment, the pH of the solution is maintained at the desired pH during the precipitation hold or incubation time by continuously adjusting the pH of the solution. In a preferred embodiment, the alcohol is ethanol.

In certain embodiments, the pH of the solution is adjusted to at or about between 7.0 and 7.5 after the addition of the precipitating alcohol. In other embodiments, the pH of the solution is adjusted to at or about between 7.1 and 7.3 after addition of the precipitating alcohol. In yet other embodiments, the pH of the solution is adjusted to at or about 7.0 or at or about 7.1, 7.2, 7.3, 7.4, or 7.5 after addition of the precipitating alcohol. In a particular embodiment, the pH of the solution is adjusted to at or about 7.2 after addition of the precipitating alcohol. As such, in certain embodiments, a reduced amount of blood factor is irreversibly lost during the first precipitation step due to protein denaturation, as compared to an analogous precipitation step in which the pH of the solution is adjusted prior to but not after addition of the precipitating alcohol.

In other certain embodiments, the precipitating alcohol and/or the solution used to adjust the pH is added by spraying, rather than by fluent addition. As such, in certain embodiments, a reduced amount of blood factor is irreversibly lost during the first precipitation step due to protein denaturation, as compared to an analogous precipitation step in which the alcohol and/or solution used to adjust the pH is introduced by fluent addition.

In yet other embodiments, the pH of the solution is adjusted after addition of the precipitating alcohol and by adding the precipitating alcohol and/or a solution used to adjust the pH by spraying, rather than by fluent addition. In a particular embodiment, the pH of the solution is adjusted to at or about 7.2 after addition of the precipitating alcohol and by adding the precipitating alcohol and/or the solution used to adjust the pH by spraying, rather than by fluent addition.

3. Second Precipitation Step—Fraction II+III Precipitation

In order to enrich the content and purity of the relevant blood factors present in the Fraction I supernatant (e.g., IaIp, Factor H, IgG, albumin), the Fraction Supernatant I is subjected to a second precipitation step, which is a Cohn-Oncley Fraction II+III fractionation. Generally, the pH of the solution is adjusted to a pH of at or about between 6.6 and 7.2. In a preferred embodiment, the pH of the solution is adjusted to at or about between 6.6 and 6.8. In a more preferred embodiment, the pH of the solution is adjusted to a pH of at or about 6.7. Alcohol, preferably ethanol, is then added to the solution while being stirred to a final concentration of at or about between 20% and 25% (v/v) to precipitate IaIp, Factor H and IgG present in the fraction, while retaining the bulk of albumin in the supernatant. In a preferred embodiment, alcohol is added to a final concentration of at or about 25% (v/v) to precipitate the IaIp, Factor H, and IgG in the fraction.

Advantageously, it has been found that while the majority of IgG is present in the Fraction II+III precipitate, albumin is not precipitated under these conditions. Accordingly, the Fraction II+III precipitate can be processed for the manufacture of IgG gamma globulins, while the supernatant can be utilized in the manufacture of albumin. Since the remaining IaIp plasma content is distributed between the Fraction II+III precipitate and supernatant, the IaIp purification process diverges at this step. In the first pathway (herein referred to as the IgG pathway) the Fraction II+III precipitate is processed such that IaIp can be recovered from the Fraction II+III suspension and/or Fraction II+III filter cake. The second pathway (herein referred to as the albumin pathway) involves processing of the Fraction II+III supernatant and allows for recovery of IaIp from the Fraction IV-1 precipitate.

Prior to or concomitant with alcohol addition to the Fraction I supernatant, the solution is further cooled to at or about between $-5°$ C. and $-9°$ C. In a preferred embodiment, the solution is cooled to a temperature at or about $-7°$ C. After completion of the alcohol addition, the pH of the solution is immediately adjusted to at or about between 6.6 and 7.2. In a preferred embodiment, the pH of the solution is adjusted to at or about between 6.6 and 6.8. In a more preferred embodiment, the pH of the solution is adjusted to at or about 6.9. Typically, the precipitation event will include a hold time of at least at or about 10 hours, although shorter or longer hold times may also be employed. Subsequently, the precipitate (Fraction II+III), which contains a large fraction of the IaIp content, and the majority of the Factor H and IgG content, of the cryo-poor plasma, is separated from the supernatant by centrifugation, filtration, or another suitable method and collected. As compared to conventional methods employed as a second fractionation step for cryo-poor plasma (Cohn et al., supra; Oncley et al., supra), the present invention provides, in several embodiments, methods that result in improved blood factor yields in the Modified Fraction II+III precipitate.

As compared to conventional methods employed as a second fractionation step for cryo-poor plasma (Cohn et al., supra; Oncley et al., supra), the present invention provides, in several embodiments, methods that result in improved blood factor yields in the Fraction II+III precipitate. In one embodiment, the precipitating alcohol is added in a fashion that finely disperses the alcohol or that rapidly disperses the alcohol at the point of addition. In one embodiment, the alcohol is added by spraying. In a second embodiment, the alcohol is added from below or directly adjacent to a stirring apparatus, for example, a propeller.

In another embodiment, one or more pH modifying agent is added in a fashion that finely disperses or that rapidly disperses the pH modifying agent at the point of addition. In one embodiment, the pH modifying agent is added by spraying. In a second embodiment, the pH modifying agent is added from below or directly adjacent to a stirring apparatus, for example, a propeller. In a third embodiment, the pH modifying agent is added by sprinkling a solid pH modifying agent over a delocalized area.

In yet another embodiment, the pH of the solution is adjusted after addition of the alcohol. In a related embodiment, the pH of the solution is adjusted during addition of the alcohol. In one embodiment, the pH of the solution is maintained at the desired pH during the precipitation hold or incubation time by continuously adjusting the pH of the solution. In a preferred embodiment, the alcohol is ethanol.

In one embodiment, the temperature of the Fraction II+III precipitation step is at or about between −7° C. and −9° C. In a related embodiment, the concentration of alcohol (e.g., ethanol) used in the Fraction II+III precipitation step is at or about 25% (v/v) and the temperature is at or about between −7° C. and −9° C. In comparison, both Cohn et al. and Oncley et al. perform precipitation at −5° C. and Oncley et al. use 20% alcohol, in order to reduce the level of contaminants in the precipitate. Advantageously, the methods provided herein allow for maximal IaIp, Factor H, and/or IgG yield without high levels of contamination in the final product.

In another embodiment, the precipitation step is performed at a temperature at or about between −7° C. and −9° C. In one embodiment, the precipitation step is performed at a temperature of at or about −7° C. In another embodiment, the precipitation step is performed at a temperature of at or about −8° C. In another embodiment, the precipitation step is performed at a temperature of at or about −9° C.

In certain embodiments, the alcohol concentration of the precipitation step is between at or about 20% and at or about 30%, preferably between at or about 23% and at or about 27%. In a preferred embodiment, the alcohol concentration is between at or about 24% and at or about 26%. In another preferred embodiment, the alcohol concentration is at or about 25%. In other embodiments, the alcohol concentration may be at or about 20%, 21%, 22%, 23%, 24%, 25%, 26%, 27%, 28%, 29% or 30%. In a particular embodiment, the second precipitation step is performed at a temperature of at or about −7° C. with an alcohol concentration of at or about 25%. In one embodiment, the alcohol is ethanol.

It has been discovered that when the pH of the solution is adjusted to a pH of about 6.9 prior to addition of the precipitating alcohol, the pH of the solution shifts from 6.9 to between about 7.4 and about 7.7, due in part to protein precipitation. As the pH of the solution shifts away from 6.9, precipitation of IgG becomes less favorable and the precipitation of certain contaminants becomes more favorable. Advantageously, the inventors have found that by adjusting the pH of the solution after addition of the precipitating alcohol, that higher percentages of IgG is recovered in the Fraction II+III precipitate. In one embodiment, the pH of the solution is maintained at the desired pH during the precipitation hold or incubation time by continuously adjusting the pH of the solution. In a preferred embodiment, the alcohol is ethanol.

In certain embodiments, the pH of the solution is adjusted to at or about between 6.6 and 7.2 immediately after or during the addition of the precipitating alcohol. In another embodiment, the pH of the solution is maintained at or about between 6.6 and 7.2 continuously during the precipitation incubation period. In other embodiments, the pH of the solution is adjusted to at or about between 6.8 and 7.0 immediately after or during the addition of the precipitating alcohol, or to a pH of at or about 6.7, 6.8, 6.9, 7.0, or 7.1 immediately after or during the addition of the precipitating alcohol. In a particular embodiment, the pH of the solution is adjusted to at or about 6.9 immediately after or during the addition of the precipitating alcohol. In certain embodiments, the pH of the solution is maintained at or about between 6.8 and 7.0 continuously during the precipitation incubation period, or at a pH of at or about 6.9 continuously during the precipitation incubation period. In another embodiment, both the precipitating alcohol and the solution used to adjust the pH are added by spraying, rather than by fluent addition.

In another embodiment, the pH of the solution is adjusted to at or about between 6.7 and 7.1, or at or about 6.9, immediately after or during the addition of the precipitating alcohol by spray addition of either or both the alcohol and pH modifying agent. In one embodiment, the pH of the solution is maintained at or about between 6.7 and 7.1, or at or about 6.9, by continuously adjusting the pH during the precipitation incubation period by adding the precipitating alcohol and/or the solution used to adjust the pH by spraying, rather than by fluent addition. In another particular embodiment, the precipitation step is performed at a temperature at or about between −7° C. and −9° C., or at or about −7° C. with an alcohol concentration of at or about between 23% and 27%, or at or about 25%. In one embodiment, precipitation is performed at a temperature of at or about −7° C. with at or about 25% ethanol added by spraying, wherein pH of the solution is adjusted to at or about 6.9 after addition of the precipitating alcohol. In yet another embodiment, the pH of the solution is maintained at or about 6.9 for the entirety of the precipitation incubation or hold time.

4. The IgG Pathway a) Extraction of the Fraction II+III Precipitate

In order to solubilize the IaIp, Factor H, and IgG content of the Fraction II+III precipitate, a cold extraction buffer is used to re-suspend the Fractionation II+III precipitate at a typical ratio of at or about 1 part precipitate to 15 parts of extraction buffer. In another aspect, a cold extraction buffer is used to re-suspend the Fractionation II+III precipitate at a typical ratio of at or about 1 part precipitate to 20 parts of extraction buffer. Other suitable re-suspension ratios may be used, for example at a range of at or about between 1:4 and 1:40, or at or about between 1:8 and 1:30, or at or about between 1:10 and 1:20, or at or about between 1:12 and 1:18, or at or about between 1:13 and 1:17, or at or about between 1:14 and 1:16. In certain embodiments, the re-suspension ratio may be at or about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher. In a preferred embodiment, the Fraction II+III paste is re-suspended at or about a ratio of 1 part precipitate to 15 parts extraction buffer. In another preferred embodiment, the Fraction II+III paste is re-suspended at or about a ratio of 1 part precipitate to 20 parts extraction buffer.

Suitable solutions for the extraction of the II+III precipitate will generally have a pH at or about between 4.0 and 5.5. In certain embodiments, the solution will have a pH at or about between 4.3 and 4.7, in other embodiments, the extraction solution will have a pH of at or about 4.0, 4.1, 4.2, 4.3, 4.4, 4.5, 4.6, 4.7, 4.8, 4.9, 5.0, 5.1, 5.2, 5.3, 5.4, or 5.5. In a preferred embodiment, the pH of the extraction buffer will be at or about 4.3. In another preferred embodiment, the pH of the extraction buffer will be at or about 4.5. In another preferred embodiment, the pH of the extraction buffer will be at or about 4.7. Generally, these pH requirements can be met using a buffering agent selected from, for example, acetate, citrate, monobasic phosphate, dibasic phosphate, mixtures thereof, and the like. Suitable buffer concentrations typically range from about 2.5 to about 100 mM, or from about 5 to about 50 mM, or about 2.5, 5, 10, 15, 20, 25, 30, 35, 40, 45, 50, 55, 60, 65, 70, 75, 80, 85, 90, 95, or 100 mM buffering agent.

The extraction buffer will preferably have a conductivity of at or about between 0.5 mS·cm-1 and 2.0 mS·cm-1. For example, in certain embodiments, the conductivity of the extraction buffer will be at or about 0.5 mS·cm-1, or at or about 0.6, 0.7, 0.8, 0.9, 1.0, 1.1, 1.2, 1.3, 1.4, 1.5, 1.6, 1.7, 1.8, 1.9, or at or about 2.0 mS·cm-1. One of ordinary skill in the art will know how to generate extraction buffers having an appropriate conductivity.

In one particular embodiment, an exemplary extraction buffer may contain at or about 5 mM monobasic sodium phosphate and at or about 5 mM acetate at a pH of at or about 4.5±0.2 and conductivity of at or about 0.7 to 0.9 mS/cm.

Generally, the extraction is performed at or about between 0° C. and 20° C., preferably at or about between 2° C. and 8° C. In certain embodiments, the extraction may be performed at or about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. In a particular embodiment, the extraction is performed at or about between 2° C. and 10° C. Typically, the extraction process is performed under continuous stirring until all soluble components of the II+III paste are brought into solution. In certain embodiments, the extraction will proceed for at or about between 60 and 300 minutes, or for at or between 120 and 240 min, or for at or about between 150 and 210 minutes, while the suspension is continuously stirred. In certain embodiments, the extraction process will proceed for at or about 60, 70, 80, 90, 100, 110, 120, 130, 140, 150, 160, 170, 180, 190, 200, 210, 220, 230, 240, 250, 260, 270, 280, 290, or at or about 300 minutes. In a preferred embodiment, the extraction process will proceed for at least 60 minutes with continuous stirring.

In one embodiment, the extraction buffer will contain at or about 5 mM monobasic sodium phosphate, 5 mM acetate, and 0.051% to 0.06% glacial acetic acid (v/v). In a preferred embodiment, the Fraction II+III precipitate is extracted with a paste to buffer ratio of at or about 1:15 at a pH of at or about 4.5±0.2.

In one embodiment, the pH of the solution is maintained for the duration of the extraction process. In one embodiment, the pH of the solution is maintained at or about between 4.1 and 4.9 for the duration of the extraction process. In a preferred embodiment, the pH of the solution is maintained at or about between 4.2 and 4.8 for the duration of the extraction process. In a more preferred embodiment, the pH of the solution is maintained at or about between 4.3 and 4.7 for the duration of the extraction process. In another preferred embodiment, the pH of the solution is maintained at or about between 4.4 and 4.6 for the duration of the extraction process. In yet another preferred embodiment, the pH of the solution is maintained at or about 4.5 for the duration of the extraction process.

b) Pretreatment and Recovery of IaIp from the Fraction II+III Suspension

Figure 3A:
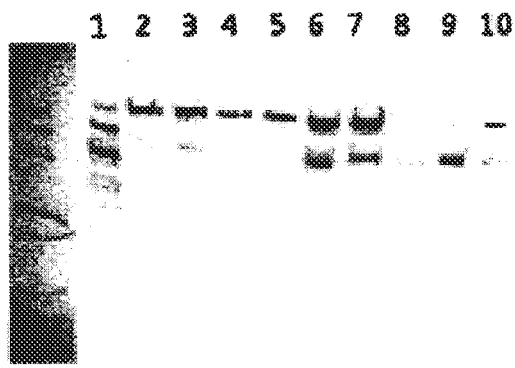
FIG. 3. Western Blot analysis of the IaIp content of intermediate plasma fractions created during the manufacture of (A) IgG gamma globulins and (B) albumin using an exemplary plasma fractionation scheme.
Figure 3B:
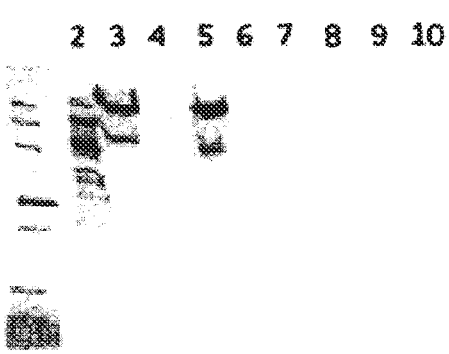

Advantageously, it has been found that pretreatment of solubilized Fraction II+III precipitate with finely divided silicon dioxide ($SiO_2$) significantly reduces impurities, such as lipids, fibrinogen, amidolytic activity, prekallikren activity, and lipoproteins, from the IgG manufacturing process. Unexpectedly, the inventors have found that the majority of IaIp found in the Fraction II+III suspension is drawn into the Fraction II+III filter cake. For example, Example 1 demonstrates that IaI and PaI can be detected in the Fraction II+III precipitate and filter cake, but is absent in the clarified Fraction II+III suspension after silicon dioxide treatment (FIG. 3). Furthermore, Example 2 demonstrates that IaIp is not irreversibly lost after silicon dioxide treatment and can be extracted from the Fraction II+III filter cake.

Accordingly, in one embodiment, IaIp is extracted from a Fraction II+III filter cake after treatment of a Fraction II+III suspension with finely divided silicon dioxide (e.g., Aerosil).

In certain embodiments, Fraction II+III precipitate that has been extracted with a suitable dissolution buffer will be treated with at or about between 5 mg and 100 mg finely divided silicon dioxide per gram of suspended Fraction II+III precipitate. In a preferred embodiment, the Fraction II+III suspension will be treated with at or about between 20 mg and 80 mg finely divided silicon dioxide per gram of suspended Fraction II+III precipitate. In a more preferred embodiment, the Fraction II+III suspension will be treated with at or about between 40 mg and 60 mg finely divided silicon dioxide per gram of suspended Fraction II+III precipitate. In another preferred embodiment, the Fraction II+III suspension will be treated with at or about 50 mg finely divided silicon dioxide per gram of suspended Fraction II+III precipitate. In certain embodiments, finely divided silicon dioxide is added at a concentration of at or about between 20 g/kg II+III paste and 100 g/kg II+III paste (i.e., for a Fraction II+III precipitate that is extracted at a ratio of 1:15, finely divided silicon dioxide should be added at a concentration at or about between 20 g/16 kg II+III suspension and 100 g/16 kg II+III suspension, or at a final concentration at or about between 0.125% (w/w) and 0.625% (w/w)). In certain embodiments, the finely divided silicon dioxide may be added at a concentration of at or about 5 g/kg II+III paste, or at or about 10, 15, 20, 25, 30, 35, 40, 45, 50, 55, 60, 65, 70, 75, 80, 85, 90, 95, or 100 g/kg II+III paste. In one specific embodiment, finely divided silicon dioxide is added to the Fraction II+III suspension to a final concentration of at or about 40 g/16 kg II+III suspension. In a preferred embodiment, the finely divided silicon dioxide used is Aerosil® 380 or an equivalent thereof.

Generally, the finely divided silicon dioxide treatment will be performed at a temperature at or about between 0° C. and 20° C., preferably at or about between 2° C. and 8° C. In certain embodiments, the treatment may be performed at or about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. Typically, the Fraction II+III suspension will be stirred with finely divided silicon dioxide for at least 15 minutes. In certain embodiments, the Fraction II+III suspension will be stirred with finely divided silicon dioxide for at least 10, 15, 20, 30, 40, 50, 60, 70, 80, 90, 100, 110 minutes, or at least 1, 2, 3, 4, 5, 6, or more hours. In a preferred embodiment, the Fraction II+III suspension will be stirred with finely divided silicon dioxide for at or about between 30 and 60 minutes. In another preferred embodiment, the Fraction II+III suspension will be stirred with finely divided silicon dioxide for at least 30 minutes.

In certain embodiments, filter aid, for example Celpure C300 (Celpure) or Hyflo-Supper-Cel (World Minerals), will be added to facilitate depth filtration. Filter aid can be added at a final concentration of from about 0.1 kg/kg Fraction II+III precipitate to about 0.7 kg/kg Fraction II+III precipitate, or from about 0.2 kg/kg Fraction II+III precipitate to about 0.6 kg/kg Fraction II+III precipitate, or from about 0.3 kg/kg Fraction II+III precipitate to about 0.5 kg/kg Fraction II+III precipitate. In certain embodiments, the filter aid will be added at a final concentration of about 0.1 kg/kg Fraction II+III precipitate, or about 0.2, 0.3, 0.4, 0.5, 0.6, or 0.7 kg/kg Fraction II+III precipitate.

In order to remove the non-solubilized and adsorbed fraction of the Fraction II+III precipitate (i.e., the Fraction II+III filter cake) after silicon dioxide treatment, the suspension is filtered, typically using depth filtration. Depth filters that may be employed in the methods provided herein include, metallic, glass, ceramic, organic (such as diatomaceous earth) depth filters, and the like. Examples of suitable filters include, without limitation, Cuno 50SA, Cuno 90SA, and Cuno VRO6 filters (Cuno). Alternatively, the separation step can be performed by centrifugation rather than filtration. In a preferred embodiment, the finely divided silicon dioxide treated Fraction II+III paste suspension is filtered through a depth filter situated in a filter press.

5. The Albumin Pathway a) Third Precipitation Step—Fraction IV-1 Precipitation

In order to recover IaIp from the Fraction II+III supernatant, the solution is typically cooled to at or about between −1° C. and −9° C., the pH is adjusted to at or about between 5.0 and 5.5, and the alcohol concentration is adjusted to at or about between 18% and 25% (v/v). The solution is then maintained at or about between −1° C. and −9° C. for at least at or about 4 hours to allow for complete precipitation. In a preferred embodiment, the temperature of the solution is maintained at or about between −3° C. and −7° C. for the entirety of the precipitation. In another preferred embodiment, the pH of the solution is adjusted to at or about between 5.2 and 5.3. In yet another preferred embodiment, the alcohol concentration is adjusted to at or about 20%±1% (v/v). In one preferred embodiment, the precipitation is allowed to proceed for at least at or about 8 hours.

In one embodiment, a Fraction IV-1 precipitate is formed by cooling the solution to at or about between −3° C. and −7° C., adjusting the pH of the solution to at or about between 5.2 and 5.3, adjusting the alcohol concentration to at or about 20%±1%, and maintaining the temperature of the solution for at least at or about 8 hours.

The Fraction IV-1 supernatant and precipitate are then separated by a suitable method, such as centrifugation or filtration. In a preferred embodiment, the temperature of the Fraction IV-1 supernatant is maintained at or about between −1° C. and −7° C. during the separation process. When filtration is used to separate the precipitate and supernatant, filtration aid (for example, Celpure 300, Celite 501, Celite 505, or equivalent aid) is preferably added prior to filtration.

As compared to conventional methods of forming a Fraction VI-1 precipitate (Cohn et al., supra), the present invention provides, in several embodiments, methods that result in improved blood factor yields. In one embodiment, the precipitating alcohol is added in a fashion that finely disperses the alcohol or that rapidly disperses the alcohol at the point of addition. In one embodiment, the alcohol is added by spraying. In a second embodiment, the alcohol is added from below or directly adjacent to a stirring apparatus, for example, a propeller.

In another embodiment, one or more pH modifying agent is added in a fashion that finely disperses or that rapidly disperses the pH modifying agent at the point of addition. In one embodiment, the pH modifying agent is added by spraying. In a second embodiment, the pH modifying agent is added from below or directly adjacent to a stirring apparatus, for example, a propeller. In a third embodiment, the pH modifying agent is added by sprinkling a solid pH modifying agent over a delocalized area.

In yet another embodiment, both the precipitating alcohol and the solution used to adjust the pH are added in a fashion that finely disperses or that rapidly disperses the pH modifying agent at the point of addition. In one embodiment both the precipitating alcohol and the solution used to adjust the pH are added by spraying, rather than by fluent addition.

In yet another embodiment, the pH of the solution is adjusted after addition of the alcohol. In a related embodiment, the pH of the solution is adjusted during addition of the alcohol. In one embodiment, the pH of the solution is maintained at the desired pH during the precipitation hold or incubation time by continuously adjusting the pH of the solution. In a preferred embodiment, the alcohol is ethanol.

In certain embodiments, the pH of the solution to at or about between 5.2 and 5.3 immediately after or during the adjustment of the precipitating alcohol concentration. In another embodiment, the process improvement is realized by maintaining the pH of the solution to at or about between 5.2 and 5.3 continuously during the precipitation incubation period. In other embodiments, the pH of the solution is adjusted to at or about between 5.2 and 5.3 immediately after or during the adjustment of the precipitating alcohol concentration, or to a pH of at or about 4.5, 4.6, 4.7, 4.8, 4.9, 5.0, 5.1, 5.2, 5.3, 5.4, 5.5, 5.6, 5.7, 5.8, 5.9, 6.0 or higher immediately after or during the adjustment of the precipitating alcohol concentration. In a particular embodiment, the pH of the solution is adjusted to at or about between 5.2 and 5.3 immediately after or during the adjustment of the precipitating alcohol concentration. In certain embodiments, the pH of the solution is maintained at or about between 5.2 and 5.3 continuously during the adjustment of the precipitating alcohol concentration. In one embodiment, the pH is maintained at the desired pH during the precipitation hold or incubation time by continuously adjusting the pH of the solution. In one embodiment, the alcohol is ethanol.

b) Alternate Albumin Pathway—Fraction I+II+III Precipitation

Alternatively, a Fraction IV-1 precipitate may be formed from a different plasma fraction, for example a Fraction I+II+III supernatant. Typically, Fraction I+II+III precipitation is performed by adjusting the pH of a cryo-poor plasma fraction to at or about between 6.5 and 7.5, adjusting the temperature of the fraction to at or about between −1° C. and −9° C., and adding alcohol to a final concentration of at or about between 15% and 25% (v/v). In a preferred embodiment, the pH of the cryo-poor plasma fraction is adjusted to at or about between 6.7 and 7.1, or at 6.9±0.2. In another preferred embodiment, the temperature of the plasma fraction is adjusted to at or about between −3° C. and −7° C. In yet another preferred embodiment, alcohol (preferably ethanol) is added to a final concentration of at or about between 20% and 25% (v/v). In a particular embodiment, alcohol is added to a final concentration of at or about 20% (v/v). In one embodiment, precipitation is allowed to proceed, while the solution is mixed, for at least at or about 2 hours, or at least at or about 4, 6, 8, 10, or 12 hours. In a preferred embodiment, the solution is mixed for at or about 2 hours, the pH of the solution is checked and adjusted if needed, and the precipitation is allowed to proceed for at least at or about 10 hours after adjustment of the pH.

In a preferred embodiment, a Fraction I+II+III precipitation is performed by adjusting the pH of a cryo-poor plasma fraction to at or about between 6.7 and 7.1, adjusting the temperature of the fraction to at or about between −3° C. and −7° C., and adding alcohol to a final concentration of at or about between 20% and 25% (v/v).

The Fraction I+II+III supernatant and precipitate are then separated by a suitable method, such as centrifugation or filtration. When filtration is used to separate the precipitate and supernatant, filtration aid (for example, Celpure 300, Celite 501, Celite 505, or equivalent aid) is preferably added prior to filtration. The recovered Fraction I+II+III supernatant is then processed to recover IaIp, for example, by Fraction IV-1 precipitation.

As compared to conventional methods of forming a Fraction I+II+III precipitate (Newman et al., *J Biol. Chem.* (1955) November; 217(1):31-41), the present invention provides, in several embodiments, methods that result in improved blood factor yields. In one embodiment, the precipitating alcohol is added in a fashion that finely disperses the alcohol or that rapidly disperses the alcohol at the point of addition. In one embodiment, the alcohol is added by spraying. In a second embodiment, the alcohol is added from below or directly adjacent to a stirring apparatus, for example, a propeller.

In another embodiment, one or more pH modifying agent is added in a fashion that finely disperses or that rapidly disperses the pH modifying agent at the point of addition. In one embodiment, the pH modifying agent is added by spraying. In a second embodiment, the pH modifying agent is added from below or directly adjacent to a stirring apparatus, for example, a propeller. In a third embodiment, the pH modifying agent is added by sprinkling a solid pH modifying agent over a delocalized area.

In yet another embodiment, both the precipitating alcohol and the solution used to adjust the pH are added in a fashion that finely disperses or that rapidly disperses the pH modifying agent at the point of addition. In one embodiment both the precipitating alcohol and the solution used to adjust the pH are added by spraying, rather than by fluent addition.

In yet another embodiment, the pH of the solution is adjusted after addition of the alcohol. In a related embodiment, the pH of the solution is adjusted during addition of the alcohol. In one embodiment, the pH of the solution is maintained at the desired pH during the precipitation hold or incubation time by continuously adjusting the pH of the solution. In a preferred embodiment, the alcohol is ethanol.

In certain embodiments, the pH of the solution is adjusted to at or about between 6.5 and 7.5 after the addition of the precipitating alcohol. In other embodiments, the pH of the solution is adjusted to at or about between 6.7 and 7.1 after addition of the precipitating alcohol. In yet other embodiments, the pH of the solution is adjusted to at or about 6.5 or at or about 6.6, 6.7, 6.8, 6.9, 7.0, 7.1, 7.2, 7.3, 7.4, or 7.5 after addition of the precipitating alcohol. In a particular embodiment, the pH of the solution is adjusted to at or about 6.9 after addition of the precipitating alcohol. As such, in certain embodiments, a reduced amount of blood factor is irreversibly lost in the precipitate fraction due to protein denaturation, as compared to an analogous precipitation step in which the pH of the solution is adjusted prior to but not after addition of the precipitating alcohol. In one embodiment, the pH is maintained at the desired pH during the precipitation hold or incubation time by continuously adjusting the pH of the solution. In a preferred embodiment, the alcohol is ethanol.

6. Extraction of IaIp

IaIp may be extracted from suitable plasma fractionation precipitates such as Fraction I, Fraction II+III, and Fraction IV-1 precipitates described above, Kistler and Nischmann Precipitate A or Precipitate B precipitates, or a Fraction II+III filter cake by the addition of an IaIp extraction buffer, which can be used to re-suspend the precipitate or filter cake at a ratio of at or about between 1:1 and 1:40 (part precipitate to parts extraction buffer). In a preferred embodiment, IaIp may be extracted by addition of an extraction buffer at a ratio of at or about between 1:20 and 1:30. For example, in one preferred embodiment, IaIp is extracted by addition of an extraction buffer at a ratio of at or about 1:20. In a second preferred embodiment, IaIp is extracted by addition of an extraction buffer at a ratio of at or about 1:25. In yet a third preferred embodiment, IaIp is extracted by addition of an extraction buffer at a ratio of at or about 1:30. Other suitable re-suspension ratios may be used, for example at or about 1:1, or 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:28, 1:39, 1:40, or higher.

In one embodiment, IaIp can be extracted from a precipitate or filter cake by re-suspending the precipitate or filter cake in the extraction buffer. In certain embodiments, the precipitate or filter cake is re-suspended in a volume of extraction buffer, for example at or about 1:25 or at or about 1:30, and the suspension is stirred for a length of time sufficient to solubilize the IaIp content of the precipitate or filter cake.

In another embodiment, IaIp can be extracted from a precipitate or filter cake by re-circulating an IaIp extraction buffer through a precipitate or filter cake or pellet. In a preferred embodiment, where a precipitate or filter cake is separated from a supernatant by filtration in a filter press, the extraction buffer is re-circulated through the filter press for a time sufficient to extract the IaIp from the precipitate.

For example, in one embodiment, IaIp extraction buffer is either used to re-suspend or re-circulated through a Fraction I precipitate (e.g., a Fraction I filter cake or centrifugation pellet) at a ratio of 1 part precipitate to 30 parts of extraction buffer. Other suitable re-suspension ratios may be used, for example from about 1:1, or 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:28, 1:39, 1:40, and the like. In a preferred embodiment, the Fraction I filter cake will remain in the filter press used to filter the precipitate from the supernatant during the extraction process.

In another embodiment, IaIp extraction buffer is either used to re-suspend or re-circulated through a Fraction II+III precipitate (e.g., a Fraction II+III precipitate filter cake or centrifugation pellet) at a ratio of 1 part precipitate to 30 parts of extraction buffer. Other suitable re-suspension ratios may be used, for example from about 1:1, or 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:28, 1:39, 1:40, and the like. In a preferred embodiment, the Fraction II+III filter cake will remain in the filter press used to filter the precipitate from the supernatant during the extraction process.

In another embodiment, IaIp extraction buffer is either used to re-suspend or re-circulated through a Fraction II+III suspension filter cake at a ratio of 1 part precipitate to 30 parts of extraction buffer. Other suitable re-suspension ratios may be used, for example from about 1:1, or 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:28, 1:39, 1:40, and the like. In a preferred embodiment, the Fraction II+III filter cake will remain in the filter press used to filter the precipitate from the supernatant during the extraction process.

In another embodiment, IaIp extraction buffer is either used to re-suspend or re-circulated through a Fraction IV-1 precipitate (e.g., a Fraction IV-1 precipitate filter cake or centrifugation pellet) at a ratio of 1 part precipitate to 30 parts of extraction buffer. Other suitable re-suspension ratios may be used, for example from about 1:1, or 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:28, 1:39, 1:40, and the like. In a preferred embodiment, the Fraction IV-1 filter cake will remain in the filter press used to filter the precipitate from the supernatant during the extraction process.

In another embodiment, IaIp extraction buffer is either used to re-suspend or re-circulated through a Kistler and Nischmann Precipitate A precipitate (e.g., a Precipitate A precipitate filter cake or centrifugation pellet) at a ratio of 1 part precipitate to 30 parts of extraction buffer. Other suitable re-suspension ratios may be used, for example from about 1:1, or 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:28, 1:39, 1:40, and the like. In a preferred embodiment, the Precipitate A filter cake will remain in the filter press used to filter the precipitate from the supernatant during the extraction process.

In another embodiment, IaIp extraction buffer is either used to re-suspend or re-circulated through a Kistler and Nischmann Precipitate B precipitate (e.g., a Precipitate B precipitate filter cake or centrifugation pellet) at a ratio of 1 part precipitate to 30 parts of extraction buffer. Other suitable re-suspension ratios may be used, for example from about 1:1, or 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:28, 1:39, 1:40, and the like. In a preferred embodiment, the Precipitate B filter cake will remain in the filter press used to filter the precipitate from the supernatant during the extraction process.

In a preferred embodiment, the step of extracting IaIp from a filter cake or precipitant comprises recirculation of an IaIp extraction buffer through a filter press containing the IaIp filter cake or precipitant. In one embodiment, the step of extracting IaIp from a filter cake or precipitant comprises recirculation of an IaIp extraction buffer through a filter press containing the IaIp filter cake for at least 10 minutes. In other embodiments, the step of extracting IaIp from a filter cake or precipitant comprises recirculation of an IaIp extraction buffer through a filter press containing the IaIp filter cake for at or about between 10 and 60 minutes. In a preferred embodiment, the step of extracting IaIp from a filter cake or precipitant comprises recirculation of an IaIp extraction buffer through a filter press containing the IaIp filter cake for at or about between 20 and 40 minutes. In yet other embodiments, the step of extracting IaIp from a filter cake or precipitant comprises recirculation of an IaIp extraction buffer through a filter press containing the IaIp filter cake for at least at or about 10 minutes or at least at or about 15, 20, 25, 30, 35, 40, 45, 50, 55, 60, 65, 70, 75, 80, 85, or 90 minutes, or longer (e.g., at least at or about 2, 3, 4, 5, or 6 hours).

Generally, the extraction is performed at or about between 0° C. and 20° C., preferably at or about between 2° C. and 8° C. In certain embodiments, the extraction may be performed at or about 0° C., 1° C., 2° C., 3° C., 4° C., 5° C., 6° C., 7° C., 8° C., 9° C., or 10° C., 11° C., 12° C., 13° C., 14° C., 15° C., 16° C., 17° C., 18° C., 19° C., or 20° C. In a particular embodiment, the extraction is performed at or about between 2° C. and 10° C.

Any suitable buffer may be used for the extraction of IaIp from a precipitate or filter cake. Typical extractions buffers will contain at least a buffering agent and a salt. In certain embodiments, the extraction buffer will contain at or about between 10 and 250 mM of a buffering agent. In certain embodiments, the buffering agent will be present at a concentration of at or about 10 mM, or 20, 30, 40, 50, 60, 70, 80, 90, 100, 110, 120, 130, 140, 150, 160, 170, 180, 190, 200, 210, 220, 230, 240, 250 mM or more buffering agent. In certain embodiments, the extraction buffer will have an ionic strength of at or about between 5 and 100 mS/cm. In specific embodiments the extraction buffer will contain at or about between 50 and 500 mM salt. In certain embodiments, the salt will be present at a concentration of at or about 50 mM or at or about 75, 100, 125, 150, 175, 200, 225, 250, 300, 350, 400, 450, 500 mM or more salt.

IaIp extraction buffers will generally have a pH of at or about between 6.0 and 9.0. In certain embodiments, a Factor H extraction buffer will have a pH of at or about 6.0, or at or about 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. In a preferred embodiment, the IaIp buffer will have a pH at or about between 7.0 and 8.0. In a specific embodiment, the extraction buffer will have a pH of at or about 7.0. In another specific embodiment, the extraction buffer will have a pH of at or about 7.5. In another specific embodiment, the extraction buffer will have a pH of at or about 8.0. Non-limiting examples of buffering agents that may be used for the formulation of an IaIp extraction buffer include potassium phosphate, sodium phosphate, sodium acetate, sodium citrate, ammonium acetate, cacodylic acid, imidazole, boric acid, bicine, ACES, BES, BIS-Tris, BIS-Tris-propane, CAPS, CHES, glycine amide, glycylglycine, MES, MOPS, PIPES, HEPES, TAPS, TES, tricine, triethanolamine, and Tris.

In a preferred embodiment, the IaIp extraction buffer will include or consist of 25 mM Tris (pH 8.0); 5 mM EDTA; 200 mM NaCl. In a more preferred embodiment, the IaIp extraction buffer will include or consist of 100 mM sodium phosphate (pH 7.5); 150 mM sodium chloride.

7. Fourth Precipitation Step—Removal of Impurities

In one embodiment, the method further comprises precipitating impurities from an enriched IaIp composition to form a precipitate (herein referred to as "IaIp Precipitate 4") and a supernatant (herein referred to as "IaIp Supernatant 4"). In certain embodiments, this step comprises precipitating at least one impurity, for example a lipid or protein, from the composition and then separating the precipitate from the supernatant containing IaIp. Precipitants suitable for precipitating impurities from a plasma derived fraction are well known in the art and include, without limitation, alcohol (e.g., ethanol, methanol, etc.), water soluble polymers (e.g., PEG, dextrans, etc.), salts (e.g., ammonium phosphate, ammonium sulfate, sodium citrate, etc.), short chain fatty acids (e.g., hexanoic acid, heptanoic acid, caprylic acid, nanoic acid, decanoic acid, etc.), and the like. In certain embodiments, the precipitation may be facilitated by matching the pH of the solution to the isoelectric point of a component of interest, i.e., isoelectric point precipitation.

In a preferred embodiment, the method comprises the step of precipitating at least one impurity from an enriched IaIp composition with at or about between 10% and 20% ethanol at a pH at or about between 7.0 and 9.0. In a preferred embodiment, the method comprises the step of precipitating at least one impurity from an enriched IaIp composition with at or about between 12% and 18% ethanol at a pH at or about between 7.3 and 8.7. In a more preferred embodiment, the method comprises the step of precipitating at least one impurity from an enriched IaIp composition with at or about between 14% and 16% ethanol at a pH at or about between 7.5 and 8.5. In a more preferred embodiment, the method comprises the step of precipitating at least one impurity from an enriched IaIp composition with at or about between 14% and 16% ethanol at a pH at or about between 7.8 and 8.2. In a most preferred embodiment, the method comprises the step of precipitating at least one impurity from an enriched IaIp composition with at or about 15% ethanol and at or about a pH of 8.0.

The concentration of the precipitant, e.g., ethanol, may be adjusted to maximize the precipitation of one or more impurities and/or minimize the precipitation of Factor H. In certain embodiments, the precipitation may be performed by the addition of at or about 10%, 11%, 12%, 13%, 14%, 15%, 16%, 17%, 18%, 19% or 20% ethanol. In a preferred embodiment, the precipitation is performed by the addition of at or about between 12% and 18% ethanol. In a more preferred embodiment, the precipitation is performed with at or about between 13% and 17% ethanol. In a more preferred embodiment, the precipitation is performed with at or about between 14% and 16% ethanol. In a most preferred embodiment, the precipitation is performed with at or about 15% ethanol.

The pH of the solution may be adjusted to maximize the precipitation of one or more impurities and/or to minimize the precipitation of IaIp. In certain embodiments, the pH of the solution is adjusted to at or about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. In a preferred embodiment, the pH of the solution is adjusted to at or about between 7.2 and 8.8. In another preferred embodiment, the pH of the solution is adjusted to at or about between 7.3 and 8.7. In another preferred embodiment, the pH of the solution is adjusted to at or about between 7.4 and 8.6. In a more preferred embodiment, the pH of the solution is adjusted to at or about between 7.5 and 8.5. In a more preferred embodiment, the pH of the solution is adjusted to at or about between 7.6 and 8.4. In a more preferred embodiment, the pH of the solution is adjusted to at or about between 7.7 and 8.3. In a more preferred embodiment, the pH of the solution is adjusted to at or about between 7.8 and 8.2. In a more preferred embodiment, the pH of the solution is adjusted to at or about between 7.9 and 8.1. In a most preferred embodiment, the pH of the solution is adjusted to at or about 8.0.

8. Fifth Precipitation Step—IaIp Precipitation

In one embodiment, the enriched IaIp composition may be further purified subsequent to extraction from a Fraction I precipitate, Fraction II+III precipitate, Fraction IV-1 precipitate, Precipitate A precipitate, Precipitate B precipitate, or Fraction II+III filter cake by precipitating IaIp out of the enriched composition to form a precipitate (herein referred to as “IaIp Precipitate 5”) and a supernatant (herein referred to as “IaIp Supernatant 5”). In certain embodiments, an enriched IaIp composition may be subjected to a third precipitation step, as described above, to remove at least one impurity from the composition, as described above, and then to a fourth precipitation step to precipitate and recover IaIp.

In a preferred embodiment, precipitating IaIp from an enriched composition comprises the addition of at or about between 20% and 30% ethanol at a pH at or about between 5.0 and 7.0. In a preferred embodiment, the method comprises the step of precipitating IaIp with at or about between 22% and 28% ethanol at a pH at or about between 5.5 and 6.5. In a more preferred embodiment, the method comprises the step of precipitating IaIp with at or about between 24% and 26% ethanol at a pH at or about between 5.8 and 6.2. In a most preferred embodiment, the method comprises the step of precipitating IaIp with at or about 25% ethanol and at or about a pH of 6.0.

The concentration of the precipitant, e.g., ethanol, may be adjusted to maximize the precipitation IaIp and/or minimize the precipitation of one or more impurities. In certain embodiments, the precipitation may be performed by the addition of at or about 20%, 21%, 22%, 23%, 24%, 25%, 26%, 27%, 28%, 29% or 30% ethanol. In a preferred embodiment, the precipitation is performed by the addition at or about between 22% and 28% ethanol. In a more preferred embodiment, the precipitation is performed with at or about between 23% and 27% ethanol. With a more preferred embodiment, the precipitation is performed with at or about between 24% and 26% ethanol. In a most preferred embodiment, the precipitation is performed with at or about 25% ethanol.

The pH of the solution may be adjusted to maximize the precipitation IaIp and/or minimize the precipitation of one or more impurities. In certain embodiments, the pH of the solution is adjusted to at or about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0. In a preferred embodiment, the pH of the solution is adjusted to at or about between 5.2 and 6.8. In another preferred embodiment, the pH of the solution is adjusted to at or about between 5.3 and 6.7. In another preferred embodiment, the pH of the solution is adjusted to at or about between 5.4 and 6.6. In a more preferred embodiment, the pH of the solution is adjusted to at or about between 5.5 and 6.5. In a more preferred embodiment, the pH of the solution is adjusted to at or about between 5.6 and 6.4. In a more preferred embodiment, the pH of the solution is adjusted to at or about between 5.7 and 6.3. In a more preferred embodiment, the pH of the solution is adjusted to at or about between 5.8 and 6.2. In a more preferred embodiment, the pH of the solution is adjusted to at or about between 5.9 and 6.1. In a most preferred embodiment, the pH of the solution is adjusted to at or about 6.0.

9. Chromatographic Methods

In certain embodiments, the method for preparing an enriched IaIp composition further comprises at least one, preferably two or more, chromatographic steps to further enrich the purity of the composition. Generally, any suitable chromatographic method may be employed to further enrich the IaIp composition extracted from a Fraction I precipitate, Fraction II+III precipitate, Fraction IV-1 precipitate, Precipitate A precipitate, Precipitate B precipitate, or Fraction II+III filter cake.

In certain embodiments, the chromatographic step may comprise anion exchange chromatography (AEC), cation exchange chromatography (CEC), heparin affinity chromatography, hydrophobic exchange chromatography (HIC), hydroxyapatite chromatography (HAP), immuno-affinity chromatography, size exclusion chromatography (i.e., gel filtration), or other suitable chromatographic step. Chromatographic steps may be performed in either batch or column mode.

In a preferred embodiment, the method comprises the steps of: binding IaIp to an anion exchange resin; eluting IaIp from the anion exchange resin with an elution buffer, thereby forming a first eluate containing IaIp. In a more preferred embodiment, the method further comprises the steps of binding IaIp from the anion exchange eluate to a heparin affinity resin; and eluting the IaIp from the heparin affinity resin with an elution buffer, thereby forming a second eluate containing IaIp. In certain embodiments, the chromatographic methods may further comprise wash steps to remove loosely bound impurities from the chromatographic resin prior to the elution of IaIp. In certain embodiments, IaIp may be eluted from a chromatography resin by gradient elution, e.g., with a salt gradient, or by step elution, e.g., with buffers having increasing ionic strength.

Generally, the conductivity of the IaIp solution is adjusted to an appropriate ionic strength prior to binding IaIp onto a chromatographic resin. The ionic strength should be low enough to promote the interaction between IaIp and the resin, yet high enough to maintain the stability of the protein in solution. The requirements for the ionic strength of the solution will vary dependent upon factors such as the identity of the resin used (e.g., strong vs. weak anion exchange resin) and the starting purity of the solution. Various methods may be employed for reducing the ionic strength of a IaIp composition, including without limitation, dilution of the composition with a solution having a low ionic strength, precipitating IaIp from the starting composition and re-suspending in a buffer having lower ionic strength, ultrafiltration/diafiltration, desalting and/or buffer exchange chromatography, dialysis, and the like.

a) Anion Exchange

Any suitable anion exchange resin may be used in the methods provided herein. Non-limiting examples of anion exchange resins suitable for use include, diethylaminoethyl (DEAE), quaternary aminoethyl (QAE), and quaternary ammonium (Q) resins. In a preferred embodiment, the anion exchange resin used is DEAE-sepharose (diethylaminoethyl-sepharose).

In a preferred embodiment, IaIp is bound to a DEAE-sepharose resin in the presence of a low ionic strength loading buffer. Typically, the column will be equilibrated with the same loading buffer or a compatible buffer with an ionic strength similar to the loading buffer. In certain embodiments, the loading and/or equilibration buffer will have an ionic strength of less than at or about 12 mS/cm. In a preferred embodiment, the loading and/or equilibration buffer will have an ionic strength of less than at or about 10 mS/cm. In a most preferred embodiment, the loading and/or equilibration buffer will have an ionic strength of at or about 9 mS/cm. In a preferred embodiment, the loading and/or equilibration buffer will have a salt concentration of less than at or about 100 mM NaCl, or ionic strength corresponding to less than that of a 100 mM NaCl solution. In a more preferred embodiment, the loading and/or equilibration buffer will have a salt concentration of, or ionic strength corresponding to, less than at or about 75 mM NaCl. In a more preferred embodiment, the salt concentration, or corresponding ionic strength, will be at or about between 30 and 70 mM NaCl. In a most preferred embodiment, the salt concentration, or corresponding ionic strength, will be at or about 50 mM NaCl.

Optionally, after binding IaIp, the anion exchange resin may be washed with one or more buffers having ionic strengths intermediate of the loading buffer and the elution buffer. In certain embodiments, a wash buffer may have an ionic strength at or about between 3 mS/cm and 20 mS/cm. In a preferred embodiment, the wash buffer may have an ionic strength at or about between 5 mS/cm and 20 mS/cm. In another preferred embodiment, the wash buffer may have an ionic strength at or about between 10 mS/cm and 20 mS/cm. In certain embodiments, the wash buffer will have a salt concentration, or ionic strength corresponding to, at or about between 30 and 200 mM NaCl. In a preferred embodiment, the wash buffer will have a salt concentration, or ionic strength corresponding to, at or about between 70 and 200 mM NaCl. In certain embodiments, the wash buffer will have a salt concentration, or ionic strength corresponding to, at or about 30, 35, 40, 45, 50, 55, 60, 65, 70, 75, 80, 85, 90, 95, 100, 110, 120, 130, 140, 150, 160, 170, 180, 190, 200, 210, or 220 mM NaCl.

In one embodiment, the anion-exchange resin will be washed with a first buffer with sufficient ionic strength to elute Factor H from the resin and a second buffer with sufficient ionic strength to elute impurities, such as complement component 3 (C3) from the resin prior to elution of IaIp from the resin. In another embodiment, the anion exchange anion-exchange resin will be washed with at least a first buffer with sufficient ionic strength to elute Factor H and at least a second impurity, for example, C3, from the resin prior to elution of IaIp from the resin.

In certain embodiments, IaIp is eluted from the anion exchange resin (e.g., DEAE-sepharose) with an elution buffer having suitable ionic strength to disrupt the interaction between the resin and IaIp. In some embodiments, the elution buffer will not have a suitable ionic strength to disrupt the interaction between the resin and a contaminant that binds the resin with higher affinity than does IaIp. In certain embodiments, the elution buffer will have an ionic strength of at least at or about 18 mS/cm, preferably at least at or about 20 mS/cm. In one embodiment, the elution buffer will have an ionic strength of at least at or about 25 mS/cm. In certain embodiments, the elution buffer will have a salt concentration, or ionic strength corresponding to, at least at or about 155 mM NaCl. In certain embodiments, the elution buffer will have a salt concentration, or ionic strength corresponding to, at least at or about 160 mM NaCl or at least at or about 170, 180, 190, 200, 210, 220, 230, 240, 250, 260, 270, 280, 290, 300, or more NaCl.

b) Heparin Affinity

Any suitable heparin affinity resin may be used in the methods provided herein, for example, resins conjugated to a heparin ligand, derivative or mimetic of a heparin ligand, or heparin-like ligand (e.g., a sulfated glycosaminoglycan). In a preferred embodiment, the heparin affinity resin used is heparin-sepharose.

In one embodiment, IaIp is further purified by heparin affinity chromatography. In a preferred embodiment, IaIp from the eluate of an anion exchange chromatography step is further purified by heparin affinity chromatography, e.g., a heparin sepharose resin. In one embodiment, the ionic strength of the IaIp eluate is reduced by a suitable method, e.g., dilution, buffer exchange, dialysis, etc., and IaIp is bound to a heparin affinity resin. In certain embodiments, the ionic strength of the anion exchange eluate is reduced to less than at or about 10 mS/cm. In a preferred embodiment, the ionic strength is reduced to less than at or about 8 mS/cm. In another embodiment, the ionic strength is reduced to less than at or about 6 mS/cm. In certain embodiments, the ionic strength may be reduced to less than at or about 4 mS/cm, or less than at or about 5, 6, 7, 8, 9, 10, 11, or 12 mS/cm. In certain embodiments, the salt concentration of the anion exchange eluate, or ionic strength corresponding to, is reduced less than at or about 80 mM NaCl. In a preferred embodiment, the salt concentration, or ionic strength corresponding to, is reduced less than at or about 70 mM NaCl. In a more preferred embodiment, the salt concentration, or ionic strength corresponding to, is reduced to less than at or about 50 mM NaCl. In certain embodiments, the salt concentration, or ionic strength corresponding to, is reduced less than at or about 20 mM NaCl, or less than at or about 25, 30, 35, 40, 45, 50, 55, 60, 65, 70, 75, or 80 mM NaCl.

Optionally, after binding IaIp, the heparin affinity resin may be washed with one or more buffers having ionic strengths intermediate of the loading buffer and the elution buffer. In certain embodiments, a wash buffer may have an ionic strength at or about between 4 mS/cm and 10 mS/cm. In a preferred embodiment, the wash buffer may have an ionic strength at or about between 6 mS/cm and 8 mS/cm. In certain embodiments, the wash buffer will have a salt concentration, or ionic strength corresponding to, at or about between 40 and 80 mM NaCl. In a preferred embodiment, the wash buffer will have a salt concentration, or ionic strength corresponding to, between at or about 50 and 70 mM NaCl. In certain embodiments, the wash buffer will have a salt concentration, or ionic strength corresponding to, at or about 25, 30, 35, 40, 45, 50, 55, 60, 65, 70, 75, or 80 mM NaCl.

In certain embodiments, IaIp is eluted from the heparin affinity resin (e.g., DEAE-sepharose) with an elution buffer having suitable ionic strength to disrupt the interaction between the resin and IaIp. In some embodiments, the elution buffer will not have a suitable ionic strength to disrupt the interaction between the resin and a contaminant that binds the resin with higher affinity than does IaIp. In certain embodiments, the elution buffer will have an ionic strength of at least at or about 8 mS/cm, or at least at or about 9 mS/cm, or at least at or about 10 mS/cm. In certain embodiments, the elution buffer will have a salt concentration, or ionic strength corresponding to, at least at or about 80 mM NaCl. In another embodiment, the elution buffer will have a salt concentration, or ionic strength corresponding to, at least at or about 100 mM NaCl. In certain embodiments, the elution buffer will have a salt concentration, or ionic strength corresponding to, at least at or about 70 mM NaCl or at least at or about 75, 80, 85, 90, 95, 100, 105, 110, 120, 130, 140, 150, 160, 170, 180, 190, 200 mM, or more NaCl.

c) Additional Resins

In certain embodiments, the methods provided herein for the purification plasma-derived IaIp may further comprise the use of an additional chromatographic step, including without limitation, cation chromatography, hydroxyapatite chromatography, hydrophobic interaction chromatography, immuno-affinity chromatography, and the like.

Any suitable cation exchange resin may be used in the methods provided herein. Non-limiting examples of cation exchange resins suitable for use include, carboxymethyl (CM), sulfopropyl (SP), methyl sulfonate (S) resins.

Any suitable hydroxyapatite or other calcium-based resin may be used in the methods provided herein. Non-limiting examples of suitable resins include hydroxyapatite resins, fluorapatite resins, fluorhydroxyapatite resins, and the like.

Any suitable hydrophobic interaction chromatography resin may be used in the methods provided herein. Non-limiting examples of suitable resins include phenyl-resins, methyl-resins, butyl-resins, octyl-resins, and the like.

In certain embodiments, IaIp may be further enriched by immuno-affinity chromatography, for example with resins conjugated to an antibody, aptamer, or other binding molecule highly specific for one or more IaIp proteins, e.g., IaI or PaI.

d) Buffer System

In certain embodiments, individual or all chromatographic steps will rely on a common buffer system, in which only the salt concentration varies between the equilibration, wash, and elution buffers. Any suitable buffer may be used, e.g., a Tris buffer, a phosphate buffer, a citrate buffer, etc. In one embodiment, the pH of the loading buffer will range at or about between 6.0 and about 9.0. In a preferred embodiment, the pH of the buffer system is at or about between 7.0 and about 9.0. In a more preferred embodiment, the pH of the buffer system is at or about between 7.5 and about 8.5. In one preferred embodiment, the pH of the buffer system will be at or about 8.0.

10. Virus Inactivation and Removal

In certain embodiments, the methods provided herein for the preparation of an enriched IaIp composition will further include at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43):1023-1028, both of which are herein expressly incorporated by reference in their entirety for all purposes), nanofiltration (Hamamoto et al., *Vox Sang* 1989 (56)230-236 and Yuasa et al., *J Gen Virol*. 1991 (72 (pt 8)):2021-2024, both of which are herein expressly incorporated by reference in their entirety for all purposes), and low pH incubation at high temperatures (Kempf et al., *Transfusion* 1991 (31)423-427 and Louie et al., *Biologicals* 1994 (22): 13-19).

Viral inactivation or removal steps may be performed on any intermediate IaIp fractions generated during the manufacturing process. For example, in one embodiment, a viral inactivation or removal step may be performed on a Fraction I supernatant, Fraction II+III suspension, Fraction II+III filter cake extract, Supernatant 3, Precipitate 4 suspension, Fraction II+III supernatant, Fraction IV-1 suspension, Kistler and Nitschmann Precipitate A suspension, Kistler and Nitschmann Precipitate B suspension, anion exchange eluate, heparin affinity eluate, and the like.

In one embodiment, a viral inactivation or removal step is performed on a Fraction II+III filter cake extract. In a preferred embodiment the Fraction II+III filter cake extract is subjected to solvent and detergent (S/D) treatment.

In a second embodiment, a viral inactivation or removal step is performed on a Fraction II+III supernatant. In a preferred embodiment the Fraction II+III supernatant is subjected to solvent and detergent (S/D) treatment.

In a third embodiment, a viral inactivation or removal step is performed on a Fraction IV-1 suspension. In a preferred embodiment the Fraction IV-1 suspension is subjected to solvent and detergent (S/D) treatment.

In a fourth embodiment, a viral inactivation or removal step is performed on a Kistler and Nitschmann Precipitate A suspension. In a preferred embodiment the Kistler and Nitschmann Precipitate A suspension is subjected to solvent and detergent (S/D) treatment.

In a fifth embodiment, a viral inactivation or removal step is performed on a Kistler and Nitschmann Precipitate B suspension. In a preferred embodiment the Kistler and Nitschmann Precipitate B suspension is subjected to solvent and detergent (S/D) treatment.

In a sixth embodiment, a viral inactivation or removal step is performed on a Precipitation 3 supernatant (Supernatant 3). In a preferred embodiment the Precipitation 3 supernatant is subjected to solvent and detergent (S/D) treatment.

In a seventh embodiment, a viral inactivation or removal step is performed on a Precipitate 4 suspension. In a preferred embodiment the Precipitate 4 suspension is subjected to solvent and detergent (S/D) treatment.

In an eighth embodiment, a viral inactivation or removal step is performed on an anion exchange eluate. In a preferred embodiment the anion exchange eluate is subjected to solvent and detergent (S/D) treatment. In another preferred embodiment, the anion exchange eluate is subjected to nanofiltration.

In a ninth embodiment, a viral inactivation or removal step is performed on a heparin affinity eluate. In a preferred embodiment the heparin affinity eluate is subjected to solvent and detergent (S/D) treatment. In another preferred embodiment, the heparin affinity eluate is subjected to nanofiltration.

In a tenth embodiment, a viral inactivation or removal step is performed on an enriched IaIp bulk solution. In a preferred embodiment, the enriched IaIp bulk solution is subjected to nanofiltration. In another preferred embodiment, the enriched IaIp bulk solution is subjected to incubation at low pH and/or high temperatures.

In an eleventh embodiment, a lyophilized IaIp composition is heat treated to inactivate viruses.

In one embodiment, a manufacturing process for plasma-derived IaIp is provided that contains two viral inactivation or removal steps. In another embodiment, the process contains both solvent and detergent treatment and nanofiltration steps for the inactivation and removal of viral particles. In yet another embodiment, the manufacturing process comprises subjecting the Precipitate 3 supernatant to S/D treatment and the heparin eluate to nanofiltration. In one embodiment, the manufacturing process comprises subjecting the Precipitate 4 suspension or a clarified filtrate thereof to S/D treatment and the heparin eluate to nanofiltration. In another embodiment, the manufacturing process further comprises a viral inactivation step comprising incubating a final bulk IaIp composition at low pH for an extended period of time.

a) Solvent and Detergent (S/D) Treatment

In order to inactivate various viral contaminants which may be present in plasma-derived products, one or more IaIp intermediate solutions may be subjected to a solvent detergent (S/D) treatment. Methods for the detergent treatment of plasma derived fractions are well known in the art (for review see, Pelletier J P et al., *Best Pract Res Clin Haematol.* 2006; 19(1):205-42). Generally, any standard S/D treatment may be used in conjunction with the methods provided herein. For example, an exemplary protocol for an S/D treatment is provided below.

In one embodiment, Triton X-100, Tween-20, and tri(n-butyl)phosphate (TNBP) are added to an IaIp intermediate solution at final concentrations of about 1.0%, 0.3%, and 0.3%, respectively. The mixture is then stirred at a temperature between about 18° C. and about 25° C. for at least about an hour.

In one embodiment, a process improvement is realized by adding the S/D reagents (e.g., Triton X-100, Tween-20, and TNBP) by spraying rather than by fluent addition. In other embodiments, the detergent reagents may be added as solids to the IaIp intermediate solution, which is being mixed to ensure rapid distribution of the S/D components. In certain embodiments, it is preferable to add solid reagents by sprinkling the solids over a delocalized surface area of the filtrate such that local overconcentration does not occur, such as in fluent addition. In another embodiment, a process improvement is realized by pumping IaIp containing solution into a tank where the SD-reagents are already present either in concentrated or diluted form.

b) Nanofiltration and Ultra/Diafiltration

In order to further reduce the viral load of the IaIp composition provided herein, an IaIp fraction, for example the heparin affinity eluate, may be nanofiltered using a suitable nanofiltration device. In certain embodiments, the nanofiltration device will have a mean pore size of at or about between 15 nm and 200 nm. Examples of nanofilters suitable for this use include, without limitation, DVD, DV 50, DV 20 (Pall), Viresolve NFP, Viresolve NFR (Millipore), Planova 15N, 20N, 35N, and 75N (Planova). In a specific embodiment, the nanofilter may have a mean pore size of at or about between 15 nm and 72 nm, or at or about between 19 nm and 35 nm, or of at or about 15 nm, 19 nm, 35 nm, or 72 nm. In a preferred embodiment, the nanofilter will have a mean pore size of at or about 35 nm, such as an Asahi PLANOVA 35N filter or equivalent thereof.

Optionally, ultrafiltration/diafiltration may performed to further concentrate the nanofiltrate. In one embodiment, an open channel membrane is used with a specifically designed post-wash and formulation near the end the production process resulting in an IaIp composition of high concentration.

Subsequent to nanofiltration, the filtrate may be further concentrated by ultrafiltration and/or the buffer composition adjusted by diafiltration. In one embodiment, the nanofiltrate may be concentrated by ultrafiltration to a protein concentration of at or about between 0.5% and 10% (w/v). In certain embodiments, the ultrafiltration is carried out in a cassette with an open channel screen and the ultrafiltration membrane has a nominal molecular weight cut off (NMWCO) of less than at or about 150 kDa or less than at or about 140, 130, 120, 100, 90, 80, 70, 60, 50, 40, 30, or fewer kDa. In one embodiment, the ultrafiltration membrane has a NMWCO of no more than 50 kDa.

Upon completion of the ultrafiltration step, buffer exchange may be performed by diafiltration against a solution suitable for intravenous, intramuscular, intraocular, subcutaneous, or other appropriate administration. In certain embodiments, the diafiltration solution may comprise a stabilizing and/or buffering agent, for example, salts, sugars, and/or a non-ionic detergent (e.g., Polysorbate 80).

Typically, the minimum exchange volume is at least about 3 times the original concentrate volume or at least at or about 4, 5, 6, 7, 8, 9, or more times the original concentrate volume. The IaIp solution may be concentrated to a final protein concentration of at or about between 0.5% and 25% (w/v), or at or about between 1% and 25% (w/v), or at or about between 2% and 20% (w/v), or at or about between 3% and 15% (w/v), or at or about between 5% and 10% (w/v), or at or about between 9% and 12%, or at or about between 3% and 7% (w/v), or at or about between 8% and 14% (w/v), or at or about between 4% and 6%, or to a final concentration of at or about 0.1%, 0.25%, 0.5%, 1%, 2%, 3%, 4%, 5%, or 6%, 7%, 8%, 9%, 10%, 11%, 12%, 13%, 14%, 15%, 16%, 17%, 18%, 19%, 20%, 21%, 22%, 23%, 24%, 25% or higher.

c) Incubation at Low pH

In certain embodiments, an IaIp containing solution may be treated to reduce or inactivate the viral load of the composition. In one embodiment, this is achieved by adjusting the pH of the of the composition to low pH, for example, less than at or about 6.0, and incubating for at least about a week prior to releasing the composition. In a preferred embodiment, the pH of the bulk solution is adjusted to less than at or about 5.5 prior to incubation. In a more preferred embodiment, the pH of the solution is lowered to less than at or about 5.0 prior to incubation. In certain embodiments, the pH of the solution is lowered to less than at or about 6.0 or less than at or about 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, or lower prior to incubation.

In certain embodiments, the solution is then incubated for at least at or about one week, or at least at or about 2, 3, 4, or more weeks, or for at least at or about 1, 2, 3, or more months. In preferred embodiments, the composition is incubated at a temperature above at or about 20° C., or above at or about 25° C., or above at or about 30° C. In particular embodiments, the composition is incubated at a temperature of at or about 20° C., or at or about 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or higher.

d) Lyophilization and Heat Treatment

In yet other embodiments, the present invention provided lyophilized IaIp compositions. The viral activity of these lyophilized composition, which may have previously been subjected to other viral inactivation or removal steps such as S/D treatment or nanofiltration, may be further reduced by heat treatment of the lyophilized composition (i.e., Factor H lyo cake). Heat treatments for the inactivation of viral loads in blood factors are well known in the art (for example, see, Piszkiewicz et al., *Thromb Res.* 1987 Jul. 15; 47(2):235-41; Piszkiewicz et al., *Curr Stud Hematol Blood Transfus.* 1989; (56):44-54; Epstein and Fricke, *Arch Pathol Lab Med.* 1990 March; 114(3):335-40).

11. Formulation

Upon completion of the IaIp enrichment process, e.g., after a final diafiltration step, the protein concentration of the solution is adjusted to with a buffer, e.g., the diafiltration buffer, to a final concentration of at or about between 0.1% and 20%

(w/v), or at or about between 1% and 25% (w/v), or at or about between 2% and 20% (w/v), or at or about between 3% and 15% (w/v), or at or about between 5% and 10% (w/v), or at or about between 9% and 12%, or at or about between 3% and 7% (w/v), or at or about between 8% and 14% (w/v), or at or about between 4% and 6%, or to a final concentration of at or about 0.1%, 0.25%, 0.5%, 1%, 2%, 3%, 4%, 5%, 6%, 7%, 8%, 9%, 10%, 11%, 12%, 13%, 14%, 15%, 16%, 17%, 18%, 19%, 20%, or higher.

In certain embodiments, the formulated bulk solution may be further sterilized by filtering through a membrane filter with an absolute pore size of no more than at or about 0.22 micron, for example at or about 0.1 or 0.2 micron. In certain embodiments, the solution may be aseptically dispensed into final containers for proper sealing, with samples taken for testing.

B. Alcohol Addition

Advantageously, it has been found that, for purposes of fractionating blood products (e.g., IaIp, Factor H, IgG, Albumin) from plasma, addition of alcohol by a method that finely disperses or that rapidly disperses the alcohol at the point of addition results in reduced loss of IgG yields. Without being bound by theory, during fluent addition to a plasma fraction, transient local overconcentration of alcohol at the fluid ingress may lead to protein denaturation and irreversible loss and/or precipitation of a blood factor during steps in which the blood factor should remain in the supernatant. Furthermore, these effects may by amplified when large volumes of alcohol need to be added, such as in industrial scale purifications involving the fractionation of at least 100 L of pooled plasma.

In one embodiment, alcohol is added in one or more precipitation steps by a method that finely disperses the alcohol over a delocalized area. For example, alcohol can be added to a fractionation step by spraying onto the surface of the vessel or tank containing the plasma fraction. Accordingly, in one aspect of the methods provided herein, one or more precipitation steps are performed by the spray addition of alcohol. In certain embodiments, spray addition may be performed by using any pressurized device, such as a container (e.g., a spray bottle), that has a spray head or a nozzle and is operated manually or automatically to generate a fine mist from a liquid. In certain embodiments, spray addition is performed while the system is continuously stirred or otherwise mixed to ensure rapid and equal distribution of the liquid within the system.

In another embodiment, alcohol is added in one or more precipitation steps by a method that rapidly disperses the alcohol at the point of addition. For example, alcohol can be added from below the vessel or tank containing the plasma fraction, directly adjacent to a stirring apparatus (e.g., a propeller). In certain embodiments, fluent addition at a ingress directly adjacent to a stirring apparatus is performed while the system is continuously stirred or otherwise mixed to ensure rapid and equal distribution of the liquid within the system.

C. Adjustment of the pH

The protein precipitation profiles of plasma fractions is highly dependent upon the pH of the solution from which the plasma proteins are being precipitated. This fact has been exploited by scientists fractionating plasma proteins since the introduction of the Cohn and Oncley methods in 1946 and 1949, respectively. Traditionally, the pH of a plasma fraction is adjusted prior to alcohol addition to facilitate the highest recovery yields for the component(s) of interest. Advantageously, it has now been found that by adjusting the pH of the solution directly after addition of alcohol or concomitant with alcohol addition results in a more defined and reproducible precipitation. It was found that ethanol addition to plasma fractions results in fluctuations in the pH of the solution, generally by raising the pH of the solution. As such, by adjusting the pH of a plasma fraction to a predetermined pH before but not after alcohol addition, the precipitation reaction will occur at a non-optimal pH.

Likewise, precipitation of proteins from a plasma fraction will affect the electrostatic environment and will thus alter the pH of the solution. Accordingly, as a precipitation event is allowed to progress, the pH of the solution will begin to diverge from the predetermined pH value that allows for maximal recovery of the protein species of interest. This is especially true for precipitation events in which a large fraction of the protein is being precipitated, precipitation events in which a high alcohol content is used, and precipitation events that require a long incubation period.

Accordingly, in one aspect of the methods provided herein, the pH of a plasma fraction is adjusted directly after the addition of alcohol. In related embodiments, the pH may be adjusted before and after alcohol addition, or during and after alcohol addition, or before, during, and after alcohol addition. In a related embodiment, the pH of a solution is continuously adjusted during one or more alcohol precipitation events or incubations. In certain embodiments, the pH of a solution is continuously adjusted or maintained while the system is continuously stirred or otherwise mixed to ensure rapid and equal distribution of the pH modifying agent within the system.

Similar to the case of fluent alcohol addition, it has now been found that the fluent addition of large volumes of a pH modifying agent may cause transient local pH variations, resulting in unwanted protein denaturation or precipitation. Accordingly, in one embodiment of the methods provided herein, pH modifying agents may be introduced into one or more plasma fractionation steps by a method that finely disperses or that rapidly disperses the alcohol at the point of addition.

In one embodiment, a pH modifying agent is added in one or more steps by a method that finely disperses the pH modifying agent over a delocalized area. For example, the pH modifying agent can be added to a step by spraying onto the surface of the vessel or tank containing the plasma fraction. In another embodiment of the methods provided herein, the pH of a plasma fraction or precipitation step may be adjusted by spray addition of a pH modifying agent. In certain embodiments, spray addition may be performed by using any pressurized device, such as a container (e.g., a spray bottle), that has a spray head or a nozzle and is operated manually or automatically to generate a fine mist from a liquid. In certain embodiments, spray addition is performed while the system is continuously stirred or otherwise mixed to ensure rapid and equal distribution of the liquid within the system.

In another embodiment, a pH modifying agent is added in one or more steps by a method that rapidly disperses the pH modifying agent at the point of addition. For example, a pH modifying agent can be added from below the vessel or tank containing the plasma fraction, directly adjacent to a stirring apparatus (e.g., a propeller). In certain embodiments, fluent addition at a ingress directly adjacent to a stirring apparatus is performed while the system is continuously stirred or otherwise mixed to ensure rapid and equal distribution of the liquid within the system.

In yet another embodiment, a pH modifying agent is added in one or more steps by sprinkling a solid pH modifying agent over a delocalized area on the surface of the plasma fraction. In certain embodiments, addition by this means is performed while the system is continuously stirred or otherwise mixed to ensure rapid and equal distribution of the pH modifying agent within the system.

IV. Inter-Alpha-Inhibitor (IaIp) Compositions

In one aspect, the present invention provides IaIp compositions prepared according to a method described herein. In one embodiment, IaIp is prepared from materials otherwise discarded during the manufacture of a commercial plasma-derived blood product, for example IgG or Albumin. In one embodiment, an IaIp composition is provided, wherein IaIp is extracted from a Fraction I, Fraction IV-1, Fraction II+III or Fraction I+II+III precipitate, a Kistler and Nitschmann Precipitate A or Precipitate B precipitate, or a Fraction II+III filter cake.

IaIp as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", $3^{rd}$ edition, Kibbe et al., Pharmaceutical Press (2000)). In particular, the pharmaceutical composition comprising the polypeptide variant of the invention may be formulated in lyophilized or stable soluble form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. In one embodiment, the compositions of the invention are administered systemically. For systemic use, IaIp of the invention is formulated for parenteral (e.g. intravenous, subcutaneous, intramuscular, intraperitoneal, intracerebral, intrapulmonar, or intranasal) or enteral (e.g., oral, vaginal or rectal) delivery according to conventional methods. In one embodiment, IaIp is formulated for subcutaneous depot delivery. In yet other embodiments, IaIp is formulated for intranasal administration or administration via inhalation. The formulations can be administered continuously by infusion or by bolus injection. Some formulations encompass slow release systems. Preferred routes of administration will depend upon the indication being treated, managed, or prevented. For example, in one embodiment, wherein IaIp is administered for the treatment of sepsis, the preferred route of administration will be parenteral. In a specific embodiment, wherein IaIp is administered for the treatment of sepsis, the route of administration will be intravenous. A skilled physician will readily be able to determine the preferred route of administration for the particular affliction being treated, managed, or prevented.

A. Aqueous Compositions

In one aspect, the present invention provides aqueous compositions of plasma-derived IaIp prepared from materials otherwise discarded during the preparation of other commercially important blood products by plasma fractionation. Aqueous IaIp compositions prepared by the methods provided herein will have high IaIp content and purity. For example, IaIp compositions provided herein may have a protein concentration of at least about 3% (w/v) and an IaIp content of greater than about 90% purity.

In one embodiment, aqueous compositions of IaIp are provided that are prepared from a Fraction II+III filter cake. In one embodiment, an aqueous composition of IaIp is provided that is prepared by a method comprising the steps of: (i) extracting IaIp from a Fraction II+III filter cake, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step; and (vi) optionally performing at least one viral inactivation or removal step, thereby preparing an aqueous IaIp composition.

In a preferred embodiment, an IaIp composition is provided that is prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating IaIp from the first supernatant, in a second precipitation step, with between about 20% and about 25% alcohol at a pH of between about 6.7 and about 7.3 to form a second precipitate; (c) re-suspending the second precipitate to form a suspension; (d) mixing finely divided silicon dioxide ($SiO_2$) with the suspension from step (c); (e) filtering the suspension with a filter press, thereby forming a filter cake and a supernatant; and (f) extracting IaIp from the filter cake with an IaIp extraction buffer, thereby preparing an aqueous composition of IaIp.

In certain embodiments, IaIp is extracted from the filter cake by re-circulation of an extraction buffer through a filter press containing the filter cake. Generally, the extraction buffer will be re-circulated through the filter cake for between about 5 minutes and about 2 hours. In a preferred embodiment, the extraction buffer will be re-circulated through the filter cake for between about 10 minutes and about 60 minutes. In a more preferred embodiment, the extraction buffer will be re-circulated through the filter cake for between about 20 minutes and about 40 minutes. In another preferred embodiment, the extraction buffer will be re-circulated through the filter cake for about 30 minutes. In other embodiments, the extraction buffer will be re-circulated through the filter cake for at least about 5, 10, 15, 20, 25, 30, 35, 40, 45, 50, 55, 60, 65, 70, 75, 80, 85, 90, 95, 100, 105, 110, 115, 120, or more minutes.

In another embodiment, aqueous compositions of IaIp are provided that are prepared from a Fraction I precipitate. In one embodiment, an aqueous composition of IaIp is provided that is prepared by a method comprising the steps of: (i) extracting IaIp from a Fraction I precipitate, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step; and (vi) performing at least one viral inactivation or removal step, thereby preparing an aqueous IaIp composition.

In a preferred embodiment, aqueous compositions of IaIp are provided that are prepared from a Fraction I precipitate. In a particularly preferred embodiment, an IaIp composition is provided that is prepared by a method comprising the steps of: (a) precipitating IaIp from a cryo-poor plasma fraction, in a first precipitation step, with between about 6% and about 10% alcohol at a pH of between about 7.0 and about 7.5 to obtain a first precipitate and a first supernatant; and (b) extracting IaIp from the precipitate with an IaIp extraction buffer, thereby preparing an aqueous composition of IaIp.

In certain embodiments, IaIp is extracted from the Fraction I precipitate by re-circulation of an extraction buffer through a filter press containing the Fraction I precipitate. Generally, the extraction buffer will be re-circulated through the Fraction I precipitate for between about 5 minutes and about 2 hours. In a preferred embodiment, the extraction buffer will be re-circulated through the Fraction I precipitate for between about 10 minutes and about 60 minutes. In a more preferred embodiment, the extraction buffer will be re-circulated through the Fraction I precipitate for between about 20 minutes and about 40 minutes. In another preferred embodiment, the extraction buffer will be re-circulated through the Fraction I precipitate for about 30 minutes. In other embodiments, the extraction buffer will be re-circulated through the Fraction I precipitate for at least about 5, 10, 15, 20, 25, 30, 35, 40, 45, 50, 55, 60, 65, 70, 75, 80, 85, 90, 95, 100, 105, 110, 115, 120, or more minutes.

In another embodiment, aqueous compositions of IaIp are provided that are prepared from a Fraction IV-1 precipitate. In one embodiment, an aqueous composition of IaIp is provided that is prepared by a method comprising the steps of: (i) extracting IaIp from a Fraction IV-1 precipitate, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step; and (vi) performing at least one viral inactivation or removal step, thereby preparing an aqueous IaIp composition.

In a preferred embodiment, aqueous compositions of IaIp are provided that are prepared from a Fraction IV-1 precipitate. In a particularly preferred embodiment, an IaIp composition is provided that is prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating proteins from the first supernatant, in a second precipitation step, with between about 20% and about 25% alcohol at a pH of between about 6.7 and about 7.3 to form a second precipitate and a second supernatant; (c) precipitating IaIp from the second supernatant, in a third precipitation step, with between about 18% and about 23% alcohol at a pH of between about 5.0 to about 5.5 to form a third precipitate and a third supernatant; and (d) extracting IaIp from the third precipitate with an IaIp extraction buffer, thereby preparing an aqueous composition of IaIp.

In certain embodiments, IaIp is extracted from the Fraction IV-1 precipitate by re-circulation of an extraction buffer through a filter press containing the Fraction IV-1 precipitate. Generally, the extraction buffer will be re-circulated through the Fraction IV-1 precipitate for between about 5 minutes and about 2 hours. In a preferred embodiment, the extraction buffer will be re-circulated through the Fraction IV-1 precipitate for between about 10 minutes and about 60 minutes. In a more preferred embodiment, the extraction buffer will be re-circulated through the Fraction IV-1 precipitate for between about 20 minutes and about 40 minutes. In another preferred embodiment, the extraction buffer will be re-circulated through the Fraction IV-1 precipitate for about 30 minutes. In other embodiments, the extraction buffer will be re-circulated through the Fraction IV-1 precipitate for at least about 5, 10, 15, 20, 25, 30, 35, 40, 45, 50, 55, 60, 65, 70, 75, 80, 85, 90, 95, 100, 105, 110, 115, 120, or more minutes.

In one embodiment, aqueous compositions of IaIp are provided that are prepared from a Fraction II+III precipitate. In one embodiment, an aqueous composition of IaIp is provided that is prepared by a method comprising the steps of: (i) extracting IaIp from a Fraction II+III precipitate, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step; and (vi) optionally performing at least one viral inactivation or removal step, thereby preparing an aqueous IaIp composition.

In a preferred embodiment, an IaIp composition is provided that is prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating IaIp from the first supernatant, in a second precipitation step, with between about 20% and about 25% alcohol at a pH of between about 6.7 and about 7.3 to form a second precipitate; and (c) extracting IaIp from the second precipitate with an IaIp extraction buffer, thereby preparing an aqueous composition of IaIp.

In certain embodiments, IaIp is extracted from a Fraction II+III precipitate by re-circulation of an extraction buffer through a filter press containing the Fraction II+III precipitate. Generally, the extraction buffer will be re-circulated through the Fraction II+III precipitate for between about 5 minutes and about 2 hours. In a preferred embodiment, the extraction buffer will be re-circulated through the Fraction II+III precipitate for between about 10 minutes and about 60 minutes. In a more preferred embodiment, the extraction buffer will be re-circulated through the Fraction II+III precipitate for between about 20 minutes and about 40 minutes. In another preferred embodiment, the extraction buffer will be re-circulated through the Fraction II+III precipitate for about 30 minutes. In other embodiments, the extraction buffer will be re-circulated through the Fraction II+III precipitate for at least about 5, 10, 15, 20, 25, 30, 35, 40, 45, 50, 55, 60, 65, 70, 75, 80, 85, 90, 95, 100, 105, 110, 115, 120, or more minutes.

In one embodiment, aqueous compositions of IaIp are provided that are prepared from a Kistler and Nitschmann Precipitate A or B precipitate. In one embodiment, an aqueous composition of IaIp is provided that is prepared by a method comprising the steps of: (i) extracting IaIp from a Precipitate A or B precipitate, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step; and (vi) optionally performing at least one viral inactivation or removal step, thereby preparing an aqueous IaIp composition.

In certain embodiments, IaIp is extracted from a Fraction I, Fraction IV-1, Fraction II+III or Fraction I+II+III precipitate, a Kistler and Nitschmann Precipitate A or Precipitate B precipitate, or a Fraction II+III filter cake by the addition of a IaIp extraction buffer, which can be used to re-suspend the Fraction I, Fraction IV-1, or Fraction II+III precipitate, Kistler and Nitschmann Precipitate A or Precipitate B precipitate, or Fraction II+III filter cake at a ratio of 1 part precipitate to between about 25 parts and about 30 parts of extraction buffer. In other embodiments, the re-suspension ratio is at or about 1:4 to about 1:40, or from about 1:8 to about 1:30, or from about 1:10 to about 1:20, or from about 1:12 to about 1:18, or from about 1:13 to about 1:17, or from about 1:14 to about 1:16. In certain embodiments, the ratio may be about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher. In a preferred embodiment, IaIp is extracted by re-circulation of the extraction buffer through a filter or filter press containing a Fraction I, Fraction IV-1, Fraction II+III or Fraction I+II+III precipitate, a Kistler and Nitschmann Precipitate A or Precipitate B precipitate, or a Fraction II+III filter cake.

In certain embodiments, an aqueous composition of IaIp is provided, wherein the IaIp composition is prepared using a purification method described herein, wherein the method comprises the addition of one or more solutions, that would otherwise be introduced into a plasma fraction by fluent addition, by a method that finely disperses or that rapidly disperses the solution at the point of addition. For example, in certain embodiments the method will comprise the introduction of alcohol (e.g., ethanol) into a plasma fraction by spraying. In other embodiments, solutions that may be added to a plasma fraction by spraying include, without limitation, a pH modifying solution, a solvent solution, a detergent solution, a dilution buffer, a conductivity modifying solution, and the like. In one embodiment, one or more alcohol precipitation steps is performed by the addition of alcohol to a plasma fraction by spraying. In a second preferred embodiment, one or more pH adjustment steps is performed by the addition of a pH modifying solution to a plasma fraction by spraying.

In certain embodiments, an aqueous IaIp composition is provided that is prepared by a purification method described herein, wherein the method comprises adjusting the pH of a plasma fraction being precipitated after and/or concomitant with the addition of the precipitating agent (e.g., alcohol or polyethylene glycol). In some embodiments, the pH of a plasma fraction being actively precipitated is maintained throughout the entire precipitation incubation or hold step by continuous monitoring and adjustment of the pH. In one embodiment adjustment of the pH of a solution is performed by the spray addition of a pH modifying solution.

In one embodiment, the present invention provides aqueous IaIp compositions comprising a protein concentration of between about 0.1 g/L and about 250 g/L. In certain embodiments, the protein concentration of the IaIp composition is between about 0.1 g/L and about 50 g/L, or between about 0.5 g/L and about 25 g/L, or between about 1 g/L and about 10 g/L, or between about 50 g/L and about 200 g/L, or between about 70 g/L and about 150 g/L, or between about 90 g/L and about 120 g/L, or between about 30 g/L and about 70 g/L, or about 40 g/L and about 60 g/L or any suitable concentration within these ranges, for example about 0.1 g/L, 0.2 g/L, 0.3 g/L, 0.4 g/L, 0.5 g/L, 0.6 g/L, 0.7 g/L, 0.8 g/L, 0.9 g/L, 1 g/L, 2 g/L, 3 g/L, 4 g/L, 5 g/L, 6 g/L, 7 g/L, 8 g/L, 9 g/L, 10 g/L, or about 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, 150 g/L, 155 g/L, 160 g/L, 165 g/L, 170 g/L, 175 g/L, 180 g/L, 185 g/L, 190 g/L, 195 g/L, 200 g/L, 205 g/L, 210 g/L, 215 g/L, 220 g/L, 225 g/L, 230 g/L, 235 g/L, 240 g/L, 245 g/L, 250 g/L, or higher. In a preferred embodiment, IaIp compositions having high protein concentrations will also high levels of purity. In one embodiment, at least 90% of the protein in the composition will be IaIp. In a preferred embodiment, at least 95% of the protein in the composition will be IaIp.

The methods provided herein allow for the preparation of IaIp compositions having very high levels of purity. In one embodiment, at least about 90% of the total protein in a composition provided herein will be IaIp. In a preferred embodiment, at least about 95% of the total protein in a composition provided herein will be IaIp. In other embodiments, at least about 90%, 91%, 92%, 93%, 94%, 95%, 96%, 97%, 98%, 99%, 99.5%, or more of the total protein of the composition will be IaIp. In one preferred embodiment, at least 96% of the total protein of the composition will be IaIp. In a preferred embodiment, at least 97% of the total protein of the composition will be IaIp. In another preferred embodiment, at least 98% of the total protein of the composition will be IaIp. In another preferred embodiment, at least 99% of the total protein of the composition will be IaIp.

B. Pharmaceutical Compositions

In one aspect, the present invention provides pharmaceutical compositions of plasma-derived IaIp prepared from materials otherwise discarded during the preparation of other commercially important blood products by plasma fractionation. Pharmaceutical IaIp compositions prepared by the methods provided herein will have high IaIp content and purity. For example, IaIp compositions provided herein may have a protein concentration of at least about 1% (w/v) and an IaIp content of greater than about 90% purity. These high purity IaIp pharmaceutical compositions and formulations are suitable for therapeutic administration. In certain embodiments, the pharmaceutical compositions provided herein will consist of aqueous formulations of IaIp formulated for therapeutic administration. In other embodiments, the pharmaceutical compositions provided herein will consist of lyophilized formulations of IaIp formulated for therapeutic administration after reconstitution with water for injection (WFI) or a biologically compatible liquid, e.g., a saline or buffered solution.

In one embodiment, the pharmaceutical compositions provided herein are prepared by formulating an aqueous IaIp composition isolated using a method provided herein. Generally, the manufacturing pathway to the formulated composition will include at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43):1023-1028, both of which are herein expressly incorporated by reference in their entirety for all purposes), nanofiltration (Hamamoto et al., *Vox Sang* 1989 (56)230-236 and Yuasa et al., *J Gen Virol.* 1991 (72 (pt 8)):2021-2024, both of which are herein expressly incorporated by reference in their entirety for all purposes), and low pH incubation at high temperatures (Kempf et al., *Transfusion* 1991 (31)423-427 and Louie et al., *Biologicals* 1994 (22):13-19).

In one embodiment, pharmaceutical compositions of IaIp are provided that are prepared from a Fraction II+III filter cake. In one embodiment, a pharmaceutical composition of IaIp is provided that is prepared by a method comprising the steps of: (i) extracting IaIp from a Fraction II+III filter cake, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step;

(vi) performing at least one viral inactivation or removal step; and (vii) optionally lyophilizing the IaIp composition, thereby preparing a pharmaceutical IaIp composition.

In a preferred embodiment, a pharmaceutical IaIp composition is provided that is prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating IaIp from the first supernatant, in a second precipitation step, with between about 20% and about 25% alcohol at a pH of between about 6.7 and about 7.3 to form a second precipitate; (c) re-suspending the second precipitate to form a suspension; (d) mixing finely divided silicon dioxide ($SiO_2$) with the suspension from step (c); (e) filtering the suspension with a filter press, thereby forming a filter cake and a supernatant; (f) extracting IaIp from the filter cake with an IaIp extraction buffer; (g) performing at least one viral inactivation or removal step; and (h) optionally lyophilizing the composition, thereby preparing a pharmaceutical composition of IaIp.

In certain embodiments, IaIp is extracted from the filter cake by re-circulation of an extraction buffer through a filter press containing the filter cake. Generally, the extraction buffer will be re-circulated through the filter cake for between about 5 minutes and about 2 hours. In a preferred embodiment, the extraction buffer will be re-circulated through the filter cake for between about 10 minutes and about 60 minutes. In a more preferred embodiment, the extraction buffer will be re-circulated through the filter cake for between about 20 minutes and about 40 minutes. In another preferred embodiment, the extraction buffer will be re-circulated through the filter cake for about 30 minutes. In other embodiments, the extraction buffer will be re-circulated through the filter cake for at least about 5, 10, 15, 20, 25, 30, 35, 40, 45, 50, 55, 60, 65, 70, 75, 80, 85, 90, 95, 100, 105, 110, 115, 120, or more minutes.

In another embodiment, pharmaceutical compositions of IaIp are provided that are prepared from a Fraction I precipitate. In one embodiment, a pharmaceutical composition of IaIp is provided that is prepared by a method comprising the steps of: (i) extracting IaIp from a Fraction I precipitate, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step; (vi) performing at least one viral inactivation or removal step; and (vii) optionally lyophilizing the IaIp composition, thereby preparing a pharmaceutical IaIp composition.

In a preferred embodiment, pharmaceutical compositions of IaIp are provided that are prepared from a Fraction I precipitate. In a particularly preferred embodiment, an IaIp composition is provided that is prepared by a method comprising the steps of: (a) precipitating IaIp from a cryo-poor plasma fraction, in a first precipitation step, with between about 6% and about 10% alcohol at a pH of between about 7.0 and about 7.5 to obtain a first precipitate and a first supernatant; and (b) extracting IaIp from the precipitate with an IaIp extraction buffer; and (c) performing at least one viral inactivation or removal step, thereby preparing a pharmaceutical composition of IaIp.

In certain embodiments, IaIp is extracted from the Fraction I precipitate by re-circulation of an extraction buffer through a filter press containing the Fraction I precipitate. Generally, the extraction buffer will be re-circulated through the Fraction I precipitate for between about 5 minutes and about 2 hours. In a preferred embodiment, the extraction buffer will be re-circulated through the Fraction I precipitate for between about 10 minutes and about 60 minutes. In a more preferred embodiment, the extraction buffer will be re-circulated through the Fraction I precipitate for between about 20 minutes and about 40 minutes. In another preferred embodiment, the extraction buffer will be re-circulated through the Fraction I precipitate for about 30 minutes. In other embodiments, the extraction buffer will be re-circulated through the Fraction I precipitate for at least about 5, 10, 15, 20, 25, 30, 35, 40, 45, 50, 55, 60, 65, 70, 75, 80, 85, 90, 95, 100, 105, 110, 115, 120, or more minutes.

In another embodiment, pharmaceutical compositions of IaIp are provided that are prepared from a Fraction IV-1 precipitate. In one embodiment, a pharmaceutical composition of IaIp is provided that is prepared by a method comprising the steps of: (i) extracting IaIp from a Fraction IV-1 precipitate, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step; and (vi) performing at least one viral inactivation or removal step, thereby preparing a pharmaceutical composition IaIp composition.

In a preferred embodiment, pharmaceutical compositions of IaIp are provided that are prepared from a Fraction IV-1 precipitate. In a particularly preferred embodiment, an IaIp composition is provided that is prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating proteins from the first supernatant, in a second precipitation step, with between about 20% and about 25% alcohol at a pH of between about 6.7 and about 7.3 to form a second precipitate and a second supernatant; (c) precipitating IaIp from the second supernatant, in a third precipitation step, with between about 18% and about 23% alcohol at a pH of between about 5.0 to about 5.5 to form a third precipitate and a third supernatant; and (d) extracting IaIp from the third precipitate with an IaIp extraction buffer, thereby preparing a pharmaceutical composition of IaIp.

In certain embodiments, IaIp is extracted from the Fraction IV-1 precipitate by re-circulation of an extraction buffer through a filter press containing the Fraction IV-1 precipitate. Generally, the extraction buffer will be re-circulated through the Fraction IV-1 precipitate for between about 5 minutes and about 2 hours. In a preferred embodiment, the extraction buffer will be re-circulated through the Fraction IV-1 precipitate for between about 10 minutes and about 60 minutes. In a more preferred embodiment, the extraction buffer will be re-circulated through the Fraction IV-1 precipitate for between about 20 minutes and about 40 minutes. In another preferred embodiment, the extraction buffer will be re-circulated through the Fraction IV-1 precipitate for about 30 minutes. In other embodiments, the extraction buffer will be re-circulated through the Fraction IV-1 precipitate for at least about 5, 10, 15, 20, 25, 30, 35, 40, 45, 50, 55, 60, 65, 70, 75, 80, 85, 90, 95, 100, 105, 110, 115, 120, or more minutes.

In one embodiment, pharmaceutical compositions of IaIp are provided that are prepared from a Fraction II+III precipitate. In one embodiment, a pharmaceutical composition of IaIp is provided that is prepared by a method comprising the steps of: (i) extracting IaIp from a Fraction II+III precipitate, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step; and (vi) optionally performing at least one viral inactivation or removal step, thereby preparing a pharmaceutical composition IaIp composition.

In a preferred embodiment, an IaIp composition is provided that is prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating IaIp from the first supernatant, in a second precipitation step, with between about 20% and about 25% alcohol at a pH of between about 6.7 and about 7.3 to form a second precipitate; and (c) extracting IaIp from the second precipitate with an IaIp extraction buffer, thereby preparing a pharmaceutical composition of IaIp.

In certain embodiments, IaIp is extracted from a Fraction II+III precipitate by re-circulation of an extraction buffer through a filter press containing the Fraction II+III precipitate. Generally, the extraction buffer will be re-circulated through the Fraction II+III precipitate for between about 5 minutes and about 2 hours. In a preferred embodiment, the extraction buffer will be re-circulated through the Fraction II+III precipitate for between about 10 minutes and about 60 minutes. In a more preferred embodiment, the extraction buffer will be re-circulated through the Fraction II+III precipitate for between about 20 minutes and about 40 minutes. In another preferred embodiment, the extraction buffer will be re-circulated through the Fraction II+III precipitate for about 30 minutes. In other embodiments, the extraction buffer will be re-circulated through the Fraction II+III precipitate for at least about 5, 10, 15, 20, 25, 30, 35, 40, 45, 50, 55, 60, 65, 70, 75, 80, 85, 90, 95, 100, 105, 110, 115, 120, or more minutes.

In one embodiment, pharmaceutical compositions of IaIp are provided that are prepared from a Kistler and Nitschmann Precipitate A or B precipitate. In one embodiment, an aqueous composition of IaIp is provided that is prepared by a method comprising the steps of: (i) extracting IaIp from a Precipitate A or B precipitate, (ii) optionally performing a first precipitation step to precipitate at least one impurity from the IaIp composition, (iii) optionally performing a second precipitation step to precipitate IaIp from the composition, (iv) optionally performing at least one ion exchange chromatography step, (v) optionally performing at least one heparin affinity chromatography step; and (vi) optionally performing at least one viral inactivation or removal step, thereby preparing a pharmaceutical IaIp composition.

In certain embodiments, IaIp is extracted from a Fraction I, Fraction IV-1, Fraction II+III or Fraction I+II+III precipitate, a Kistler and Nitschmann Precipitate A or Precipitate B precipitate, or a Fraction II+III filter cake by the addition of a Factor H extraction buffer, which can be used to re-suspend the Fraction I, Fraction IV-1, or Fraction II+III precipitate, Kistler and Nitschmann Precipitate A or Precipitate B precipitate, or Fraction II+III filter cake at a typical ratio of 1 part precipitate to between about 25 parts and about 30 parts of extraction buffer. In other embodiments, the re-suspension ratio is at or about 1:4 to about 1:40, or from about 1:8 to about 1:30, or from about 1:10 to about 1:20, or from about 1:12 to about 1:18, or from about 1:13 to about 1:17, or from about 1:14 to about 1:16. In certain embodiments, the ratio may be about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher. In a preferred embodiment, IaIp is extracted by re-circulation of the extraction buffer through a filter or filter press containing the Fraction I, Fraction IV-1, or Fraction II+III precipitate, Kistler and Nitschmann Precipitate A or Precipitate B precipitate, or Fraction II+III filter cake. In a preferred embodiment, IaIp is extracted by re-circulation of the extraction buffer through a filter or filter press containing the Fraction I, Fraction IV-1, or Fraction II+III precipitate, Kistler and Nitschmann Precipitate A or Precipitate B precipitate, or Fraction II+III filter cake.

In certain embodiments, a pharmaceutical composition of IaIp is provided, wherein the IaIp composition is prepared using a purification method described herein, wherein the method comprises the addition of one or more solutions that would otherwise be introduced into a plasma fraction by fluent addition, by a method that finely disperses or that rapidly disperses the solution at the point of addition. For example, in certain embodiments the method will comprise the introduction of alcohol (e.g., ethanol) into a plasma fraction by spraying. In other embodiments, solutions that may be added to a plasma fraction by spraying include, without limitation, a pH modifying solution, a solvent solution, a detergent solution, a dilution buffer, a conductivity modifying solution, and the like. In a preferred embodiment, one or more alcohol precipitation steps is performed by the addition of alcohol to a plasma fraction by spraying. In a second preferred embodiment, one or more pH adjustment steps is performed by the addition of a pH modifying solution to a plasma fraction by spraying.

In certain embodiments, a pharmaceutical composition of IaIp is provided that is prepared by a purification method described herein, wherein the method comprises adjusting the pH of a plasma fraction being precipitated after and/or concomitant with the addition of the precipitating agent (e.g., alcohol or polyethylene glycol). In some embodiments, the pH of a plasma fraction being actively precipitated is maintained throughout the entire precipitation incubation or hold step by continuous monitoring and adjustment of the pH. In one embodiment adjustment of the pH of a solution is performed by the spray addition of a pH modifying solution.

In one embodiment, the present invention provides pharmaceutical IaIp compositions comprising a protein concentration of between about 10 g/L and about 250 g/L. In certain embodiments, the protein concentration of the IaIp composition is between about 50 g/L and about 200 g/L, or between about 70 g/L and about 150 g/L, or between about 90 g/L and about 120 g/L, or between about 30 g/L and about 70 g/L, or about 40 g/L and about 60 g/L, or any suitable concentration within these ranges, for example about 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, 150 g/L, 155 g/L, 160 g/L, 165 g/L, 170 g/L, 175 g/L, 180 g/L, 185 g/L, 190 g/L, 195 g/L, 200 g/L, 205 g/L, 210 g/L, 215 g/L, 220 g/L, 225 g/L, 230 g/L, 235 g/L, 240 g/L, 245 g/L, 250 g/L, or higher. In a preferred embodiment, IaIp compositions having high protein concentrations will also high levels of purity. In one embodiment, at least 90% of the protein in the composition will be IaIp. In a preferred embodiment, at least 95% of the protein in the composition will be IaIp.

The methods provided herein allow for the preparation of IaIp compositions having very high levels of purity. In one embodiment, at least about 90% of the total protein in a composition provided herein will be IaIp. In a preferred embodiment, at least about 95% of the total protein in a composition provided herein will be IaIp. In other embodiments, at least about 90%, 91%, 92%, 93%, 94%, 95%, 96%, 97%, 98%, 99%, 99.5%, or more of the total protein of the composition will be IaIp. In one preferred embodiment, at least 96% of the total protein of the composition will be IaIp. In a preferred embodiment, at least 97% of the total protein of the composition will be IaIp. In another preferred embodiment, at least 98% of the total protein of the composition will be IaIp. In another preferred embodiment, at least 99% of the total protein of the composition will be IaIp.

The pharmaceutical compositions provided herein will typically comprise one or more buffering agents or pH stabilizing agents suitable for intravenous, subcutaneous, and/or intramuscular administration. Non-limiting examples of buffering agents suitable for formulating an IaIp composition provided herein include glycine, histidine, or other amino acids, salts like citrate, phosphate, acetate, glutamate, tartrate, benzoate, lactate, gluconate, malate, succinate, formate, propionate, carbonate, or any combination thereof adjusted to an appropriate pH. Generally, the buffering agent will be sufficient to maintain a suitable pH in the formulation for an extended period of time.

In some embodiments, the concentration of buffering agent in the formulation will be between about 5 mM and about 500 mM. In certain embodiments, the concentration of the buffering agent in the formulation will be about 5 mM, 10 mM, 15 mM, 20 mM, 25 mM, 50, 75, 100, 125, 150, 175, 200, 225, 250, 275, 300, 325, 350, 375, 400, 425, 450, 475, 500 mM or higher.

In certain embodiments, the pH of the formulation will be between about pH 4.0 and pH 8.0.

In some embodiments, the pharmaceutical compositions provided herein may optionally further comprise an agent for adjusting the osmolarity of the composition. Non-limiting examples of osmolarity agents include mannitol, sorbitol, glycerol, sucrose, glucose, dextrose, levulose, fructose, lactose, polyethylene glycols, phosphates, sodium chloride, potassium chloride, calcium chloride, calcium gluconoglucoheptonate, dimethyl sulfone, and the like.

In some embodiments, the formulations provided herein will have osmolarities that are comparable to physiologic osmolarity, about 285 to 295 mOsmol/kg (Lacy et al., *Drug Information Handbook—Lexi-Comp* 1999:1254. In certain embodiments, the osmolarity of the formulation will be between about 200 mOsmol/kg and about 350 mOsmol/kg, preferably between about 240 and about 300 mOsmol/kg. In particular embodiments, the osmolarity of the formulation will be about 200 mOsmol/kg, or 210 mOsmol/kg, 220 mOsmol/kg, 230 mOsmol/kg, 240 mOsmol/kg, 245 mOsmol/kg, 250 mOsmol/kg, 255 mOsmol/kg, 260 mOsmol/kg, 265 mOsmol/kg, 270 mOsmol/kg, 275 mOsmol/kg, 280 mOsmol/kg, 285 mOsmol/kg, 290 mOsmol/kg, 295 mOsmol/kg, 300 mOsmol/kg, 310 mOsmol/kg, 320 mOsmol/kg, 330 mOsmol/kg, 340 mOsmol/kg, 340 mOsmol/kg, or 350 mOsmol/kg. In yet other embodiments, the osmolarity of the formulation will be higher, for example between about 200 mOsmol/kg and about 1000 mOsmol/kg, or about 400 mOsmol/kg, 450 mOsmol/kg, 500 mOsmol/kg, 550 mOsmol/kg, 600 mOsmol/kg, 650 mOsmol/kg, 700 mOsmol/kg, 750 mOsmol/kg, 800 mOsmol/kg, 850 mOsmol/kg, 900 mOsmol/kg, 950 mOsmol/kg, 1000 mOsmol/kg, or higher.

The IaIp formulations provided herein are generally stable in liquid form for an extended period of time. In certain embodiments, the formulations are stable for at least about 3 months at room temperature, or at least about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 months or more at room temperature. The formulation will also generally be stable for at least about 18 months under refrigerated conditions (typically between about 2° C. and about 8° C.), or for at least about 21, 24, 27, 30, 33, 36, 39, 42, 45, 48, 51, 54, 57, 60 months or more under refrigerated conditions.

In other embodiments, the IaIp formulations provided herein are generally stable in lyophilized form for an extended period of time. In certain embodiments, the formulations are stable for at least about 3 months at room temperature, or at least about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months at room temperature. The formulation will also generally be stable for at least about 18 months under refrigerated conditions (typically between about 2° C. and about 8° C.), or for at least about 21, 24, 27, 30, 33, 36, 39, 42, 45, 48, 51, 54, 57, or 60 months under refrigerated conditions.

In one aspect, the present invention is also directed to compositions containing IaIp purified according to the present invention and a pharmaceutically acceptable carrier for systemic or local ocular administration is administered to a mammal in need thereof. The compositions may further comprise additional therapeutic compounds that may be useful in the treatment of sepsis, such as for example antibiotics. The therapeutic compositions are formulated in accordance with methods known in the art for the particular route of administration desired.

According to the methods of the present invention, a composition comprising IaIp purified according to the methods described herein and a pharmaceutically acceptable carrier for systemic or local administration is administered to a mammal in need thereof.

V. Methods of Treatment

In yet other aspects, it is an object of the invention to provide methods for treating disorders and diseases associated with reduced IaIp function or IaIp dysfunction by administering a therapeutically effective amount of an IaIp composition provided herein. In one embodiment, the disease or disorder associated with reduced IaIp function or IaIp dysfunction is sepsis.

In one embodiment, the present invention provides a therapeutically effective dose of an IaIp composition prepared by a method disclosed herein for use in a method for treating a disease or disorder associated with reduced IaIp function or IaIp dysfunction in a subject in need thereof. In one embodiment, the disease or disorder associated with reduced IaIp function or IaIp dysfunction is sepsis.

In another aspect, it is an object of the invention to provide methods for treating diseases and disorders associated with increased plasma serine protease activity by administering a therapeutically effective amount of an IaIp composition provided herein. In one embodiment, the disease or disorder associated increased plasma serine protease activity is selected from sepsis, septic shock, endotoxic shock, disseminated intravascular coagulation, fibroproliferation, anthrax intoxication, cancer metastasis, tissue injury during surgery, kidney disease, vascular disease, coagulation, diabetes, and systemic inflammation.

In one embodiment, the present invention provides a therapeutically effective dose of an IaIp composition prepared by a method disclosed herein for use in a method for treating a disease or disorder associated with increased plasma serine protease activity in a subject in need thereof. In one embodiment, the disease or disorder associated increased plasma serine protease activity is selected from sepsis, septic shock, endotoxic shock, disseminated intravascular coagulation, fibroproliferation, anthrax intoxication, cancer metastasis, tissue injury during surgery, kidney disease, vascular disease, coagulation, diabetes, and systemic inflammation.

A. Administration

In accordance with the present invention, the time needed to complete a course of the treatment can be determined by a physician and may range from as short as one day to more than a month. In certain embodiments, a course of treatment can be from 1 to 6 months.

An effective amount of an IaIp preparation is administered to the subject by any suitable means to treat the disease or disorder. For example, in certain embodiments, IaIp may be administered by intravenous, subcutaneous, and/or intramuscular means. In a preferred embodiment, a method for treating sepsis in a subject in need thereof is provided comprising the intravenous (IV) administration of an IaIp composition to the patient.

In certain embodiments, the IaIp compositions provided herein can be administered either systemically or locally. Systemic administration includes: oral, subdermal, intraperitioneal, subcutaneous, transnasal, sublingual, or rectal routes of administration. Local administration includes: topical, subcutaneous, intramuscular, and intraperitoneal routes of administration.

In certain embodiments, the term "effective amount" refers to an amount of a IaIp preparation that results in an improvement or remediation of disease or condition in the subject. An effective amount to be administered to the subject can be determined by a physician with consideration of individual differences in age, weight, the disease or condition being treated, disease severity and response to the therapy. In certain embodiments, an IaIp preparation can be administered to a subject at dose of about 5 mg/kilogram to about 2000 mg/kilogram per administration. In certain embodiments, the dose may be at least about 5 mg/kg, or at least about 10 mg/kg, or at least about 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, or at least about 2000 mg/kg. The dosage and frequency of IaIp treatment will depend upon, among other factors, the disease or condition being treated and the severity of the disease or condition in the patient.

VI. Specific Embodiments

In one aspect, the present invention provides a method for preparing an enriched IaIp composition from plasma, the method comprising the steps of: (a) providing a cryo-poor plasma fraction; (b) precipitating IaIp from the cryo-poor plasma fraction in at least a first ethanol precipitation reaction to form an IaIp-containing precipitate; and (c) extracting IaIp from the IaIp-containing precipitate, thereby forming an enriched IaIp composition; wherein the IaIp-precipitate is selected from the group consisting of a Fraction II+III filter cake, a Fraction I precipitate, a Fraction I+II+III precipitate, a Fraction II+III precipitate, Fraction IV-1, a Kistler-Nitschmann Precipitate A, and a Kistler-Nitschmann Precipitate B.

In one aspect, the present invention provides a method for preparing an enriched Inter-alpha-Inhibitor (IaIp) composition from plasma, the method comprising the steps of: (i) forming a Fraction II+III precipitate from a plasma sample; (ii) re-suspending the Fraction II+III precipitate to form a Fraction II+III suspension; (iii) contacting the Fraction II+III suspension with a solid phase to remove the IaIp from the Fraction II+III suspension; and (iv) extracting the IaIp from the solid phase, thereby preparing an enriched IaIp composition.

In one embodiment of the methods provided above, the solid phase comprises finely divided silicon dioxide (SiO2).

In one embodiment of the methods provided above, the method comprises the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating IaIp from the first supernatant, in a second precipitation step, with between about 20% and about 25% alcohol at a pH of between about 6.7 and about 7.3 to form a second precipitate; (c) re-suspending the second precipitate to form a suspension; (d) mixing finely divided silicon dioxide (SiO2) with the suspension from step (c); (e) filtering the suspension with a filter press, thereby forming a filter cake and a supernatant; and (f) extracting IaIp from the filter cake with an IaIp extraction buffer, thereby preparing an enriched IaIp composition.

In one aspect, the present invention provides a method for preparing an enriched Inter-alpha-Inhibitor (IaIp) composition from plasma, the method comprising the steps of: (a) precipitating IaIp from a plasma sample to obtain a precipitate, (b) extracting IaIp from the precipitate with an IaIp extraction buffer, thereby preparing an enriched IaIp composition, wherein the precipitate is a Fraction I, Fraction I+II+III, Fraction II+III, Fraction IV-1, Precipitate A, or Precipitate B precipitate.

In one embodiment of the methods provided above, the step of forming a Fraction I precipitate comprises precipitating IaIp from a cryo-poor plasma fraction, in a first precipitation step, with between about 6% and about 10% alcohol at a pH of between about 7.0 and about 7.5 to obtain a Fraction I precipitate.

In one embodiment of the methods provided above, wherein IaIp is extracted from a Fraction IV-1 precipitate, the method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating proteins from the first supernatant, in a second precipitation step, with between about 20% and about 25% alcohol at a pH of between about 6.7 and about 7.3 to form a second precipitate and a second supernatant; (c) precipitating IaIp from the second supernatant, in a third precipitation step, with between about 18% and about 23% alcohol at a pH of between about 5.0 to about 5.5 to form a third precipitate and a third supernatant; and (d) extracting IaIp from the third precipitate with an IaIp extraction buffer, thereby preparing an enriched IaIp composition.

In one embodiment of the methods provided above, wherein IaIp is extracted from a Fraction IV-1 precipitate, the method comprising the steps of: (a) precipitating proteins from a cryo-poor plasma fraction, in a first precipitation step, with between about 18% and about 23% alcohol at a pH of between about 6.7 and about 7.2 to obtain a first precipitate and a first supernatant; (b) precipitating IaIp from the first supernatant, in a second precipitation step, with between about 18% and about 25% alcohol at a pH of between about 5.0 to about 5.5 to form a second precipitate and a second supernatant; and (c) extracting IaIp from the second precipitate with an IaIp extraction buffer, thereby preparing an enriched IaIp composition.

In one embodiment of the methods provided above, IaIp is extracted from more than one precipitate fraction.

In one aspect, the present invention provides a method for preparing an enriched Inter-alpha-Inhibitor (IaIp) composition from plasma, the method comprising the steps of: (a) fractionating a single aliquot of plasma to obtain enriched compositions of at least two blood products other than IaIp; (b) extracting IaIp from at least two different discard fractions created during the plasma fractionation with one or more extraction buffers; and (c) pooling the extracted IaIp fractions, thereby preparing an enriched IaIp composition.

In one embodiment of the methods provided above, the plasma is fractionated to obtain enriched compositions of IgG immunoglobulins and albumin.

In one embodiment of the methods provided above, the plasma is fractionated to obtain at least three blood products other than IaIp.

In one embodiment of the methods provided above, the method further comprises the step of: (g) precipitating impurities from the enriched IaIp composition, in an additional precipitation step, thereby forming a supernatant containing IaIp.

In one embodiment of the methods provided above, the additional precipitation step comprises precipitation with between about 10% and about 19% alcohol at a pH of between about 6.0 and about 8.0.

In one aspect, the present invention provides a method for preparing an enriched IaIp composition from plasma, the method comprising the steps of: (a) extracting IaIp from a plasma fraction selected from the group consisting of a Fraction II+III filter cake, a Fraction I precipitate, Fraction I+II+III precipitate, Fraction II+III precipitate, Fraction IV-1 precipitate, Precipitate A precipitate, or Precipitate B precipitate; and (b) precipitating impurities from the enriched IaIp composition, in an additional precipitation step, thereby preparing an enriched IaIp composition.

In one embodiment of the methods provided above, the method further comprises the step of: (h) precipitating IaIp, in an additional precipitation step.

In one embodiment of the methods provided above, IaIp is precipitated with between about 20% and about 25% alcohol at a pH of between about 6.0 and about 8.0.

In one embodiment of the methods provided above, the method further comprises the steps of: (g) binding IaIp from the enriched IaIp composition to an anion exchange resin; and (h) eluting the IaIp from the anion exchange resin with an elution buffer, thereby forming a first eluate containing IaIp.

In one embodiment of the methods provided above, the method further comprises the steps of: (i) binding IaIp from the first eluate to a heparin affinity resin; and (j) eluting the IaIp from the heparin affinity resin with an elution buffer, thereby forming a second eluate containing IaIp.

In one embodiment of the methods provided above, the IaIp present in either the first or second eluate is further enriched.

In one embodiment of the methods provided above, at least one of the precipitation steps comprises spray addition of alcohol.

In one embodiment of the methods provided above, all of the precipitation steps comprise spray addition of alcohol.

In one embodiment of the methods provided above, the pH of the solution is modified after the addition of alcohol in at least one of the first precipitation step, second precipitation step, or third precipitation step by the addition of a pH modifying agent.

In one embodiment of the methods provided above, the pH of the solution is modified after the addition of alcohol in all of the precipitation steps by the addition of a pH modifying agent.

In one embodiment of the methods provided above, the addition of a pH modifying agent comprises the spray addition of a pH modifying solution.

In one embodiment of the methods provided above, the pH of a precipitation step is modified before and after the addition of alcohol, during and after the addition of alcohol, or before, during, and after the addition of alcohol.

In one embodiment of the methods provided above, the pH of a precipitation step is maintained for the entire precipitation step by continuous adjustment of the pH.

In one embodiment of the methods provided above, the step of extracting IaIp comprises re-circulating an IaIp extraction buffer through a filter press containing a plasma fraction selected from the group consisting of a Fraction II+III filter cake, a Fraction I, Fraction I+II+III, Fraction II+III, Fraction IV-1, Precipitate A, or Precipitate B precipitate.

In one embodiment of the methods provided above, the IaIp extraction buffer is re-circulated through the filter press for at least about 10 minutes.

In one embodiment of the methods provided above, the IaIp extraction buffer is re-circulated through the filter press for at least about 30 minutes.

In one embodiment of the methods provided above, the IaIp extraction buffer comprises has a pH of at least about 0.3 units different from the isoelectric point of at least one IaIp protein.

In one aspect, the present invention provides a method for preparing an enriched Inter-alpha-Inhibitor (IaIp) composition from plasma, the method comprising the steps of: (a) extracting IaIp from a precipitate formed during the fractionation of cryo-poor plasma, wherein the extract contains IaIp and Factor H; (b) binding the IaIp and Factor H to an anion exchange resin; (c) eluting the Factor H from the resin with a first elution buffer; and (d) eluting the IaIp from the resin with a second elution buffer, thereby preparing an enriched IaIp composition.

In one aspect, the present invention provides a method for preparing an enriched Inter-alpha-Inhibitor (IaIp) composition from plasma, the method comprising the steps of: (a) extracting IaIp from a precipitate formed during the fractionation of cryo-poor plasma, wherein the extract contains IaIp and Factor H; (b) binding the IaIp to an anion exchange resin under conditions where Factor H does not bind to the anion exchange resin; and (c) eluting the IaIp from the resin with an elution buffer, thereby preparing an enriched IaIp composition.

In one embodiment of the methods provided above, the method further comprises the steps of: (e) binding the IaIp in the enriched IaIp composition to a heparin affinity column; and (f) eluting the IaIp from the heparin affinity column.

In one embodiment of the methods provided above, the enriched IaIp composition is further subjected to at least one viral inactivation step.

In one embodiment of the methods provided above, the viral inactivation step comprises treatment with a solvent and/or detergent, nanofiltration, heat treatment, or incubation at low pH.

In one embodiment of the methods provided above, a single Inter-alpha-Inhibitor protein (IaIp) species is isolated.

In one embodiment of the methods provided above, the IaIp species is Inter-alpha-Trypsin Inhibitor (IaI).

In one embodiment of the methods provided above, the IaIp species is Pre-alpha-Inhibitor (PaI).

In one embodiment of the methods provided above, the IaIp species is isolated by an antibody affinity method.

In one aspect, the present invention provides an aqueous solution of IaIp prepared by a method according to any one of claims 1 to 40.

In one embodiment of the IaIp solutions provided above, at least 90% of the protein content of the solution is IaIp.

In one aspect, the present invention provides a pharmaceutical composition of IaIp prepared by a method according to any one of claims 1 to 40.

In one embodiment of the IaIp pharmaceutical compositions provided above, at least 95% of the protein content of the solution is IaIp.

In one embodiment of the IaIp pharmaceutical compositions provided above, the composition is formulated for intravenous administration.

In one embodiment of the IaIp pharmaceutical compositions provided above, the composition comprises a lyophilized formulation of IaIp.

In one aspect, the present invention provides a method for treating a disease or disorder associated with IaIp dysfunction in a subject in need thereof, the method comprising administering a therapeutically effective dose of an IaIp composition prepared by a method according to any one of claims 1 to 40.

In one embodiment of the methods provided above, the disease or disorder associated with IaIp dysfunction is sepsis.

In one aspect, the present invention provides a method for treating a disease or disorder associated with increased plasma serine protease activity in a subject in need thereof, the method comprising administering a therapeutically effective dose of an IaIp composition prepared by a method according to any one of claims 1 to 40.

In one embodiment of the methods provided above, the disease or disorder associated with increased plasma serine protease activity is selected from the group consisting of sepsis, septic shock, endotoxic shock, disseminated intravascular coagulation, fibroproliferation, anthrax intoxication, cancer metastasis, tissue injury during surgery, kidney disease, vascular disease, coagulation, diabetes, and systemic inflammation.

VII. Examples

The following examples are provided by way of illustration only and not by way of limitation. Those of skill in the art will readily recognize a variety of non-critical parameters that could be changed or modified to yield essentially the same or similar results.

Example 1

Figure 2:
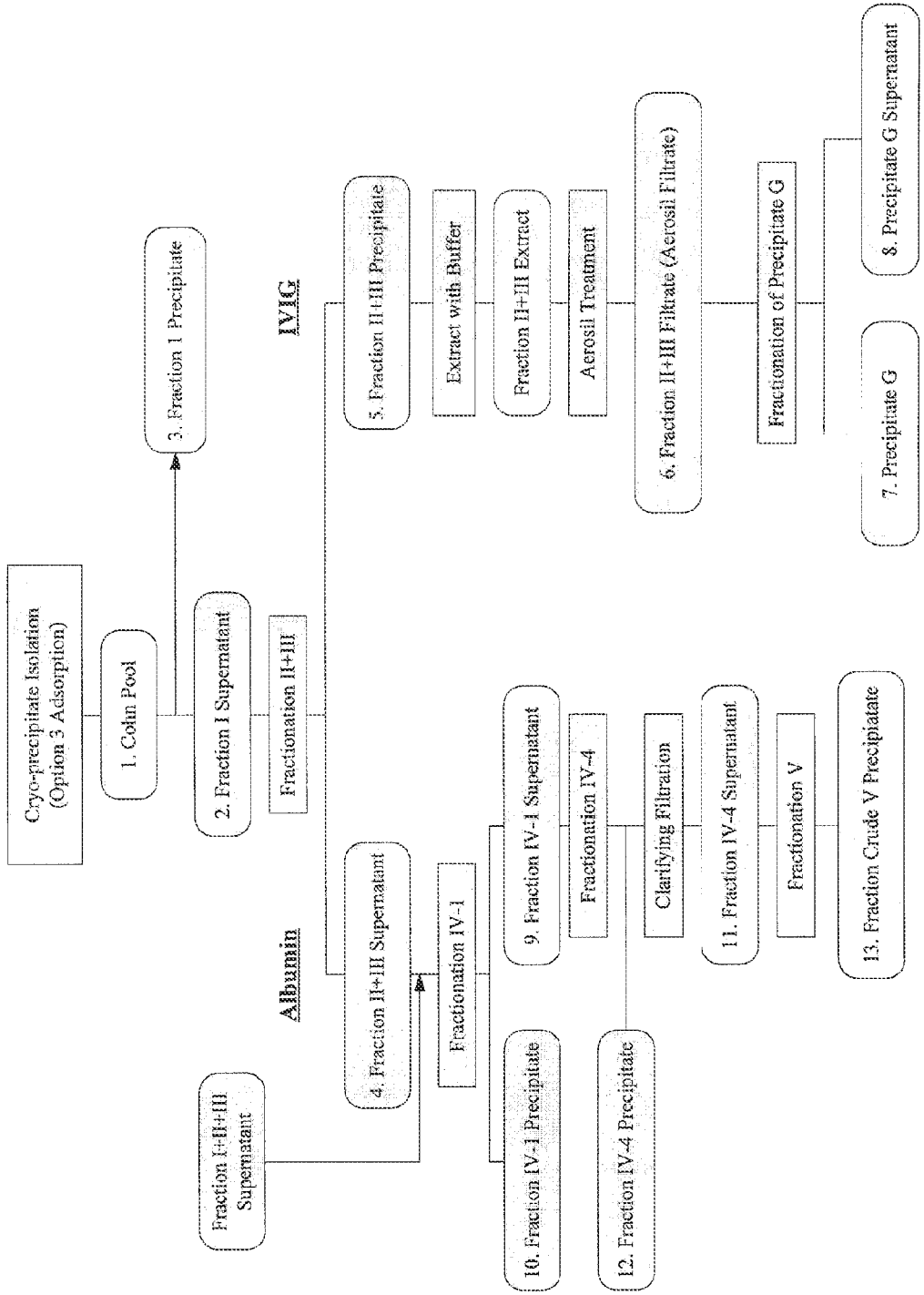
FIG. 2. Overview of an exemplary plasma fractionation scheme. Adopted from Zhuo et al., JBC 279 (2004): 38079-38082.

To determine an economically beneficial scheme for the manufacture of Inter-alpha-Inhibitor (IaIp) from a plasma sample, which allows for the recovery of additional blood factors from the same plasma sample, a lot of pooled human plasma was subjected to industrial fractionation according to the scheme outlined in the flow-diagram shown in FIG. 2. The fate of IaIp in the industrial fractionation process was followed by Western blot using an antibody specific for the small subunit, bikunin. Due to the size difference between IaI and PaI, the anti-bikunin antibody allowed for the identification of both proteins in the fractionation process, which were distinguished based on their migration on the SDS-PAGE gel (FIG. 3).

As seen in FIG. 3, a majority of the IaIp present in the pooled plasma sample was fractionated into three major fractions, the Fraction I precipitate, the Fraction II+III precipitate filter cake, and the Fraction IV-1 precipitate. Advantageously, all three of these fractions are typically discarded during the manufacture of IgG (Fraction I precipitate and Fraction II+III filter cake) and albumin (Fraction I and Fraction IV-1 precipitates). As such, it was postulated that IaI and PaI could be purified from these fractions, without modification to the IgG and albumin manufacturing processes.

Example 2

The present example describes experiments performed to determine the feasibility of extracting IaIp from a Fraction II+III filter cake. Briefly, the Fraction II+III filter cake from the plasma fractionation performed in Example 1 was dissolved in an IaIp extraction buffer (25 mM Tris (pH 8.0); 5 mM EDTA; 200 mM NaCl) at a ratio of 25:1 (mL buffer:g filtercake). The dissolved protein solution was clarified by centrifugation and filtration through a 0.45 μm filter. The conductivity of the resulting suspension was then adjusted by diluting the solution 3:1 with low salt extraction buffer (25 mM Tris (pH 8.0); 5 mM EDTA).

The clarified Fraction II+III filter cake suspension was then loaded onto a DEAE-Sepharose chromatograph column equilibrated with a low salt buffer (25 mM Tris; 5 mM EDTA; 50 mM NaCl; pH 8.0). A linear gradient from 50 mM NaCl to 500 mM NaCl (25 mM Tris; 5 mM EDTA; NaCl; pH 8.0) was then used to elute the IaIp from the DEAE-Sepharose column, the eluate of which was collected fractionally as shown by the chromatograph in FIG. 4A. Samples of the eluate fractions were analyzed by Western blot analysis (FIGS. 4B and 4C) to determine that IaIp eluted off of the anion exchange column in the third of three major peaks.

Figure 5A:
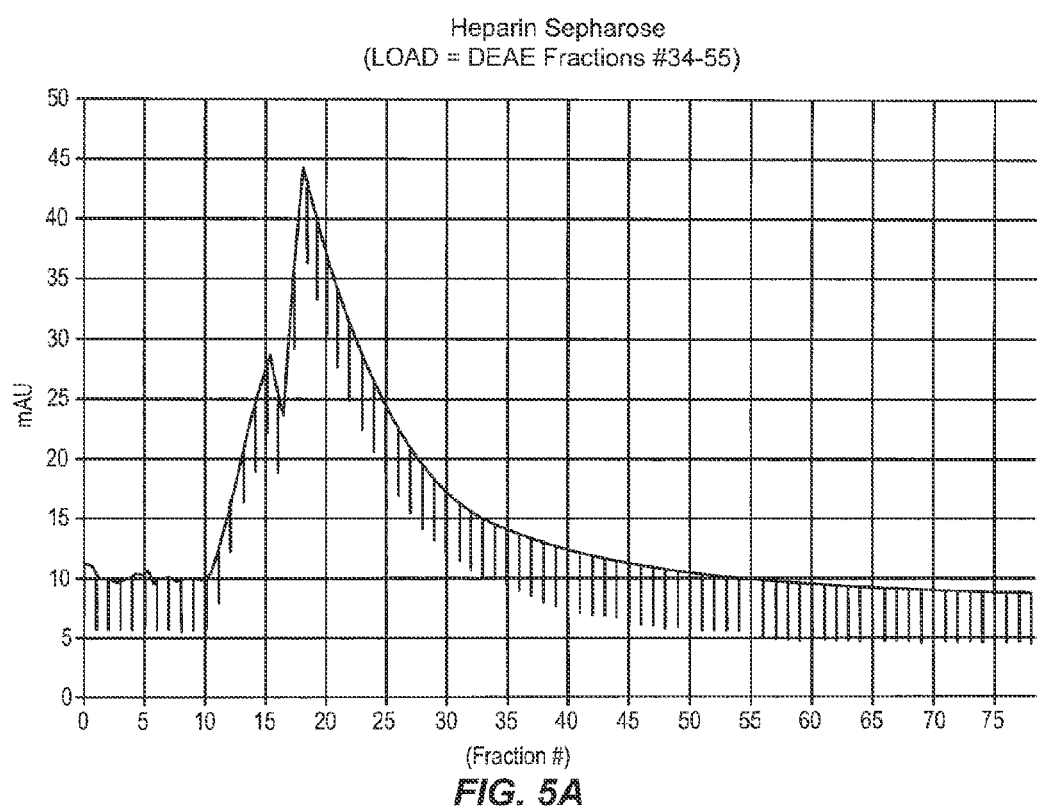
FIG. 5. (A) Chromatograph of a Heparin-Sepharose enrichment step of an IaIp purification process utilizing a modified Fraction II+III filter cake as the starting material. (B) Western blot analysis of the Heparin-Sepharose chromatography using an anti-Bikunin antibody.
Figure 5B:
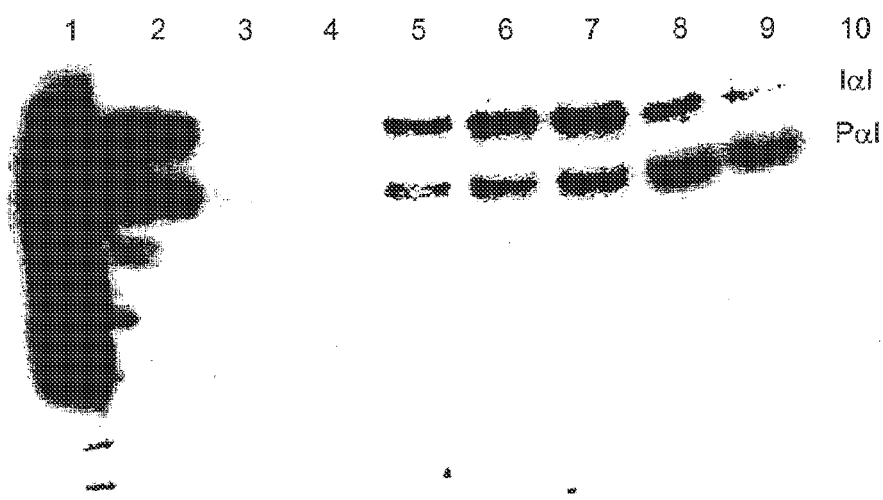
Figure 6:
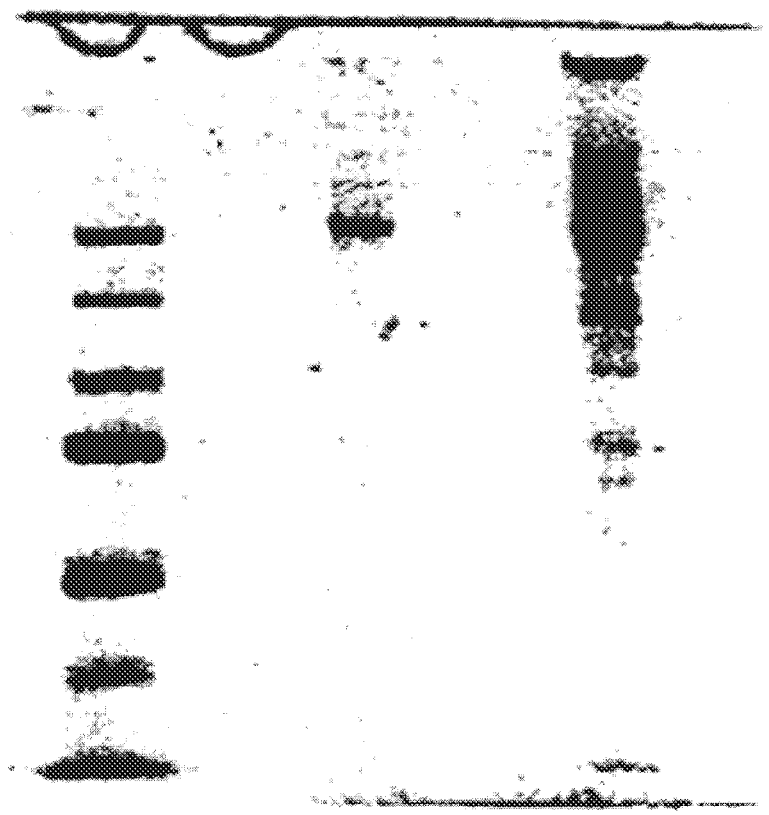
FIG. 6. SDS-Page analysis of an enriched IaIp composition prepared from a modified Fraction II+III filter cake. Lane 1: molecular weight markers (250, 150, 100, 75, 50, 37, 25, and 20 kDa markers); lane 2: 1 µl IaIp composition; lane 3: 5 µl IaIp composition.

The third elution peak from the DEAE-Sepharose chromatography elution, containing IaIp, was pooled based on the chromatograph and gel analysis performed, concentrated, and the conductivity was reduced by buffer exchange. The IaIp solution was then loaded onto a Heparin-Sepharose chromatography column equilibrated with a low salt buffer (25 mM Tris (pH 8.0); 5 mM EDTA; 50 mM NaCl). A linear gradient from 50 mM NaCl to 500 mM NaCl (25 mM Tris (pH 8.0); 5 mM EDTA; NaCl) was then used to elute the IaIp from the DEAE-Sepharose column, the eluate of which was collected fractionally as shown by the chromatograph in FIG. 5A. Samples of the eluate fractions were analyzed by Western blot analysis. As can be seen in FIG. 5B, IaIp eluted from the Heparin-Sepharose column in a single peak, which provides a pure IaIp composition.

Example 3

In order to aid with the industrial scale-up for the IaIp purification after extraction, an alternate purification scheme was devised that replaces the salt gradient elution of the chromatography columns with a series of step elutions that are more amenable to a large scale manufacturing process. Briefly, an IaIp composition extracted from a Fraction II+III filter cake, as described in Example 2, was loaded onto a DEAE-Sepharose chromatography column equilibrated with a low salt buffer (25 mM Tris; 5 mM EDTA; 65 mM NaCl; pH 8.0). The conductivity of the load was similar to that of the equilibration buffer (about 9 mS/cm). After the load, the column was washed with buffer containing 65 mM NaCl for 5 column volumes (CV) to remove the unbound protein impurities. The flow-through fractions contain very little IaIp as shown by the Western blot results in FIG. 7C.

In a first step elution, the salt concentration of the buffer (25 mM Tris (pH 8.0); 5 mM EDTA; NaCl) was increased to 100 mM NaCl (conductivity 12.6 mS/cm) for 5 CV to elute Factor H bound to the column. The salt concentration of the buffer was then increased to 155 mM NaCl (conductivity 18 mS/cm) for 6 CV to elute bound protein impurities from the column. The Western blot analysis shows that this intermediate wash fraction contains little IaIp (FIG. 7C). IaIp was then eluted off of the column by increasing the salt concentration of the column to 230 mM NaCl (conductivity of about 25 mS/cm). The IaIp came off the column in a sharp peak followed by a shoulder, as seen in the chromatograph provided in FIG. 7A. The corresponding coomassie stained SDS-PAGE gel (FIG. 7B) and Western blot (FIG. 7C) show that the majority of the Factor H is in the peak. The major IaIp fractions from the 230 mM NaCl elution were pooled together.

Figure 8A:
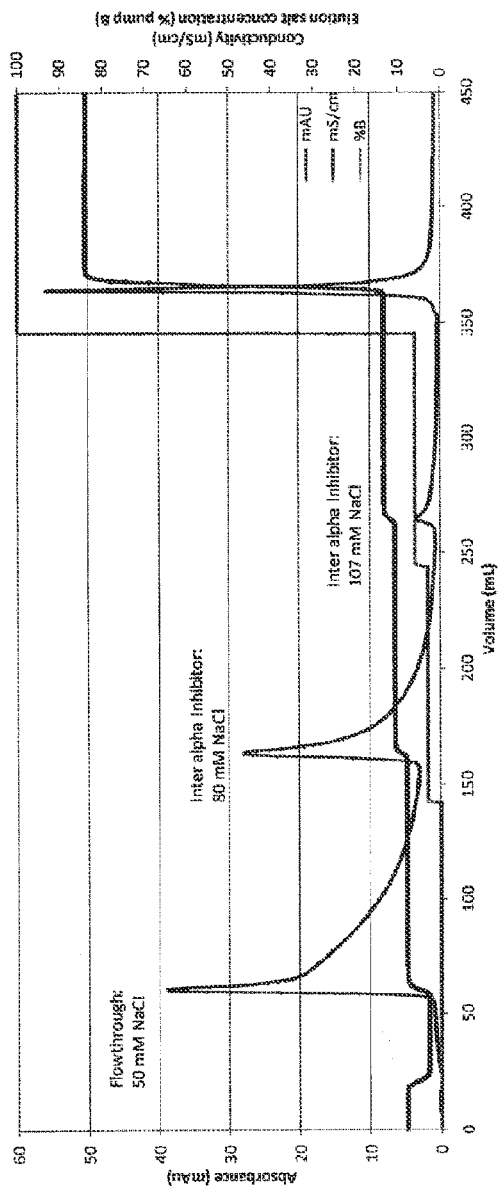
FIG. 8. (A) Chromatograph, (B) SDS-Page Analysis, and (C) Western blot analysis of Heparin-Sepharose chromatography performed with step-wise elution of a peak IaIp fraction enriched by DEAE chromatography. Lane 1 contains standard protein molecular weight markers; lane 2 contains a sample of the IaIp solution loaded onto the heparin resin; lanes 3, 4, and 5 contain samples of the flow through from the heparin load; lane 6 contains a sample of the 80 mM elution peak; lane 7 contains a sample of the 80 mM elution shoulder; and lane 8 contains a sample of the 107 mM elution peak.
Figure 8C:
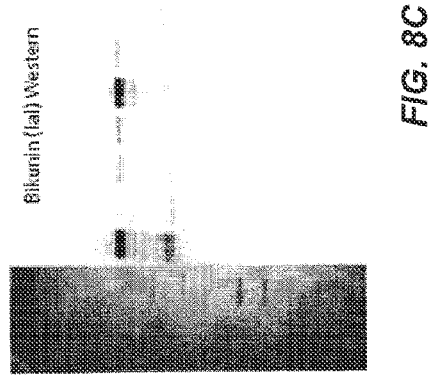

To reduce the salt concentration of the pooled IaIp fractions, the sample was dialyzed against low salt buffer to reduce the conductivity to about 8 mS/cm (around 50 mM NaCl). The sample was then passed through a 0.45 μm filter to remove any particulates. The filtered sample was then loaded onto a Heparin-Sepharose chromatography column equilibrated with a low salt buffer (25 mM Tris (pH 8.0); 5 mM EDTA; 50 mM NaCl). After the load, the column was washed with buffer containing 50 mM NaCl for 5 column volumes (CV) to remove the unbound protein impurities. The flow-through fractions contain very little IaIp as shown by the Western blot results in FIG. 8C.

Figure 8B:
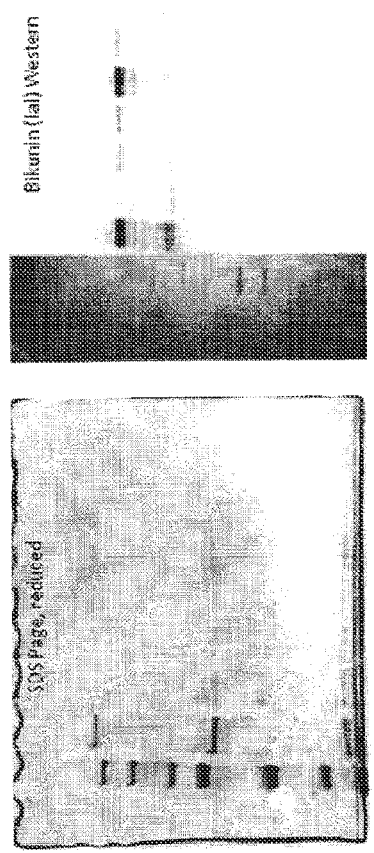

In a first step elution, the salt concentration of the buffer (25 mM Tris; 5 mM EDTA; NaCl; pH 8.0) was increased to 80 mM NaCl to elute IaIp from the column. The SDS-PAGE (FIG. 8B) and Western blot (FIG. 8C) analysis shows that the resulting IaIp pool contains some low molecular weight impurities that could be removed by size exclusion chromatography, ultrafiltration/diafiltration, and other methods well known in the art. A second elution step was performed with buffer containing 107 mM NaCl and another IaIp peak was eluted off the column. This fraction did not have any detected impurities. This method can be modified to optimized the process. In one embodiment, all of the IaIp may be eluted in a single step, for example with a single elution with buffer containing greater than 80 mM NaCl. The load and wash may still be performed at 50 mM NaCl, and Factor H elution may be done, for example, with buffer containing 107 mM NaCl. An extended wash at 50 mM NaCl or at a salt concentration of below 80 mM NaCl may be added after loading in an attempt to remove more weakly bound impurities from the IaIp pool.

The above chromatography steps can be modified to use buffer systems other than Tris/EDTA at pH 8. These processes can be adapted for buffers and solutions commonly used in manufacturing of biopharmaceuticals. An example is a purification scheme using phosphate buffer at pH 7. The key parameter to successful purification is manipulation of conductivity or ionic strength to achieve separation of the desired compound. If pH of the buffer system is maintained at pH 8, the conductivity of the elution buffers must be matched to the purification process described here. If the pH of the buffer system is changed, some adjustment of the ionic strength will be needed which can be done with standard techniques used in optimization of chromatographic processes.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing an enriched Inter-alpha-Inhibitor protein (IaIp) composition from plasma, the method comprising the steps of:
    (i) forming a Fraction II+III precipitate from a plasma sample by:
        (a) precipitating proteins from a Cohn pool, in a first precipitation step, with between about 6% and about 10% alcohol at a pH of between about 7.0 and about 7.5 to obtain a first precipitate and a first supernatant, and
        (b) precipitating proteins from the first supernatant, in a second precipitation step, with between about 20% and about 25% alcohol at a pH of between about 6.6 and about 7.2, thereby forming a Fraction II+III precipitate;
    (ii) suspending the Fraction II+III precipitate to form a Fraction II+III suspension;
    (iii) contacting the Fraction II+III suspension with a solid phase to remove the IaIp from the Fraction II+III suspension; and
    (iv) extracting the IaIp from the solid phase, thereby preparing an enriched IaIp composition.

2. The method of claim 1, wherein the solid phase comprises finely divided silicon dioxide ($SiO_2$).

3. The method of claim 1, wherein the method comprises the steps of:
    (i) forming a Fraction II+III precipitate from a plasma sample by:
        (a) precipitating proteins from a Cohn pool, in a first precipitation step, with between about 6% and about 10% alcohol at a pH of between about 7.0 and about 7.5 to obtain a first precipitate and a first supernatant;
        (b) precipitating IaIp from the first supernatant, in a second precipitation step, with between about 20% and about 25% alcohol at a pH of between about 6.6 and about 7.2, thereby forming a Fraction II+III precipitate;
    (ii) suspending the Fraction II+III precipitate to form a Fraction II+III suspension;
    (iii) contacting the Fraction II+III suspension with a solid phase to remove the IaIp from the Fraction II+III suspension by:
        (d) mixing finely divided silicon dioxide ($SiO_2$) with the Fraction II+III suspension from step (c); and
    (iv) extracting the IaIp from the solid phase by:
        (e) filtering the Fraction II+III suspension with a filter press, thereby forming a filter cake and a supernatant; and
        (f) extracting IaIp from the filter cake with an IaIp extraction buffer, thereby preparing an enriched IaIp composition.

4. The method of claim 1, wherein the pH of the solution is modified after the addition of alcohol in at least one of the first precipitation step or second precipitation step by the addition of a pH modifying agent.

5. The method of claim 4, wherein the pH of the solution is modified after the addition of alcohol in all of the precipitation steps by the addition of a pH modifying agent.

6. The method of claim 4, wherein the addition of a pH modifying agent comprises the spray addition of a pH modifying solution.

7. The method of claim 1, wherein the pH of a precipitation step is modified before and after the addition of alcohol, during and after the addition of alcohol, or before, during, and after the addition of alcohol.

8. The method of claim 1, wherein the pH of a precipitation step is maintained for the entire precipitation step by continuous adjustment of the pH.

9. The method of claim 1, wherein the step of extracting IaIp comprises re-circulating an IaIp extraction buffer through a filter press containing a Fraction II+III filter cake.

10. The method of claim 9, wherein the IaIp extraction buffer is re-circulated through the filter press for at least about 10 minutes.

11. The method of claim 9, wherein the IaIp extraction buffer is re-circulated through the filter press for at least about 30 minutes.

12. The method of claim 1, wherein the pH of the IaIp extraction buffer is at least about 0.3 units different from the isoelectric point of at least one IaIp protein.

13. The method of claim 1, wherein at least one of the precipitation steps comprises spray addition of alcohol.

14. The method of claim 1, wherein all of the precipitation steps comprise spray addition of alcohol.

15. The method of claim 1, further comprising a step of:
(v) precipitating impurities from the enriched IaIp composition, in an additional precipitation step, thereby forming a supernatant containing IaIp.

16. The method of claim 15, wherein the additional precipitation step comprises precipitation with between about 10% and about 19% alcohol at a pH of between about 6.0 and about 8.0.

17. The method of claim 15, further comprising a step of:
(vi) precipitating IaIp, in an additional precipitation step.

18. The method of claim 17, wherein IaIp is precipitated with between about 20% and about 25% alcohol at a pH of between about 6.0 and about 8.0.

19. The method of claim 1, further comprising the steps of:
(vii) binding IaIp from the enriched IaIp composition to an anion exchange resin; and
(viii) eluting the IaIp from the anion exchange resin with an elution buffer, thereby forming a anion exchange eluate containing IaIp.

20. The method of claim 19, further comprising the steps of:
(ix) binding IaIp from the first eluate to a heparin affinity resin; and
(x) eluting the IaIp from the heparin affinity resin with an elution buffer, thereby forming a heparin affinity eluate containing IaIp.

21. The method of claim 1, further comprising the steps of:
(ix) binding IaIp from the enriched IaIp composition to a heparin affinity resin; and
(x) eluting the IaIp from the heparin affinity resin with an elution buffer, thereby forming a heparin affinity eluate containing IaIp.

22. The method of claim 1, further comprising at least one viral inactivation step.

23. The method of claim 22, wherein the viral inactivation step comprises treatment with a solvent and/or detergent, nanofiltration, heat treatment, or incubation at low pH.

24. The method of claim 1, wherein a single Inter-alpha-Inhibitor protein (IaIp) species is isolated.

25. The method of claim 24, wherein the IaIp species is Inter-alpha-Trypsin Inhibitor (IaI).

26. The method of claim 24, wherein the IaIp species is Pre-alpha-Inhibitor (PaI).

27. The method of claim 24, wherein the IaIp species is isolated by an antibody affinity method.

28. The method of claim 3, wherein at least one of the precipitation steps comprises spray addition of alcohol.

29. The method of claim 3, wherein all of the precipitation steps comprise spray addition of alcohol.

30. The method of claim 3, wherein the pH of the solution is modified after the addition of alcohol in at least one of the first precipitation step or second precipitation step by the addition of a pH modifying agent.

31. The method of claim 30, wherein the pH of the solution is modified after the addition of alcohol in all of the precipitation steps by the addition of a pH modifying agent.

32. The method of claim 30, wherein the addition of a pH modifying agent comprises the spray addition of a pH modifying solution.

33. The method of claim 3, wherein the pH of a precipitation step is modified before and after the addition of alcohol, during and after the addition of alcohol, or before, during, and after the addition of alcohol.

34. The method of claim 3, wherein the pH of a precipitation step is maintained for the entire precipitation step by continuous adjustment of the pH.

35. The method of claim 3, wherein the step of extracting IaIp comprises re-circulating an IaIp extraction buffer through a filter press containing a Fraction II+III filter cake.

36. The method of claim 35, wherein the IaIp extraction buffer is re-circulated through the filter press for at least about 30 minutes.

37. The method of claim 3, wherein the pH of the IaIp extraction is at least about 0.3 units different from the isoelectric point of at least one IaIp protein.

38. The method of claim 3, further comprising the step:
(v) precipitating impurities from the enriched IaIp composition, in an additional precipitation step, thereby forming a supernatant containing IaIp.

39. The method of claim 38, wherein the additional precipitation step comprises precipitation with between about 10% and about 19% alcohol at a pH of between about 6.0 and about 8.0.

40. The method of claim 38, further comprising a step of:
(vi) precipitating IaIp, in an additional precipitation step.

41. The method of claim 40, wherein IaIp is precipitated with between about 20% and about 25% alcohol at a pH of between about 6.0 and about 8.0.

42. The method of claim 3, further comprising the steps of:
(vii) binding IaIp from the enriched IaIp composition to an anion exchange resin; and
(viii) eluting the IaIp from the anion exchange resin with an elution buffer, thereby forming a first eluate containing IaIp.

43. The method of claim 42, further comprising the steps of:
(ix) binding IaIp from the first eluate to a heparin affinity resin; and
(x) eluting the IaIp from the heparin affinity resin with an elution buffer, thereby forming a second eluate containing IaIp.

44. The method of claim 3, further comprising the steps of:
(ix) binding IaIp from the enriched IaIp composition to a heparin affinity resin; and
(x) eluting the IaIp from the heparin affinity resin with an elution buffer, thereby forming a second eluate containing IaIp.

45. The method of claim 3, further comprising at least one viral inactivation step.

46. The method of claim 45, wherein the viral inactivation step comprises treatment with a solvent and/or detergent, nanofiltration, heat treatment, or incubation at low pH.

47. The method of claim 3, wherein a single Inter-alpha-Inhibitor protein (IaIp) species is isolated.

48. The method of claim 47, wherein the IaIp species is Inter-alpha-Trypsin Inhibitor (IaI).

49. The method of claim 47, wherein the IaIp species is Pre-alpha-Inhibitor (PaI).

50. The method of claim 47, wherein the IaIp species is isolated by an antibody affinity method.

* * * * *